(12) United States Patent
Metcalfe et al.

(10) Patent No.: US 12,364,539 B2
(45) Date of Patent: Jul. 22, 2025

(54) ORTHOPAEDIC PLANNING SYSTEMS, INSTRUMENTATION AND METHODS OF REPAIR

(71) Applicant: Arthrex, Inc., Naples, FL (US)

(72) Inventors: Nick Metcalfe, Bonita Springs, FL (US); David Knopf, Bonita Springs, FL (US); Loren Crook, Fort Myers, FL (US); Matthew Provencher, Edwards, CO (US); Stephen Parada, Augusta, GA (US)

(73) Assignee: ARTHREX, INC., Naples, FL (US)

( * ) Notice: Subject to any disclaimer, the term of this patent is extended or adjusted under 35 U.S.C. 154(b) by 863 days.

(21) Appl. No.: 17/491,350

(22) Filed: Sep. 30, 2021

(65) Prior Publication Data

US 2023/0097140 A1 Mar. 30, 2023

(51) Int. Cl.
*A61B 34/10* (2016.01)
*A61B 17/17* (2006.01)
(Continued)

(52) U.S. Cl.
CPC .......... *A61B 34/10* (2016.02); *A61B 17/1778* (2016.11); *A61F 2/28* (2013.01);
(Continued)

(58) Field of Classification Search
CPC .............. A61B 34/10; A61B 2034/104; A61B 2034/105; A61B 2034/107;
(Continued)

(56) References Cited

U.S. PATENT DOCUMENTS 8,257,359 B2 * 9/2012 Burkhart ............ A61B 17/1796
606/87
8,551,177 B2 10/2013 DeWilde et al.
(Continued)

FOREIGN PATENT DOCUMENTS

| RU | 2747694 | 5/2021 |
|----|---------|--------|
| WO | 2019110531 | 6/2019 |
| WO | 2020236441 | 11/2020 |

OTHER PUBLICATIONS

Hamamoto, J.T., Leroux, MD, T., Chahla, MD., J., Bhatia, MD, S., Higgins, B.A., J.D., Romeo, MD, A.A., Yanke, MD, A.B., and Verma, MD, N.N. (2016). Assessment and evaluation of glenoid bone loss. Arthroscopy Techniques. vol. 5(4). Aug. 2016. pp. e947-e951.
(Continued)

*Primary Examiner* — Sameh R Boles
(74) *Attorney, Agent, or Firm* — Carlson, Gaskey & Olds, P.C.

(57) ABSTRACT

This disclosure relates to planning systems, methods and instrumentation. The planning systems, methods and instrumentation disclosed herein may be utilized for planning orthopaedic procedures to restore functionality to a joint, may include determining an amount of bone loss along or otherwise adjacent to an articular surface of a bone. Instrumentation may be formed based on one or more dimensions associated with the bone loss. The articular surface may be repaired, which may include utilizing the instrumentation and planning systems to position and secure a bone graft along a position of the bone associated with the bone loss.

28 Claims, 36 Drawing Sheets

(51) Int. Cl.
   *A61F 2/28* (2006.01)
   *A61F 2/46* (2006.01)
(52) U.S. Cl.
   CPC ... *A61B 2034/104* (2016.02); *A61B 2034/105* (2016.02); *A61B 2034/107* (2016.02); *A61B 2034/108* (2016.02); *A61F 2002/2835* (2013.01); *A61F 2002/4633* (2013.01)
(58) Field of Classification Search
   CPC . A61B 2034/108; A61B 17/1778; A61F 2/28; A61F 2002/2835; A61F 2002/4633
   See application file for complete search history.

(56) References Cited

U.S. PATENT DOCUMENTS

| | | | |
|---|---|---|---|
| 8,764,836 | B2 | 7/2014 | DeWilde et al. |
| 9,107,676 | B2 | 8/2015 | Burkhart et al. |
| 9,173,661 | B2 | 11/2015 | Metzger et al. |
| 9,301,812 | B2 | 4/2016 | Kehres et al. |
| 9,351,743 | B2 | 5/2016 | Kehres et al. |
| 9,451,973 | B2 | 9/2016 | Heilman et al. |
| 9,592,065 | B2 | 3/2017 | Gregory |
| 9,936,961 | B2 | 4/2018 | Heilman et al. |
| 10,172,627 | B2 | 1/2019 | Haberman et al. |
| 10,172,715 | B2 | 1/2019 | DeWilde et al. |
| 10,327,789 | B2 | 6/2019 | Bouduban et al. |
| 10,426,492 | B2 | 10/2019 | Metzger et al. |
| 10,426,493 | B2 | 10/2019 | Kehres et al. |
| 10,426,549 | B2 | 10/2019 | Kehres et al. |
| 10,806,472 | B2 | 10/2020 | Bettenga et al. |
| 10,842,510 | B2 | 11/2020 | Heilman et al. |
| 11,517,334 | B1 | 12/2022 | Jaramaz et al. |
| 2011/0160736 | A1* | 6/2011 | Meridew ............ A61B 17/152 606/89 |
| 2012/0130382 | A1* | 5/2012 | Iannotti ............... A61F 2/4603 606/87 |
| 2016/0242931 | A1 | 8/2016 | Wong et al. |
| 2017/0079803 | A1 | 3/2017 | Lang |
| 2017/0105841 | A1 | 4/2017 | Vanasse et al. |
| 2019/0099190 | A1 | 4/2019 | Haberman et al. |
| 2019/0125542 | A1 | 5/2019 | DeWilde et al. |
| 2019/0321058 | A1 | 10/2019 | Bouduban et al. |
| 2019/0365473 | A1 | 12/2019 | Kehres et al. |
| 2019/0374237 | A1 | 12/2019 | Metzger et al. |
| 2020/0046381 | A1 | 2/2020 | Kehres et al. |
| 2020/0197030 | A1 | 6/2020 | Berger et al. |
| 2020/0390453 | A1 | 12/2020 | Bettenga et al. |
| 2020/0405326 | A1 | 12/2020 | Bosworth |
| 2021/0038233 | A1 | 2/2021 | Heilman et al. |

OTHER PUBLICATIONS

Eichinger, MD., J.K. (2018). How should the surgeon treat shoulder instability with bone loss? International Congress for Joint Reconstruction: Ask the expert. Retrieved Jul. 14, 2021 from: https://icjr.net/articles/how-should-the-surgeon-treat-shoulder-instability-with-bone-loss.
Scapula. (2015). The Art of Medicine. Retrieved Jul. 13, 2021 from: https://theartofmed.wordpress.com/2015/06/01/scapula/.
International Search Report and Written Opinion for International Application No. PCT/US2022/044189 mailed Feb. 10, 2023.
International Preliminary Report on Patentability for International Application No. PCT/US2022/044189 mailed Apr. 11, 2024.

\* cited by examiner

ORTHOPAEDIC PLANNING SYSTEMS, INSTRUMENTATION AND METHODS OF REPAIR

BACKGROUND

This disclosure relates to orthopaedic procedures and, more particularly, to systems and methods for planning and implementing the repair of bone defects and restoration of functionality to a joint.

Many bones of the human musculoskeletal system include articular surfaces. The articular surfaces articulate relative to other bones to facilitate different types and degrees of joint movement. The articular surfaces can erode or experience bone loss over time due to repeated use or wear or may fracture as a result of a traumatic impact. These types of bone defects can cause joint instability and pain. Some techniques utilize a bone graft and/or implant to repair a defect adjacent the articular surfaces.

The bone deficiency may occur along an articular surface of a glenoid. The surgeon may utilize a Latarjet procedure to repair the defect. The procedure may include performing an osteotomy to harvest to a coracoid process and then positioning the harvested bone along the defect area.

SUMMARY

This disclosure relates to planning systems, methods and instrumentation. The planning systems, methods and instrumentation may be utilized for planning and implementing orthopaedic procedures to restore functionality to a joint, including determining an amount of bone loss adjacent an articular surface of a bone, forming instrumentation associated with the bone loss, and repairing the articular surface which may include securing a bone graft along a position of the bone associated with the bone loss.

A guide assembly for an orthopaedic procedure according to an implementation of the present disclosure includes, inter alia, a shell including a first shell portion and a second shell portion that may be dimensioned to abut the first shell portion in an assembled position. Each of the first and second shell portions may include a shell body extending between opposed end walls. A sidewall of the shell body may extend between the end walls. A recess may extends inwardly from the sidewall. The recesses of the first and second shell portions may cooperate to establish a cavity that may dimensioned according to a first patient-specific contour. The first and second shells may be dimensioned to capture a first portion of bone that may be associated with the first patient-specific contour within the cavity. The sidewall of the first shell portion may establish a first resection plane. One of the end walls of the first shell portion and one of the end walls of the second shell portion may cooperate to establish a second resection plane in the assembled position. The second resection plane may be transverse to the first resection plane.

A guide assembly for an orthopaedic procedure according to an implementation of the present disclosure includes, inter alia, a shell including a shell body and an outrigger that may extend outwardly from the shell body to a free end. The shell body may extend between opposed end walls. A sidewall of the shell body may extend between the end walls. A recess may extend inwardly from the sidewall to establish a cavity that may be dimensioned according to a first patient-specific contour. The shell body may be dimensioned to capture a first portion of bone that may be associated with the first patient-specific contour within the cavity. The sidewall of the shell body may establish a first resection plane. One of the end walls of the shell body may establish a second resection plane in the assembled position. The second resection plane may be transverse to the first resection plane. The free end of the outrigger may be dimensioned to contact an articular surface that may be associated with a second portion of bone.

A system for planning an orthopaedic procedure according to an implementation of the present disclosure includes, inter alia, a computing device including a processor coupled to a memory. The processor may be configured to execute a planning environment that may include a display module, a spatial module and a comparison module. The memory may be configured to store a shoulder model. The shoulder model may be associated with a shoulder of a patient. The display module may be configured to display the shoulder model in a graphical user interface. The spatial model may be configured to establish a vertical reference plane that may extend through a first position along a trigonum spinae, a second position along a glenoid face and a third position along an inferior angle of the shoulder model. The spatial model may be configured to establish a superior-inferior plane that may extend through the first and second positions. The superior-inferior plane may be oriented at a first angle relative to the vertical reference plane such that the superior-inferior plane may extend through a fourth position along a surface of a superior angle of the shoulder model. The spatial module may be configured to establish a best fit circle along the glenoid face of the shoulder model. A center of the best fit circle may be established along the superior-inferior plane. The spatial module may be configured to determine a total area established by the best fit circle. The spatial model may be configured to determine a bone loss area between a perimeter of the best fit circle and an anterior segment associated with a perimeter of the glenoid face. The comparison model may be configured to determine a bone loss ratio. The bone loss ratio may be defined as the bone loss area divided by the total area. The comparison model may be configured to generate a first indicator in response to the bone loss ratio meeting a first predefined threshold.

A method of performing an orthopaedic procedure according to an implementation of the present disclosure includes, inter alia, fabricating a guide assembly. The guide assembly may include a shell having a first shell portion and a second shell portion that may cooperate to establish a cavity. The cavity may be dimensioned according to a first patient-specific contour that may be associated with a coracoid process of a patient. A first sidewall of the first shell portion may establish a first resection surface. Adjacent end walls of the first and second shell portions may establish a second resection surface in an assembled position. The method may include moving the first and second shell portions together to capture a portion of the coracoid process in the cavity. The method may include removing the portion of the coracoid process to establish a bone graft in response to resecting the coracoid process along the second resection surface. The method may include removing a portion of the bone graft to establish a resection face in response to resecting the bone graft along the first resection surface.

A method of planning an orthopaedic procedure according to an implementation of the present disclosure includes, inter alia, establishing a vertical reference plane that may extend through an acromion process and a position along a trigonum spinae of a shoulder model in a planning environment. The shoulder model may be associated with a shoulder of a patient. The method may include establishing a superior-inferior plane that may extend through the position of the trigonum spinae. The superior-inferior plane may be oriented at a first angle relative to the vertical reference plane such that the superior-inferior plane may extend along a surface of a superior angle of the shoulder model. The method may include establishing a best fit circle along a glenoid face of the shoulder model. A center of the best fit circle may be established along the superior-inferior plane. The method may include determining a total area established by the best fit circle. The method may include determining a bone loss area between a perimeter of the best fit circle and an anterior segment associated with a perimeter of the glenoid face. The method may include determining a bone loss ratio. The bone loss ratio may be defined as the bone loss area divided by the total area. The method may include generating a first indicator associated with the bone loss ratio.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
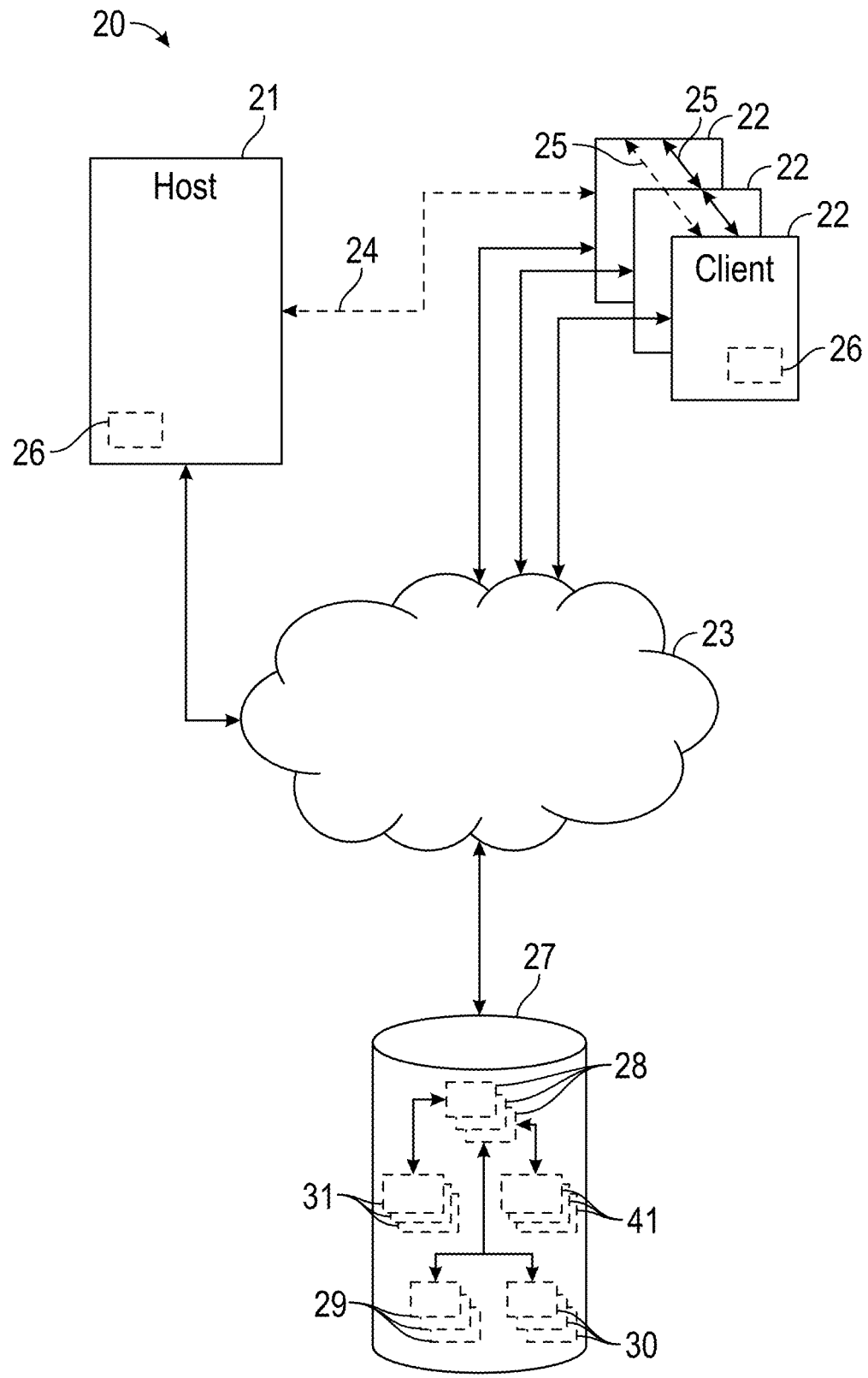
FIG. 1 illustrates an exemplary planning system.

This disclosure relates to surgical planning, systems and methods of repair. The planning systems described herein may be utilized for orthopaedic procedures and may be utilized to create, edit, execute and/or review surgical plans. The surgeon may utilize the planning systems pre-operatively, intra-operatively and/or post-operatively. The planning systems and method disclosed herein may include determining or inferring an amount of bone loss along an articular surface of a bone, such as bone loss along a glenoid. Aspects of the bone may be evaluated to establish one or more references, such as a superior-inferior line. The superior-inferior line may be established based on evaluating the bone to infer a position and orientation of a superior-inferior line associated with the bone prior to the bone loss. The superior-inferior line may be consistently established for different patient anatomy. The surgeon may utilize the superior-inferior line with various measurement techniques, including positioning a best fit circle along the articular surface, which may be used to accurately determine a size and position of the bone loss.

One or more dimensions associated with the bone loss may be determined and may relate to one or more patient-specific contours. The dimensions may be utilized to fabricate guide assemblies and other instrumentation, which may be used to form a bone graft and repair the articular surface with the bone graft. The instrumentation may include one or more features for precisely shaping the bone graft. The bone graft may be utilized in a Latarjet procedure to repair the articular surface. The instrumentation may be utilized in a coracoid osteotomy to harvest the bone graft. The planning system and instrumentation may be utilized to precisely position the bone graft, which may improve mobility and healing of the patient.

A guide assembly for an orthopaedic procedure according to an implementation of the present disclosure includes, inter alia, a shell including a first shell portion and a second shell portion that may be dimensioned to abut the first shell portion in an assembled position. Each of the first and second shell portions may include a shell body extending between opposed end walls. A sidewall of the shell body may extend between the end walls. A recess may extends inwardly from the sidewall. The recesses of the first and second shell portions may cooperate to establish a cavity that may dimensioned according to a first patient-specific contour. The first and second shells may be dimensioned to capture a first portion of bone that may be associated with the first patient-specific contour within the cavity. The sidewall of the first shell portion may establish a first resection plane. One of the end walls of the first shell portion and one of the end walls of the second shell portion may cooperate to establish a second resection plane in the assembled position. The second resection plane may be transverse to the first resection plane.

In a further implementation, the sidewall of the first shell portion and the sidewall of the second shell portion may be dimensioned to abut each other to encircle the cavity in the assembled position.

In a further implementation, a first depth may be established between a floor of the recess and the sidewall of the first shell portion. The first depth may be associated with a dimension of a second portion of bone.

In a further implementation, an outrigger may include a main body that may extend outwardly from the first shell portion to a free end. The free end may be dimensioned to contact an articular surface associated with the second portion of bone.

In a further implementation, the outrigger may extend transversely from the first shell portion such that the second shell portion may be positioned between the sidewall of the first shell portion and the free end of the outrigger in the assembled position.

In a further implementation, the outrigger may be dimensioned according to a second patient-specific contour that may be associated with the articular surface.

In a further implementation, the first patient-specific contour may be associated with a coracoid process. The second patient-specific contour may be associated with the articular surface of a glenoid.

In a further implementation, the sidewall of the first shell portion may be dimensioned to abut an anterior surface of a glenoid in response to contact between the free end of the outrigger and the articular surface.

In a further implementation, the first shell portion may include a first passage. The second shell portion may include a second passage. The first and second passages may be substantially aligned in the assembled position such that a drill bit may be insertable through the first and second passages and across the cavity.

In a further implementation, the first patient-specific contour may be associated with a coracoid process.

A guide assembly for an orthopaedic procedure according to an implementation of the present disclosure includes, inter alia, a shell including a shell body and an outrigger that may extend outwardly from the shell body to a free end. The shell body may extend between opposed end walls. A sidewall of the shell body may extend between the end walls. A recess may extend inwardly from the sidewall to establish a cavity that may be dimensioned according to a first patient-specific contour. The shell body may be dimensioned to capture a first portion of bone that may be associated with the first patient-specific contour within the cavity. The sidewall of the shell body may establish a first resection plane. One of the end walls of the shell body may establish a second resection plane in the assembled position. The second resection plane may be transverse to the first resection plane. The free end of the outrigger may be dimensioned to contact an articular surface that may be associated with a second portion of bone.

In a further implementation, a first depth may be established between a floor of the recess and the sidewall of the shell body. The first depth may be associated with a dimension of a second portion of bone.

In a further implementation, the free end of the outrigger may be dimensioned according to a second patient-specific contour that may be associated with the articular surface.

In a further implementation, the first patient-specific contour may be associated with a coracoid process. The second patient-specific contour may be associated with the articular surface of a glenoid.

A system for planning an orthopaedic procedure according to an implementation of the present disclosure includes, inter alia, a computing device including a processor coupled to a memory. The processor may be configured to execute a planning environment that may include a display module, a spatial module and a comparison module. The memory may be configured to store a shoulder model. The shoulder model may be associated with a shoulder of a patient. The display module may be configured to display the shoulder model in a graphical user interface. The spatial model may be configured to establish a vertical reference plane that may extend through a first position along a trigonum spinae, a second position along a glenoid face and a third position along an inferior angle of the shoulder model. The spatial model may be configured to establish a superior-inferior plane that may extend through the first and second positions. The superior-inferior plane may be oriented at a first angle relative to the vertical reference plane such that the superior-inferior plane may extend through a fourth position along a surface of a superior angle of the shoulder model. The spatial module may be configured to establish a best fit circle along the glenoid face of the shoulder model. A center of the best fit circle may be established along the superior-inferior plane. The spatial module may be configured to determine a total area established by the best fit circle. The spatial model may be configured to determine a bone loss area between a perimeter of the best fit circle and an anterior segment associated with a perimeter of the glenoid face. The comparison model may be configured to determine a bone loss ratio. The bone loss ratio may be defined as the bone loss area divided by the total area. The comparison model may be configured to generate a first indicator in response to the bone loss ratio meeting a first predefined threshold.

In a further implementation, the first angle may be approximately 20 degrees.

In a further implementation, the comparison module may be configured to generate a second indicator in response to the bone loss ratio meeting a second predefined threshold. The second predefined threshold may be greater than the first predefined threshold.

In a further implementation, the fourth position may substantially correspond to an intersection of projections of the surface of the superior angle and a superior segment of a glenoid rim of the shoulder model onto a common plane.

In a further implementation, the display module may be configured to display a transparency of the shoulder model in the graphical user interface. The transparency may include the glenoid face overlaying the trigonum spinae and the glenoid face overlaying a portion of the superior angle.

In a further implementation, the spatial module may be configured to generate a hemispherical object having a zenith that may be positioned adjacent to the glenoid face of the shoulder model. The spatial module may be configured to fit a boundary of the hemispherical object relative to a curvature of the glenoid face of the shoulder model. The spatial module may be configured to position a bone graft model in a first volume that may be associated with the bone loss area such that a boundary of the bone graft model may be substantially aligned with the boundary of the hemispherical object at a boundary point.

In a further implementation, the bone graft model may be associated with a coracoid process of the shoulder model.

In a further implementation, the display module may be configured to display the bone graft model in the first volume.

In a further implementation, the spatial module may be configured to generate a guide assembly model. The comparison module may be configured to generate one or more dimensions that may be associated with the guide assembly model based on the bone loss area.

In a further implementation, the bone graft model may be associated with a coracoid process of the shoulder model. The guide assembly model may include a shell having a first shell portion and a second shell portion that may cooperate to establish a cavity in an assembled position. The cavity may be dimensioned according to a contour of the coracoid process of the shoulder model. A first sidewall along the first shell portion may establish a first resection plane. Adjacent end walls of the first and second shell portions may establish a second resection plane in the assembled position. The second resection plane may be transverse to the first resection plane.

In a further implementation, the guide assembly model may include an outrigger that may extend outwardly from the first shell portion to a free end. The free end may be dimensioned to contact the glenoid face of the shoulder model according to the one or more dimensions.

In a further implementation, the one or more dimensions may include a first dimension, a second dimension and a third dimension. The first dimension may be associated with a width of the bone loss area. The first resection plane may be established with respect to the first dimension. The second dimension may be associated with a length of the bone loss area between ends of the anterior segment. The second resection plane may be established with respect to the second dimension. The third dimension may be associated with a height of the boundary point relative to a point along the curvature of the glenoid face of the shoulder model. A position of the free end of the outrigger relative to the cavity may be established with respect to the third dimension.

A method of performing an orthopaedic procedure according to an implementation of the present disclosure includes, inter alia, fabricating a guide assembly. The guide assembly may include a shell having a first shell portion and a second shell portion that may cooperate to establish a cavity. The cavity may be dimensioned according to a first patient-specific contour that may be associated with a coracoid process of a patient. A first sidewall of the first shell portion may establish a first resection surface. Adjacent end walls of the first and second shell portions may establish a second resection surface in an assembled position. The method may include moving the first and second shell portions together to capture a portion of the coracoid process in the cavity. The method may include removing the portion of the coracoid process to establish a bone graft in response to resecting the coracoid process along the second resection surface. The method may include removing a portion of the bone graft to establish a resection face in response to resecting the bone graft along the first resection surface.

In a further implementation, the method may include removing the second shell portion from the first shell portion. The method may include positioning the first resection surface of the first shell portion in opposition with an anterior surface of a glenoid such that the resection surface of the bone graft may abut the anterior surface of the glenoid at a predetermined height.

In a further implementation, the method may include moving a guide pin through a first passage in the first shell portion, then through the bone graft in the cavity, and then into the anterior surface of the glenoid at an insertion point. The method may include securing the bone graft with one at least one fastener at the insertion point.

In a further implementation, the fabricating step may include forming an outrigger that may extend outwardly from the first shell portion to a free end. The free end may be dimensioned to contact a glenoid face of a glenoid. The method may include positioning the free end of the outrigger in abutment with the glenoid face such that the resection face of the bone graft may abut an anterior surface of the glenoid at a predetermined height relative to the glenoid face.

In a further implementation, the step of positioning the free end of the outrigger may occur such that the first resection surface abuts the anterior surface of the glenoid. The method may include moving a guide pin through a first passage in the first shell portion, then through the bone graft in the cavity, and then into the anterior surface of the glenoid at an insertion point that may be associated with the predetermined height.

In a further implementation, the step of positioning the free end of the outrigger may occur such that a portion of the bone graft may be lateral of the glenoid face during the step of moving the guide pin into the anterior surface of the glenoid.

In a further implementation, the first resection surface may be dimensioned with respect to a width of a second patient-specific contour. The second patient-specific contour may be established by a bone loss area that may be bounded by an anterior segment associated with a glenoid face of the patient.

In a further implementation, the second resection surface may be dimensioned with respect to a length of the bone loss area between ends of the anterior segment.

A method of planning an orthopaedic procedure according to an implementation of the present disclosure includes, inter alia, establishing a vertical reference plane that may extend through a first position along a trigonum spinae, a second position along a glenoid face and a third position along an inferior angle of a shoulder model in a planning environment. The shoulder model may be associated with a shoulder of a patient. The method may include establishing a superior-inferior plane that may extend through the first and second positions. The superior-inferior plane may be oriented at a first angle relative to the vertical reference plane such that the superior-inferior plane may extend through a fourth position along a surface of a superior angle of the shoulder model. The method may include establishing a best fit circle along the glenoid face of the shoulder model. A center of the best fit circle may be established along the superior-inferior plane. The method may include determining a total area established by the best fit circle. The method may include determining a bone loss area between a perimeter of the best fit circle and an anterior segment associated with a perimeter of the glenoid face. The method may include determining a bone loss ratio. The bone loss ratio may be defined as the bone loss area divided by the total area. The method may include generating a first indicator associated with the bone loss ratio.

In a further implementation, the method may include displaying the shoulder model in a graphical user interface of the planning environment such that each of the superior-inferior plane and the vertical reference plane may intersect two respective points along the perimeter of the glenoid face.

In a further implementation, the step of displaying the shoulder model may include displaying a transparency of the shoulder model in the graphical user interface. The transparency may include the glenoid face overlaying the trigonum spinae and the glenoid face overlaying a portion of the superior angle.

In a further implementation, the method may include fitting a curvature of a hemispherical object relative to a curvature of the glenoid face of the shoulder model. The method may include displaying the hemispherical object relative to the glenoid face of the shoulder model which may occur subsequent to the fitting step. The method may include positioning a bone graft model in a first volume that may be associated with the bone loss area such that a boundary of the bone graft model may be substantially aligned with the curvature of the hemispherical object at a boundary point.

In a further implementation, the bone graft model may be associated with a coracoid process of the shoulder model.

In a further implementation, the method may include generating a guide assembly model in the planning environment. The method may include generating one or more dimensions that may be associated with the guide assembly model based on the bone loss area.

In a further implementation, the method may include fabricating the guide assembly according to the guide assembly model.

In a further implementation, the guide assembly may include a shell having a first shell portion and a second shell portion that may cooperate to establish a cavity in an assembled position. The cavity may be dimensioned according to a first patient-specific contour that may be associated with a coracoid process of the patient. The first and second shell portions may be dimensioned to capture a portion of the coracoid process in the cavity in the assembled position.

In a further implementation, the step of determining the bone loss area may include determining a width of the bone loss area. A first sidewall along the first shell portion may establish a first resection surface. The first resection surface may be dimensioned with respect to the determined width of the bone loss area.

In a further implementation, the method may include the step of determining the bone loss area may include determining a length of the bone loss area between ends of the anterior segment. Adjacent end walls of the first and second shell portions may be dimensioned to establish a second resection surface in the assembled position. The second resection surface may be dimensioned with respect to the determined length of the bone loss area.

FIG. 1 illustrates an exemplary planning system 20 that may be utilized for planning surgical procedures. The system 20 may be used for planning orthopaedic procedures, including pre-operatively, intra-operatively and/or post-operatively to create, edit, execute and/or review surgical plans.

The system 20 may include a host computer 21 and one or more client computers 22. The host computer 21 may be configured to execute one or more software programs. In some implementations, the host computer 21 is more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network, for example.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may, for example, include UVPROM, EEPROM, FLASH, RAM, ROM, DVD, CD, a hard drive, or other computer readable medium which may store data and/or other information relating to the planning techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. The client computers 22 may be configured to execute one or more software programs, such as various surgical tools. The planning package may be configured to communicate with the host computer 21 either over the network 23 or directly through the direct client interface 24. In another implementation, the client computers 22 are configured to communicate with each other directly via a peer-to-peer interface 25.

Each client computer 22 may be operable to access and locally and/or remotely execute a planning environment 26. The planning environment 26 may be a standalone software package or may be incorporated into another surgical tool. The planning environment 26 may provide a display or visualization of one or more bone models, graft models, assembly models and related images via one or more graphical user interfaces (GUI). Each bone model, graft model and assembly model, images and other information may be stored in one or more files or records according to a specified data structure.

The system 20 may include at least one storage system 27, which may be operable to store or otherwise provide data to other computing devices. The storage system 27 may be a storage area network device (SAN) configured to communicate with the host computer 21 and/or the client computers 22 over the network 23. In implementations, the storage system 27 may be incorporated within or directly coupled to the host computer 21 and/or client computers 22. The storage system 27 may be configured to store one or more of computer software instructions, data, database files, configuration information, etc.

In implementations, the system 20 is a client-server architecture configured to execute computer software on the host computer 21, which is accessible by the client computers 22 using either a thin client application or a web browser executing on the client computers 22. The host computer 21 may load the computer software instructions from local storage, or from the storage system 27, into memory and may execute the computer software using the one or more computer processors.

The system 20 may include one or more databases 28. The databases 28 may be stored at a central location, such as the storage system 27. In another implementation, one or more databases 28 may be stored at the host computer 21 and/or may be a distributed database provided by one or more of the client computers 22. Each database 28 may be a relational database configured to associate one or more bone models 29, one or more graft models 30 and/or one or more assembly models 41 to each other and/or a surgical plan 31. Each surgical plan 31 may be associated with a respective patient. Each bone model 29, graft model 30, assembly model 41 and surgical plan 31 may be assigned a unique identifier or database entry. The database 28 may be configured to store data corresponding to the bone models 29, graft models 30, assembly models 41 and surgical plans 31 in one or more database records or entries, and/or may be configured to link or otherwise associate one or more files corresponding to each respective bone model 29, graft model 30, assembly model 41 and surgical plan 31. Bone models 29, graft models 30 and/or assembly models 41 stored in the database(s) 28 may correspond to respective patient anatomies from prior surgical cases, and may be arranged into one or more predefined categories such as sex, age, ethnicity, defect category, procedure type, etc.

Each bone model 29 and graft model 30 may include information obtained from one or more medical devices or tools, such as a computerized tomography (CT), magnetic resonance imaging (MRI) machine and/or X-ray machine, that obtains one or more images of a patient. The bone model 29 and graft model 30 may include one or more digital images and/or coordinate information relating to an anatomy of the patient obtained or derived from the medical device (s). The graft model 30 may include a portion of the geometry of the bone model 29 or may include separate and distinct geometry associated with another bone. Each assembly model 41 may include coordinate information associated with a predefined design. The planning environment 26 may incorporate and/or interface with one or more modeling packages, such as a computer aided design (CAD) package, to render the models 29, 30, 41 as two-dimensional (2D) and/or three-dimensional (3D) volumes or constructs.

The predefined design may correspond to one or more components. The assembly models 41 may correspond to instrumentation, devices and components of various shapes and sizes. Each assembly may include one or more components that may be situated at a surgical site, such as guides and fasteners. Each assembly model 41 may correspond to a single component or may include two or more components that may be configured to establish an assembly. Each bone model 29, graft model 30 and assembly model 41 may correspond to 2D and/or 3D geometry, and may be utilized to generate a wireframe, mesh and/or solid construct in a display.

Each surgical plan 31 may be associated with one or more bone models 29, graft models 30 and/or assembly models 41. The surgical plan 31 may include one or more revisions to the bone model 29, graft model 30 and/or assembly model 41 and may include information relating to a position of a graft model 30 and/or assembly model 41 relative to the original and/or revised bone model 29. The surgical plan 31 may include coordinate information relating to the revised bone model 29, graft model 30 and/or assembly model 41 and a relative position of the models 29, 30, 41 in predefined data structure(s). Revisions to each model 29, 30, 41 and surgical plan 31 may be stored in the database 28 automatically and/or in response to user interaction with the system 20.

One or more surgeons, assistants and other users may be provided with a planning environment 26 via the client computers 22 and may simultaneously access each bone model 29, graft model 30, assembly model 41 and surgical plan 31 stored in the database(s) 28. Each user may interact with the planning environment 26 to create, view and/or modify various aspects of the surgical plan 31. Each client computer 22 may be configured to store local instances of the bone models 29, graft models 30, assembly models 41 and/or surgical plans 31, which may be synchronized in real-time or periodically with the database(s) 28. The planning environment 26 may be a standalone software package executed on a client computer 22 or may be provided as one or more services executed on the host computer 21, for example.

Figure 2:
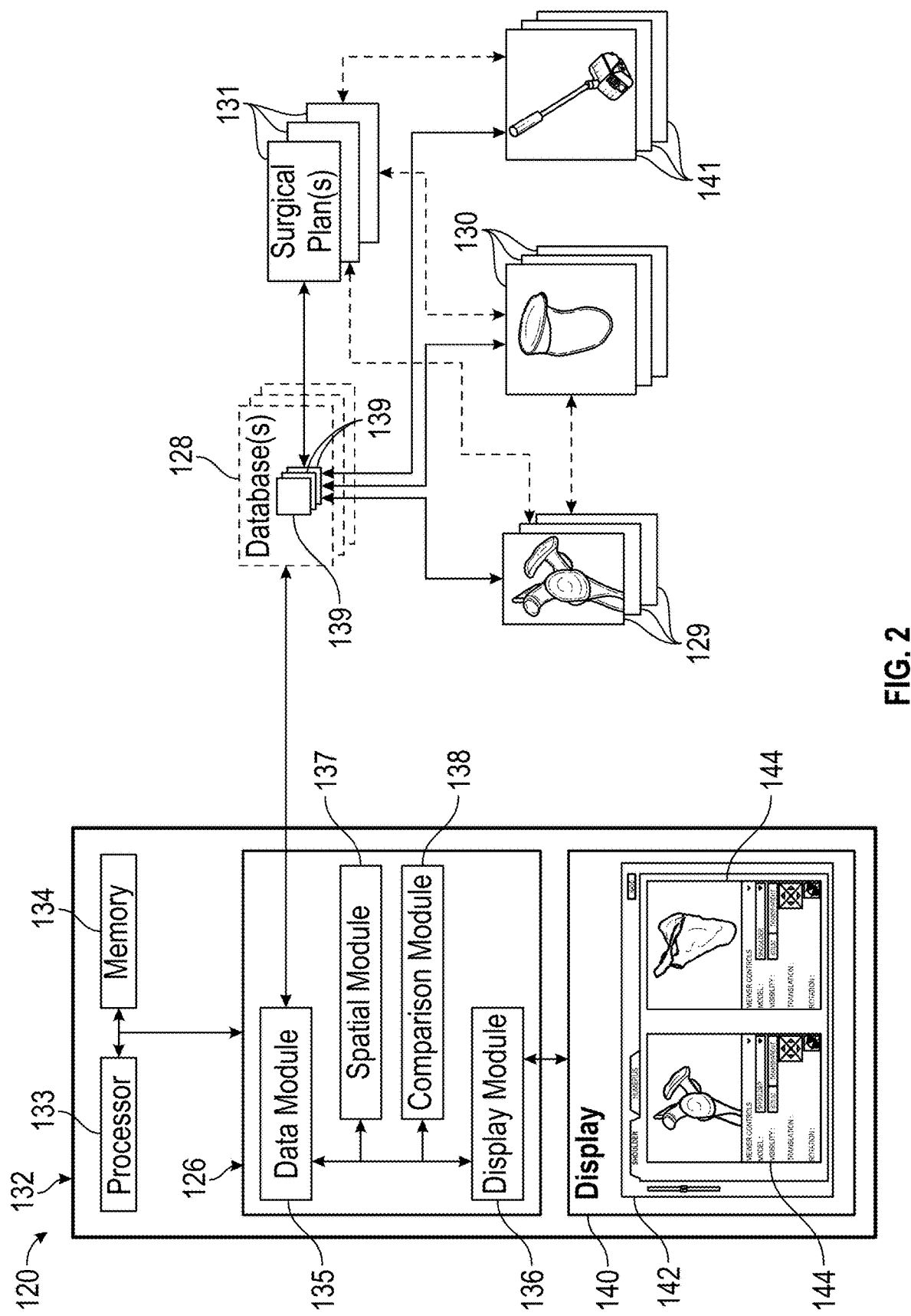
FIG. 2 illustrates another exemplary planning system including a user interface.

FIG. 2 illustrates an exemplary planning system 120 for planning a surgical procedure. The system 120 may be utilized to plan and implement various orthopaedic and other surgical procedures, such as an arthroplasty to repair a joint. The system 120 may be utilized in planning a resection of one or more bones, including harvesting bones to establish bone grafts for repairing joints. The planning system 120 may be utilized in planning a Latarjet procedure to restore stability to a shoulder joint, which may address bone loss along a perimeter of a glenoid and an associated risk of dislocation and pain. The planning system 120 may be utilized in planning the harvesting or resection of a coracoid process of a patient for use in a Latarjet procedure. Although the planning systems and methods disclosed herein primarily refer to repair of a shoulder, it should be understood that the planning system 120 may be utilized in the repair of other locations of the patient and other surgical procedures including repair of other joints such as an ankle, wrist, hand, hip or knee, and including repair of fractures.

The system 120 may include a computing device 132 including at least one processor 133 coupled to memory 134. The computing device 132 can include any of the computing devices disclosed herein, including the host computer 21 and/or client computer 22 of FIG. 1. The processor 133 may be configured to execute a planning environment 126 for creating, editing, executing and/or reviewing one or more surgical (e.g., pre-operative) plans 131 during pre-operative, intra-operative and/or post-operative phases of a surgery and for generating one or more models or designs that may be utilized to fabricate various guides and other assemblies, including any of the assemblies disclosed herein.

The planning environment 126 may include at least a data module 135, a display module 136, a spatial module 137 and a comparison module 138. Although four modules are shown, it should be understood that fewer or more than four modules may be utilized and/or one or more of the modules may be combined to provide the disclosed functionality.

The data module 135 may be configured to access, retrieve and/or store data and other information in the database(s) 128 corresponding to one or more bone model(s) 129, graft model(s) 130, assembly model(s) 141 and/or surgical plan(s) 131. The data and other information may be stored in one or more databases 128 as one or more records or entries 139. In implementations, the data and other information may be stored in one or more files that are accessible by referencing one or more objects or memory locations referenced by the records or entries 139. The data module 135 may be configured to execute one or more system commands to communicate the data and other information.

The memory 134 may be configured to access, load, edit and/or store instances of one or more bone models 129, graft models 130, assembly models 141 and/or surgical plans 131 in response to one or more commands from the data module 135. The data module 135 may be configured to cause the memory 134 to store a local instance of the bone model(s) 129, graft model(s) 130, assembly model(s) 141 and/or surgical plan(s) 131 which may be synchronized with records 139 in the database(s) 128. Exemplary bone models 129 may include one or more bones associated with a joint, such as a shoulder model associated with a shoulder of a patient.

The display module 136 may be configured to display data and other information relating to one or more surgical plans 131 in at least one graphical user interface (GUI) 142, including the bone model(s) 129, graft model(s) 130, assembly model(s) 141 and/or aspects of the surgical plan(s) 131. The computing device 132 may be coupled to a display device 140. The display module 136 may be configured to cause the display device 140 to display information in the user interface 142. The display module 136 may be configured to execute one or more system commands to display the data and other information. A surgeon or other user may interact with the user interface 142 via the planning environment 126 to create, edit, execute and/or review one or more surgical plans 131.

Figure 3:
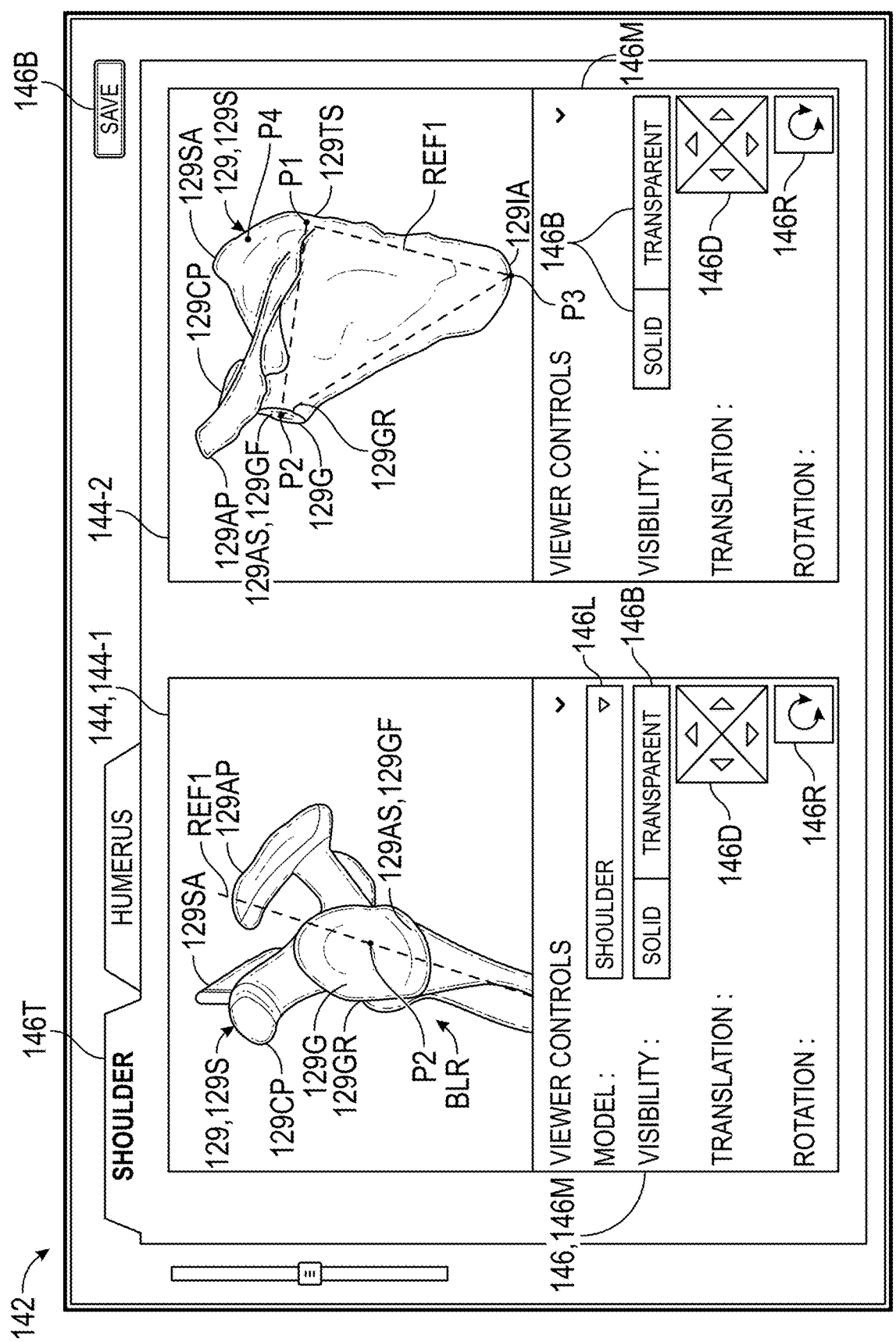
FIG. 3 illustrates the user interface of FIG. 2 including different views of a bone model.

Referring to FIG. 3, with continuing reference to FIG. 2, the user interface 142 may include one or more display windows 144 and one or more objects 146. The objects 146 may include graphics such as menus, tabs and buttons accessible by user interaction, such as tabs 146T, buttons 146B, drop-down lists 146L, menus 146M, entry fields 146E (e.g., FIG. 4), directional indicators 146D, 146R and graphics 146G (see, e.g., FIGS. 7A-7B). Geometric objects including selected bone model(s) 129, graft model(s) 130 (see, e.g., FIGS. 9-10), and assembly model(s) 141 (see, e.g., FIG. 15) and other information relating to the surgical plan 131 may be displayed in one or more of the display windows 144.

The display module 136 may be configured to display one or more selected bone models 129, graft models 130 and/or assembly models 141 in the display windows 144. The display module 136 may be configured such that the selected bone model(s) 129, graft model(s) 130 and/or assembly model(s) 141 may be selectively displayed and hidden (e.g., toggled) in one or more of the display windows 144 in response to user interaction with the user interface 142, which may provide the surgeon with enhanced flexibility in reviewing aspects of the surgical plan 131.

The data module 135 may be configured to access the bone model 129 from the database 128, which may occur automatically or in response to user interaction with the user interface 142. The data module 135 may be configured to store an instance of the selected bone model 129 in the memory 134. The bone model 129 may be associated with a joint. For example, the bone model 129 may be a shoulder model 129S associated with a shoulder establishing a shoulder joint of a patient. The display module 136 may be configured to display the selected bone model 129 in at least one of the display windows 144 of the user interface 142. The shoulder model 129S may include a glenoid 129G including a glenoid face 129GF and glenoid rim 129GR, an acromion process 129AP, a coracoid process 129CP, a superior angle 129SA, a trigonum spinae 129TS, and an inferior angle 129IA. The inferior angle 129IA may establish an inferior-most position (e.g., tip) of the shoulder model 129SA.

The display windows 144 may include first and second display windows 144-1, 144-2. Although a particular number of display windows 144 are illustrated, it should be understood that the user interface 142 may be configured with any number of display windows 144 in accordance with the teachings disclosed herein, and aspects of the display windows 144 may be combined or separated. The display windows 144-1, 144-2 may be configured to display a two-dimensional (2D) and/or three-dimensional (3D) representation of the selected bone models 129. The first display window 144-1 may be configured to display a lateral view of the glenoid face 129GF, and the second window 144-1 may be configured to display a posterior view of the shoulder model 129S, including the glenoid 129G. The surgeon or assistant may interact with the menus 146M, directly with the display windows 144-1, 144-2, or with another portion of the user interface 142 to move the selected bone model 129 in 2D space (e.g., up, down, left, right) and/or 3D space (e.g., rotation, tilt, zoom, etc.), which may occur in response to interaction with the directional indicators 146D, 146R.

The selected bone model 129 may include an articular surface 129AS associated with an articular surface of a bone having an amount of bone loss or erosion. The bone loss may reside in a bone loss region BLR. The bone loss region BLR may reside along or may otherwise be adjacent to a perimeter of the articular surface 129AS, such as the glenoid rim 129GR, as illustrated in the display window 144-1.

Figure 4:
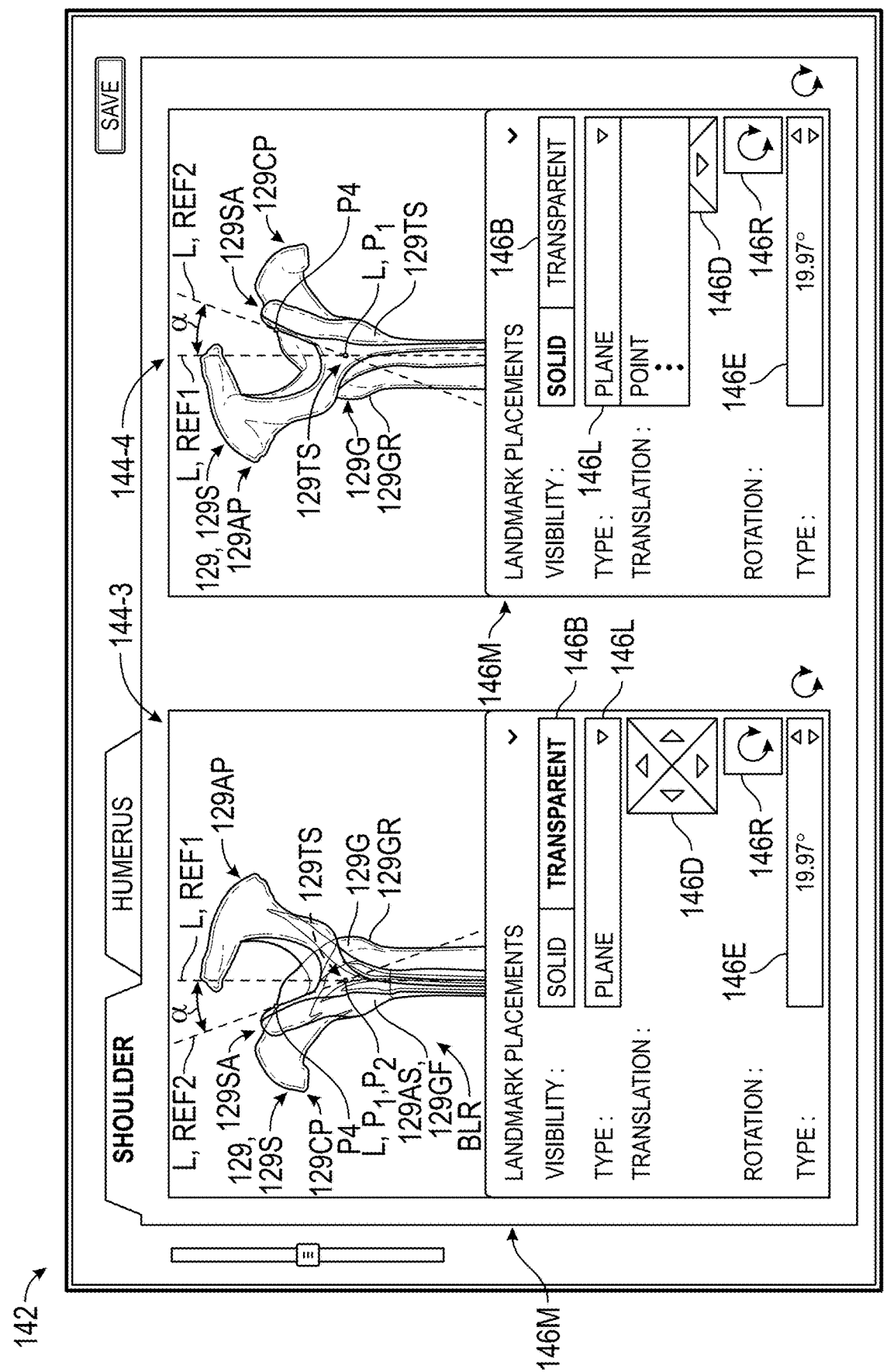
FIGS. 4-5 illustrate the user interface of FIG. 2 including landmarks associated with views of the bone model of FIG. 3.

Referring to FIG. 4, with continuing reference to FIGS. 2-3, the system 120 may be configured to determine or otherwise approximate an amount of bone loss associated with an articular surface of a bone corresponding to the selected bone model 129, such as bone loss associated with the bone loss region BLR. The display windows 144 may include third and fourth display windows 144-3, 144-4 configured to display various views of the selected bone model 129.

Figure 5:
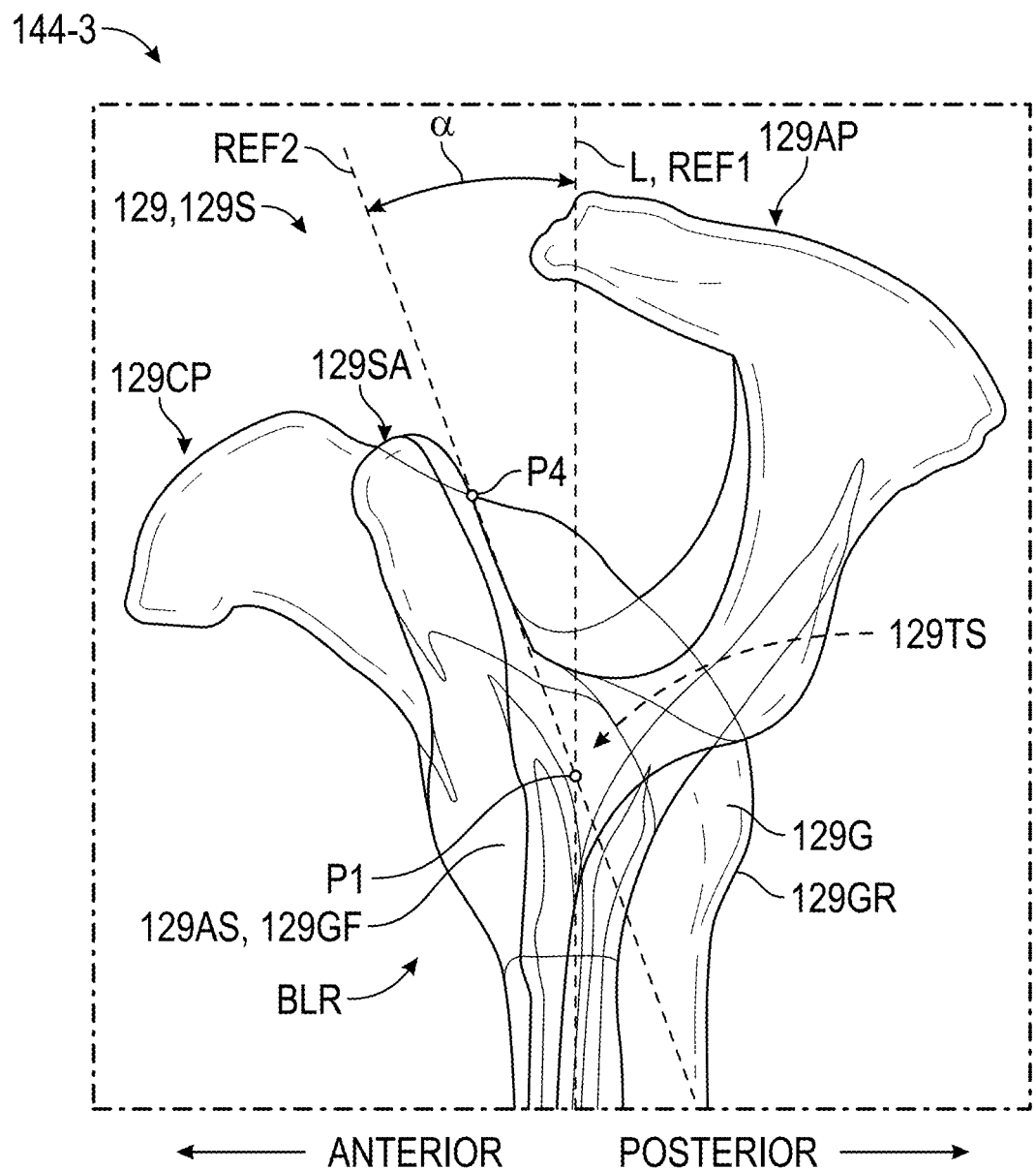

The third display window 144-3 may be configured to display a lateral (e.g., frontside) view of the glenoid face 129GF (see also FIG. 5). The fourth display window 144-4 may be configured to display a medial (e.g., backside) view of the trigonum spinae 129TS. The display module 136 may be configured to cause the display of a transparency of the shoulder model 129S in the display window 144-3 of the user interface 142, which may occur automatically or in response to selection of one of the buttons 146B of the associated menu 146M. The transparency may include at least the glenoid face 129GF overlaying the trigonum spinae 129TS and the glenoid face 129GF overlaying a portion of the superior angle 129SA.

The surgeon or assistant may interact with the menus 146M, directly with the display windows 144-3, 144-4, or with another portion of the user interface 142 to associate one or more landmarks L with the selected bone model 129. The landmarks L may include one or more points (e.g., positions) P along the anatomy, including points P1-P4 (see also FIG. 3) and one or more reference planes (e.g., REF1, REF2). The landmarks L may be generated automatically by the spatial module 137 and/or in response to user interaction with the user interface 142. In implementations, the spatial module 137 may be configured to determine one or more landmarks L based on evaluating a profile of the selected bone model 129. The spatial module 137 may be configured with logic to determine the landmarks L, such as edge detection and other image recognition techniques. The profile can be compared to one or more profiles of representative bones in the database 128.

The spatial module 137 may be configured to establish a first (e.g., vertical) reference plane REF1. The reference plane REF1 may be established along a "plane of the scapular." The plane of the scapular is generally known, but utilizing the plane of the scapular in combination with the techniques disclosed herein is not known. Point P1 may be established along the trigonum spinae 129TS of the shoulder model 129S. The spatial module 137 may be configured to establish the point P2 by projecting the point P1 laterally onto the articular surface 129AS of the glenoid 129G. Point P3 may be established along the inferior-most position (e.g., tip) of the inferior angle 129IA of the shoulder model 129SA (FIG. 3). The first reference plane REF1 may extend through the points P1-P3 along. The first reference plane REF1 may extend through or may be offset from the acromion process 129AP. The first reference plane REF1 may be established in response to user interaction with the user interface 142 and/or may be established in response to establishing the points P1, P3. The point P1 may be established at an approximate center of a face of the trigonum spinae 129TS. The point P2 may be established at an approximate center of the articular surface 129AS or glenoid face 129GF. The point P3 may be aligned vertically with the point P1.

The spatial model 137 may be configured to establish a second (e.g., superior-inferior) reference plane REF2. The second reference plane REF2 may extend through the points P1, P3 of the trigonum spinae 129TS and articular surface 129AS and may extend through the point P4 such that the second reference plane REF2 may be substantially transverse to the first reference plane REF1. The reference plane REF2 may be established in response to user interaction with the user interface 142 and/or may be established in response to establishing the points P1, P4. The second reference plane REF2 may be oriented at a (e.g., first) angle α relative to the first reference plane REF1 such that the second reference plane REF2 extends along a surface of the superior angle 129SA of the shoulder model 129S, which may be established at the point P4. In implementations, the point P4 may be substantially vertically aligned with the glenoid rim 129GR (see, e.g., FIG. 5). The point P4 may be established at a position along the superior angle 129SA that substantially corresponds to an intersection of the projections of the surface of the superior angle 129SA and a superior segment of the glenoid rim 129GR onto a common (e.g., lateral) plane, as illustrated by FIG. 5.

Various techniques may be utilized to establish the angle α between the reference planes REF1, REF2. The user may interact with the entry field 146E to specify a value of the angle α. A position and orientation of the second reference plane REF2 may be established automatically in response to specifying the first reference plane REF1. The angle α may be established automatically in response to specifying the reference planes REF1, REF2. Various values of the angle α may be utilized. The angle α may be an acute angle. In implementations, the angle α may be approximately 19-22 degrees, or more narrowly approximately 20 degrees, such as 19.97 degrees. For the purposes of this disclosure, the terms "substantially," "approximately" and "about" mean±3 percent of the stated value or relationship unless otherwise stated.

The display module 136 may be configured to display a projection of the first and second reference planes REF1, REF2 from the medial side of the shoulder model 129S to the lateral side of the shoulder model 129S, as illustrated by the display window 144-3. The reference planes REF1, REF2 may intersect the articular surface 129AS. The angle α may be established such that each of the first and second reference planes REF1, REF2 intersects two respective points along a perimeter of the glenoid face 129GF (see, e.g., display window 144-3). The perimeter of the glenoid face 129GF may be established by the glenoid rim 129GR and the bone loss region BLR.

Figure 6:
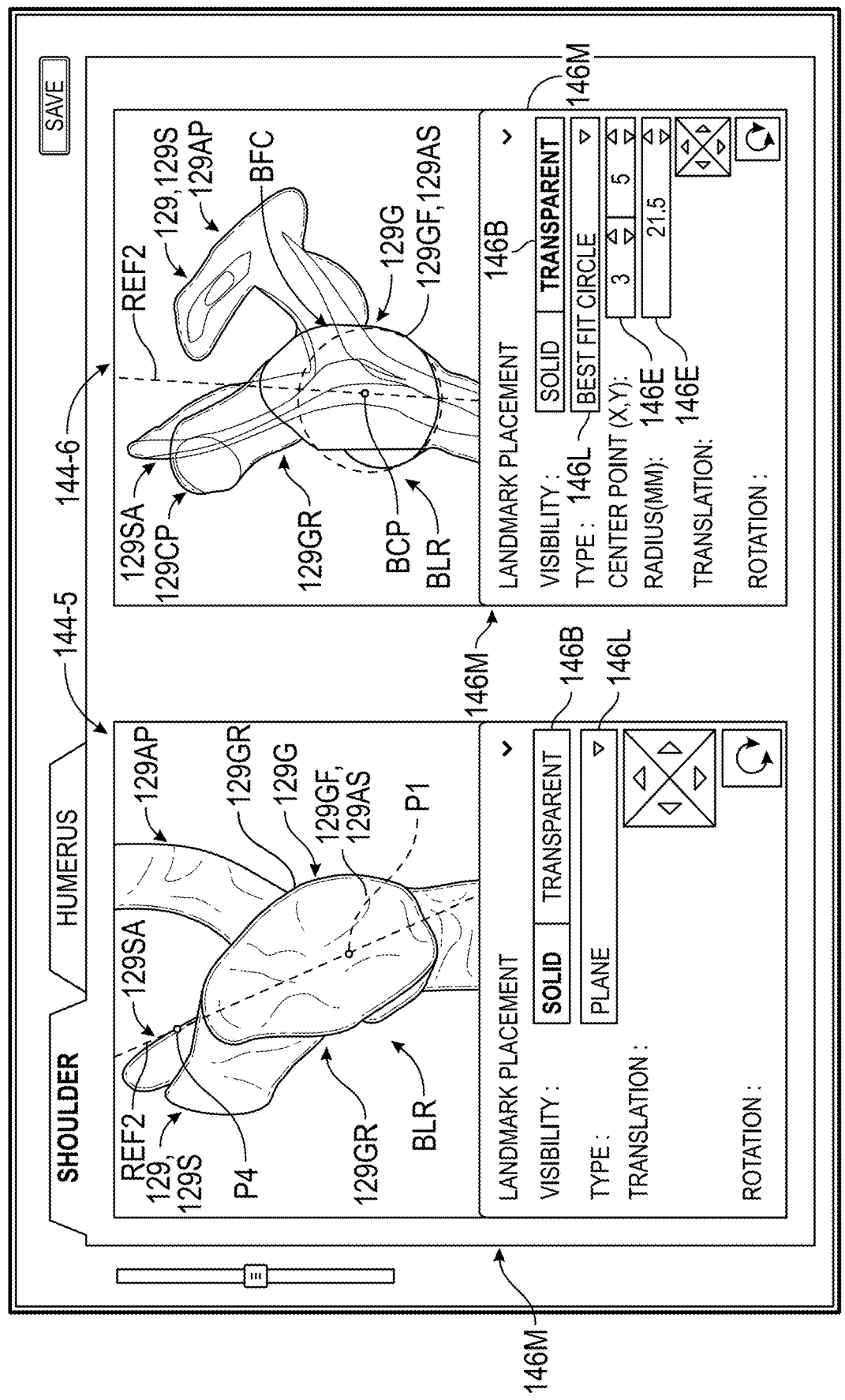
FIG. 6 illustrates a best fit circle positioned relative to a bone loss region of the bone model of FIG. 3.

Referring to FIG. 6, with continuing reference to FIGS. 2 and 4-5, the display windows 144 may include fifth and sixth display windows 144-5, 144-6. The fifth display window 144-5 may be configured to display a solid, lateral view of the articular surface 129AS, such as the glenoid face 129GF, the bone loss region BLR, and the second reference plane REF2 intersecting the articular surface 129AS.

The spatial module 137 may be configured to establish a best fit circle BFC along the articular surface 129AS, such as the glenoid face 129GF of the shoulder model 129S, as illustrated in the sixth display window 144-6. A point BCP may be established along the second reference plane REF2. The point BCP may correspond to a center of the best fit circle BFC. The spatial module 137 may be configured to cause the display module 136 to display the best fit circle BFC and point BCP along the articular surface 129AS. The user may interact with the menu 146M or another portion of the user interface 142 to set or adjust a radius associated with the point BCP to establish the best fit circle BFC.

Figure 7A:
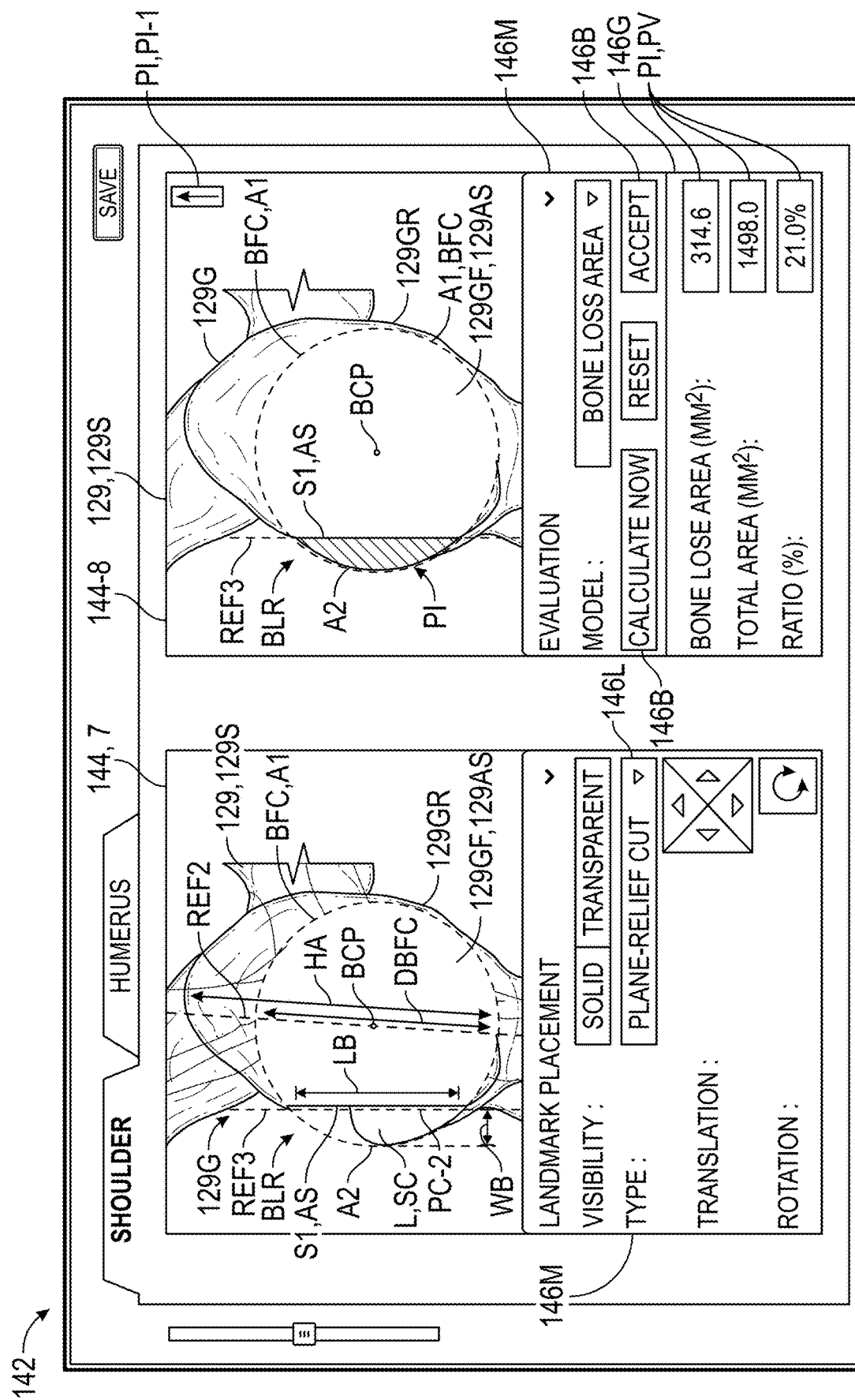
FIGS. 7A-7B illustrate various dimensions and parameters associated with the bone loss region of FIG. 6.

Referring to FIG. 7A, with continuing reference to FIGS. 2 and 6, the display windows 144 may include seventh and eighth display windows 144-7, 144-8. The display window 144-7 may be configured to display a zoom-in view of selected portions of the sixth display window 144-6. The display window 144-8 may be configured to display a solid view of the bone model 129 displayed in the display window 144-7.

The user may interact with the menu 146M associated with the seventh display window 144-7, directly with the display window 144-7 and/or another portion of the user interface 142 to establish one or more reference planes associated with a simulated relief (e.g., bevel) cut, as illustrated by a third reference plane REF3 of FIG. 7A. The spatial module 137 may be configured to adjust a geometry of the bone loss region BLR based on the third reference plane REF3.

Figure 7B:
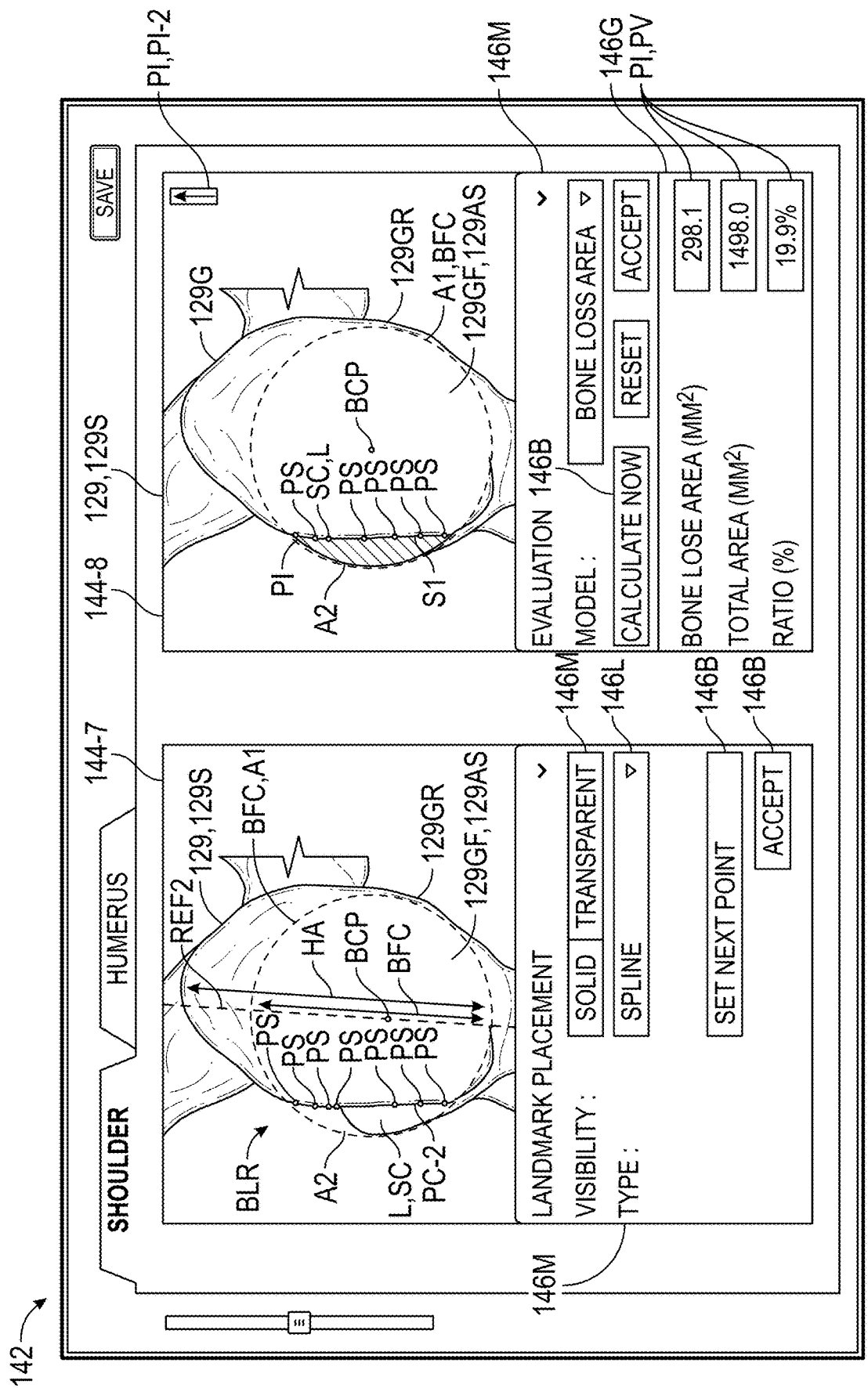

The spatial module 137 may be configured to establish one or more landmarks L associated with a profile of the articular surface 129AS, such as a profile of the glenoid rim 129GR adjacent the bone loss region BLR. In the implementation of FIG. 7B, the user may interact with the menu 146M associated with the seventh display window 144-7, directly with the display window 144-7 and/or with another portion of the user interface 142 to set a landmark L associated with the profile of the articular surface 129AS, including along a segment S1. The segment S1 may be associated with a curvature of a perimeter of the articular surface 129AS along the bone loss region BLR. The segment S1 may be an anterior segment AS associated with a perimeter of the glenoid face 129GF. The segment S1 may extend along and be established by the third reference plane REF3 and may have a substantially linear, curvilinear or complex profile. Opposed ends of the segment S1 may be established at the intersections between the perimeter of the best fit circle BFC and the third reference plane REF3. The segment S1 may be associated with a perimeter of the articular surface 129AS bounding the bone loss area BLR, which may have a curved and/or complex profile (see, e.g., FIG. 7B).

The landmark L may include a spline connection SC established by two or more interconnected points PS distributed along or otherwise adjacent to the segment S1. The user may interact with the user interface 142 to specify the points PS. In implementations, the spatial module 137 may be configured to establish the spline connection SC in response to establishing the best fit circle BFC, either automatically or in response to user interaction such as selection of a button 146B. The spatial module 137 may include one or more math libraries to determine placement of the points PS and may incorporate one or more image recognition techniques to determine a profile of the articular surface 129AS along the segment S1. The spline connection SC may substantially approximate a profile of the segment S1, which may be utilized to more accurately determine or estimate an amount of bone loss at the bone loss region BLR.

The spatial module 137 may be configured to determine one or more parameters associated with the best fit circle BFC and bone loss region BLR. The spatial module 137 may be configured to determine a total (e.g., first) area A1 established by the best fit circle BFC. The total area A1 may include at least a portion of a surface area of the articular surface 129AS, such as the glenoid face 129GF. The spatial module 137 may be configured to determine a bone loss (e.g., second) area A2. The bone loss area A2 may be established between the perimeter of the best fit circle BFC and the segment S1 associated with a perimeter of the articular surface 129AS of the bone model 129.

The spatial module 137 may be configured to determine one or more dimensions associated with the bone loss region BLR. The spatial module 137 may be configured to determine a width WB and/or length LB of the bone loss area A2, as illustrated in the display window 144-7. The width WB may be a maximum distance across the bone loss area A2 between the segment S1 and the perimeter of the best fit circle BFC. The length LB may be a maximum distance across the bone loss area A2 at points along the best fit circle BFC. The maximum distance may correspond to a length of the bone loss area A2 along the segment S1 and/or reference plane REF3.

The spatial module 137 may be configured to determine a height HA across the articular surface 129AS. The spatial module 137 may be configured to determine a diameter DBFC of the best fit circle BFC.

Figure 12:
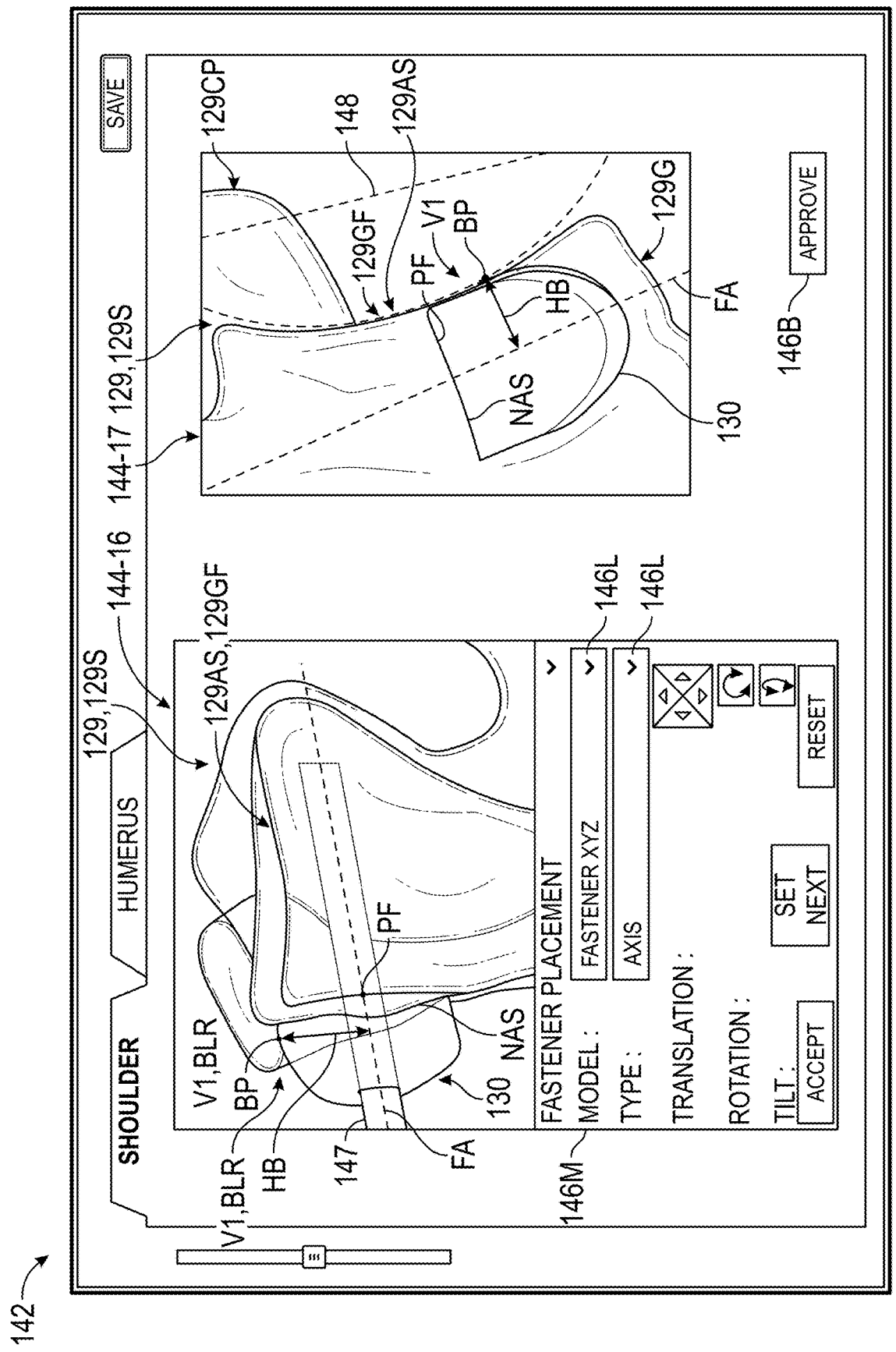
FIG. 12 illustrates a fastener model positioned relative to the bone graft and bone models of FIG. 11.

The spatial module 137 may be configured to determine a height HB associated with the bone loss area A2, as illustrated in FIG. 12. The height HB may be a distance between the boundary point BP and a respective fastener axis FA. The boundary point BP may be associated with an inferred or estimated curvature of the articular surface of the bone prior to the bone loss. The user may interact with the user interface 142 to set a position and orientation of a respective fastener axis FA, which may be associated with a selected fastener model 147 (see FIG. 12).

The comparison model 138 may be configured to determine a bone loss ratio A2:A1. The bone loss ratio A2:A1 may be defined as the bone loss area A2 divided by the total area A1 of the best fit circle BFC. The comparison model 138 may be configured to determine the bone loss ratio A2:A1 automatically and/or in response to user interaction with a button 146B of the menu 146M or another portion of the user interface 142.

The comparison module 138 may be configured to cause the display module 136 to display value(s) of one or more parameters associated with the bone loss ratio A2:A1 in a graphic 146G or another portion of the user interface 142. The graphic 146G may overlay or be arranged adjacent to one of the display windows 144 associated with the bone loss ratio A2:A1, such as the eighth display window 144-8. Example parameters include the determined total area A1 established by the best fit circle BFC, the determined bone loss area A2, and/or the determined bone loss ratio A2:A1.

The comparison module 138 may be configured to generate one or more indicators PI in response to meeting one or more predetermined criteria. The indicators PI may relate to the bone loss ratio A2:A1. The comparison module 138 may be configured to generate the indicator(s) PI in response to the bone loss ratio A2:A1 meeting one or more predetermined criteria, such as one or more predefined thresholds. The predefined thresholds may be configured or set in the system 120 according to various parameters, including procedure type, implant type, bone or joint type, bone quality, etc., and may be set and/or adjusted by the surgeon or assistant. The comparison model 138 may be configured to cause the display module 136 to display the indicators PI in the user interface 142 based on one or more predetermined criteria. The indicators PI may include value indicators PV associated with values of the determined areas A1, A2 and/or bone loss ratio A2:A1, which may be incorporated into the graphic 146G.

The predefined thresholds may include a first threshold and a second threshold. Predetermined thresholds may be established for respective bone types, joints, etc. The thresholds may be associated with a degree or severity of bone loss, which may be based on prior cases. The predefined thresholds may relate to each other. The second predefined threshold may be greater than the first predefined threshold. The first threshold may be greater than or equal to approximately 0.20. The second threshold may be greater than or equal to approximately 0.30. In implementations, the first threshold may be utilized to indicate or recommend a first type of surgical procedure, such as a Latarjet procedure. The second threshold may be utilized to indicate or recommend another, different type of surgical procedure, such as a total or reverse shoulder procedure. A bone loss ratio A2:A1 of less than the first predefined threshold, such as less than approximately 0.10, may indicate that a surgical procedure is not recommended or an alternative treatment may be utilized to treat the bone loss.

Other predetermined criteria may be associated with a height HA across the articular surface 129AS (FIGS. 7A-7B). The comparison module 138 may be configured to determine a ratio DBFC:HA of a diameter DBFC of the best fit circle BFC divided by the height HA. In implementations, a range of the ratio DBFC:HA may be between approximately 0.75 and 0.80, such as approximately 0.77. The comparison module 138 may be configured to generate an indicator PI in response to the ratio DBFC:HA being above and/or below the predefined range, which may indicate resizing and/or repositioning the best fit circle BFC to more closely approximate a profile of the articular surface 129AS.

The comparison module 138 may be configured to generate a first indicator PI (e.g., PI-1 of FIG. 7A) in response to the bone loss ratio A2:A1 meeting the first or second predefined threshold. The comparison module 138 may be configured to generate a second indicator PI (e.g., PI-2 of FIG. 7B) in response to the bone loss ratio A2:A1 meeting the first or second predefined threshold. The first and second indicators PI-1, PI-2 may be unique indicators or respective state of a common indicator PI (e.g., up arrow, down arrow, etc.).

The indicators PI may include a visual contrast of the second area A2 associated with the bone loss region BLR based on a value of the bone loss ratio A2:A1. The visual contrast of the bone loss region BLR is shown as hatching in the display window 144-8 for illustrative purposes. The visual contrast may include different colors or shades associated with the value of the bone loss ratio A2:A1. For example, the visual contrast may indicate a first (e.g., green) color when the value of the bone loss ratio A2:A1 is less than the first predefined threshold, a second (e.g., yellow) color when the value of the bone loss ratio A2:A1 is greater than or equal to the first predefined threshold but is less than the second predefined threshold, and/or a third (e.g., red) color when the value of the bone loss ratio A2:A1 is greater than or equal to the second predefined threshold. The first color may represent a first indicator, and the second color may represent a second indicator.

Figure 8:
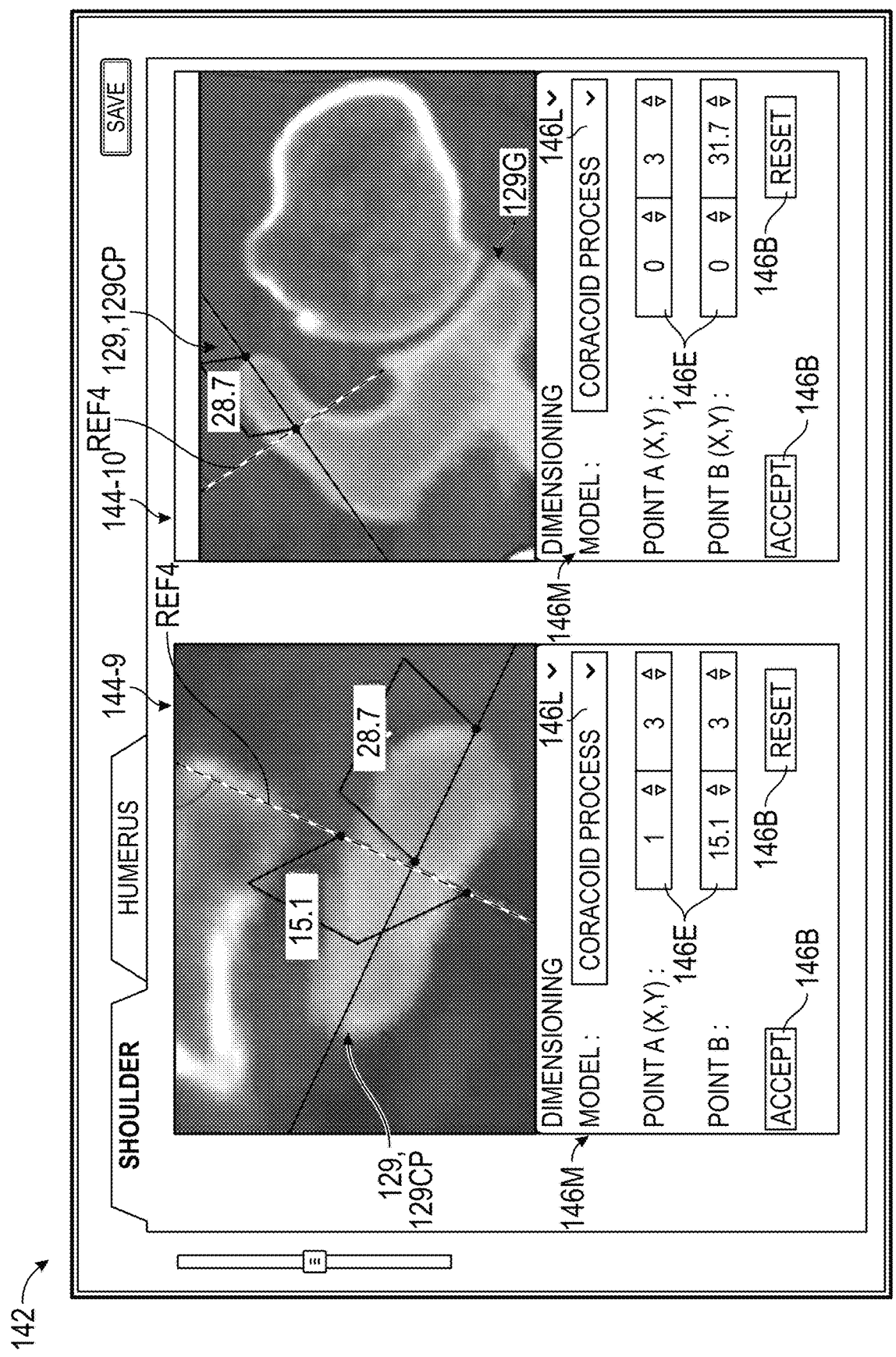
FIGS. 8-9 illustrate views of a portion of the bone model of FIG. 3 associated with a bone graft.

Referring to FIG. 8, with continuing reference to FIGS. 2-3, the system 120 may be configured for evaluating one or more regions of the anatomy for harvesting a bone graft (e.g., fragment). The bone graft may be an autograft associated with the same patient as the bone model 129 associated with the bone loss region BLR or may be an allograft associated with another person for transplanting into the patient. The display windows 144 may include ninth and tenth display windows 144-9, 144-10. The display windows 144-9, 144-10 may be linked to each other and may be configured to display different orientations of a bone model 129, such as the coracoid process 129CP of the bone model 129 associated with the bone loss region BLR, or another bone model 129 associated with another bone or joint of the patient anatomy.

The spatial module 137 may be configured to determine one or more dimensions associated with the selected bone model 129, such as a width and/or length of a portion of the bone model 129. The user may interact with the menu 146M associated with the display windows 144-7, 144-8, directly with the display windows 144-7, 144-8 and/or another portion of the user interface 142 to establish one or more reference planes associated with a simulated relief cut, as illustrated by a fourth reference plane REF4. In implementations, the user may interact with entry fields 146E in the menu 146M to set one or more points associated with the reference plane REF4 and dimensions. The spatial module 137 may be configured to determine one or more dimensions with respect to the reference plane REF4. The spatial module 137 may be configured to cause the display module 136 to display the dimensions and one or more associated markers. The user may interact with the buttons 146B in the menu 146M to accept the dimensions.

Figure 9:
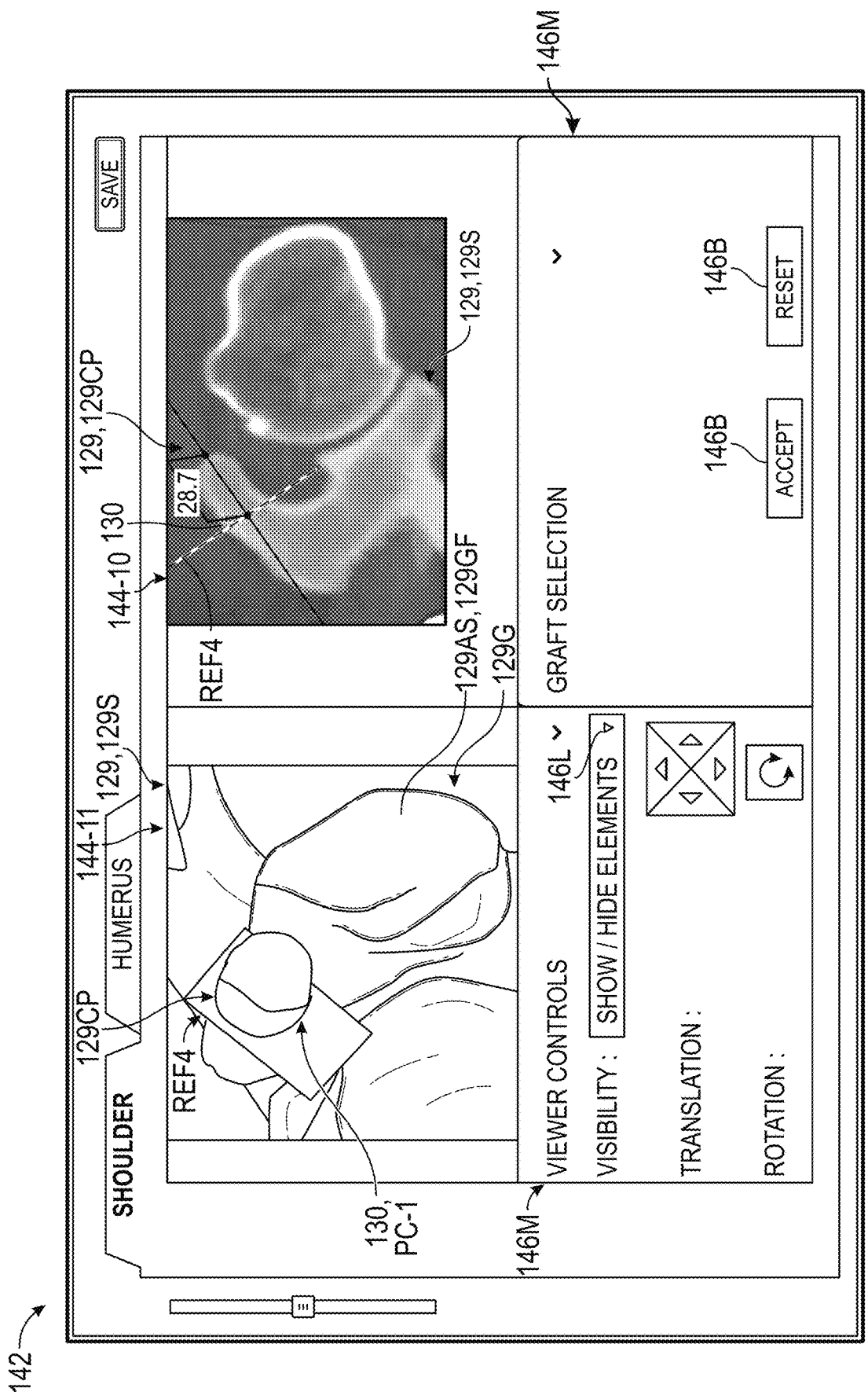

Referring to FIG. 9, with continuing reference to FIGS. 2 and 8, the display windows 144 may include an eleventh display window 144-11. The display window 144-11 may be linked to the display windows 144-9, 144-10 and may be configured to display different orientations of the selected bone model 129 of FIG. 8, such as the coracoid process 129CP. The spatial module 137 may be configured to cause the display module 136 to display the reference plane REF4 in the display window 144-11 relative to the coracoid process 129CP of the selected bone model 129.

The surgeon or assistant may interact with one of the menus 146M associated with the display windows 144-10, 144-11 and/or another portion of the user interface 142 to approve of a volume associated with a bone graft model 130. The graft model 130 may be associated with the coracoid process 129CP of the shoulder model 129S. The spatial module 137 may be configured to generate the graft model 130 and may be configured to cause the data module 135 to store the graft model 130 to memory 134 and/or the database 128. The graft model 130 may be associated with the determined dimensions and/or reference plane REF4. The graft model 130 may be established in response to setting the reference plane REF4, which may simulate a resection of the associated bone.

Figure 10:
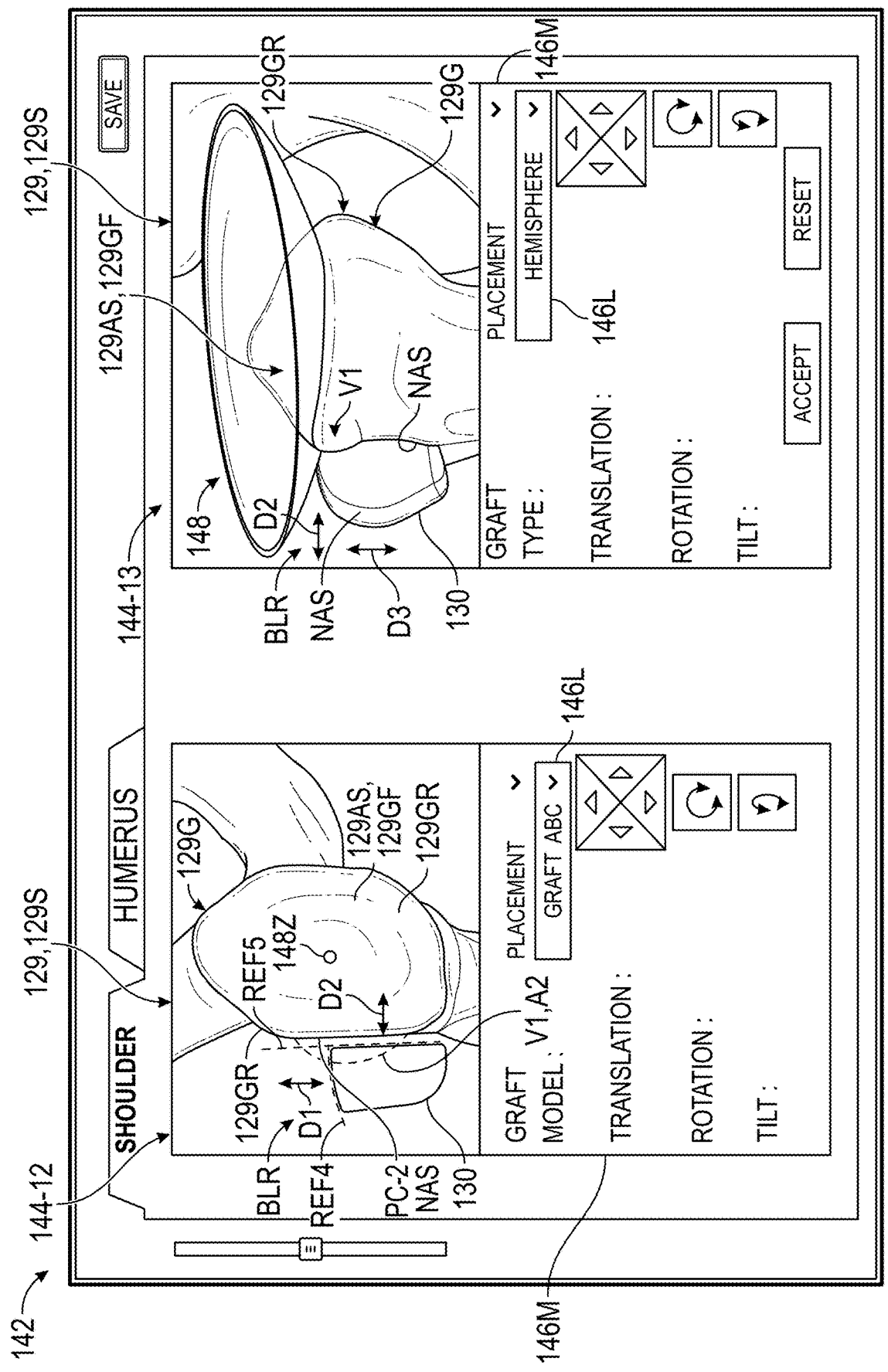
FIGS. 10-11 illustrate a bone graft and guidance object situated relative to the bone model of FIG. 3.
Figure 11:
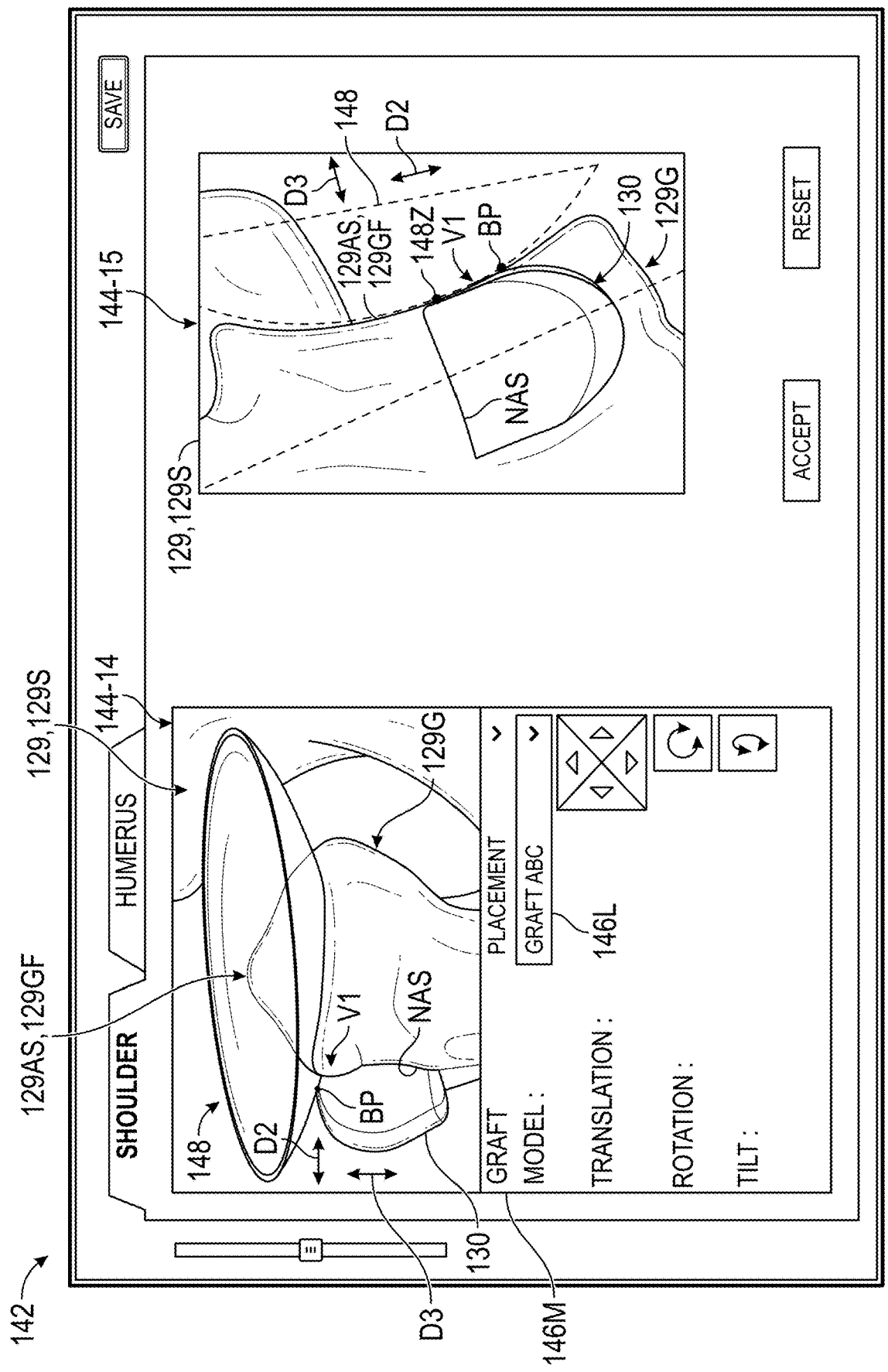

Referring to FIGS. 10-11, with continuing reference to FIGS. 2 and 9, the display windows 144 can include twelfth through fifteenth display windows 144-12 to 144-15. The user may interact with the menu 146M or another portion of the user interface 142 to select a graft model 130, such as the graft model 130 associated with the simulated relief cut established by the reference plane REF4.

The user may interact with the user interface 142 to modify a geometry of the selected graft model 130. The user may interact with the menu 146M associated with the display window 144-10, directly with the display windows 144-10 and/or another portion of the user interface 142 to establish one or more reference planes associated with a simulated relief cut, as illustrated by fifth reference plane REF5, to shape a geometry of the graft model 130. The spatial module 137 may be configured to cause changes to the graft model 130 to be stored in the memory 134 and/or database 128, including the reference planes REF4, REF5 associated with the simulated relief cuts.

The surgeon or assistant may interact with one of the menus 146M associated with the display windows 144-12, 144-13, 144-14, 144-15, directly with the display windows 144-12, 144-13, 144-14, 144-15 and/or another portion of the user interface 142 to position the graft model 130 with respect to a selected bone model 129. The user may interact with the user interface 142 to move the selected graft model 130 in directions D1, D2 and/or D3 relative to the selected bone model 129. The user may interact with the user interface 142 to move the graft model 130 into abutment with the bone model 129, such as a non-articular surface NAS. The non-articular surface NAS may be an anterior surface of the glenoid 129G.

The display module 136 may be configured to display one or more guidance objects 148 to assist in positioning of the graft model 130. The guidance object 148 may be a hemispherical object. The hemispherical object 148 may have a geometry that approximates a native curvature of the articular surface prior to the bone loss. The spatial module 137 may be configured to generate the hemispherical object 148 having a zenith 148Z positioned along or otherwise adjacent to the articular surface 129AS of the selected bone model 129. The spatial module 137 may be configured to fit a boundary of the hemispherical object 148 relative to a curvature of the articular surface 129AS, such as a curvature of the glenoid face 129GF. The spatial module 137 may be configured to execute one or more math libraries or functions to determine a fit between a curvature of the hemispherical object 148 relative to the curvature of the articular surface 129AS. The user may interact with the one of the menus 146M associated with the display windows 144-13, 144-14, 144-15, directly with the display windows 144-13, 144-14, 144-15, and/or with another portion of the user interface 142 to adjust or set the shape, position and/or orientation of the hemispherical object 148 and associated zenith 148Z relative to the bone model 129.

The spatial module 137 may be configured to position the selected bone and graft models 129, 130 into contact with each other at a specified or defined position and orientation, which may be according to user interaction with the display windows 144, menu 146M, and/or other objects 146 of the user interface 142. The display module 136 may be configured to display the bone model 129 and graft model 130 relative to each other.

The spatial module 137 may be configured to position the bone graft model 130 in a first volume V1 associated with the bone loss area A2 (shown in dashed lines in FIG. 10) such that a boundary of the bone graft model 130 is substantially aligned with the boundary of the hemispherical object 148 at a boundary point BP, as illustrated in FIG. 11. The spatial module 137 may be configured to position the boundary of the bone graft model 130 in substantial alignment with the boundary of the hemispherical object 148 at the boundary point BP automatically and/or in response to user interaction with the user interface 142. The display module 136 may be configured to display the bone graft model 130 in the first volume V1 associated with the bone loss area A2.

Referring to FIG. 12, with continuing reference to FIGS. 2 and 10-11, the display windows 144 may include sixteenth and seventeenth display windows 144-16, 144-17. The display window 144-17 may be configured to display the hemispherical object 148 relative to the graft model 130 in which the boundary of the graft model 130 is substantially aligned with the curvature of the hemispherical object 148 at the boundary point BP. The display window 144-16 may be configured to display the graft model 130 at the substantially aligned position.

The user may interact with the menu 146M associated with the display window 144-16, directly with the display windows 144-16, 144-17, or with another portion of the user interface 142 to set a position and orientation of one or more fastener models 147. The fastener models 147 may be associated with respective fasteners, such as pins, nails, cannulated and non-cannulated compression screws, etc. Each fastener model 147 may be stored in one or more records 139 in the database 128. The user may interact with the user interface 142 to set a position and orientation of a respective fastener axis FA associated with the selected fastener model 147. The fastener model(s) 147 may be utilized to simulate securing a bone graft with one or more fastener at an insertion point PF along the bone model 129 established by the respective fastener axis FA. The insertion point PF may be established along the non-articular surface NAS of the bone model 129.

The surgeon or assistant may interact with the user interface 142 to approve the surgical plan 131, including a geometry, placement, resections and other revisions, fastener positions, and other parameters associated with the selected bone model 129 and graft model 130. The data module 135 may be configured to store the approved surgical plan 131 and any subsequent changes in the memory 134 and/or database 128.

Figure 13:
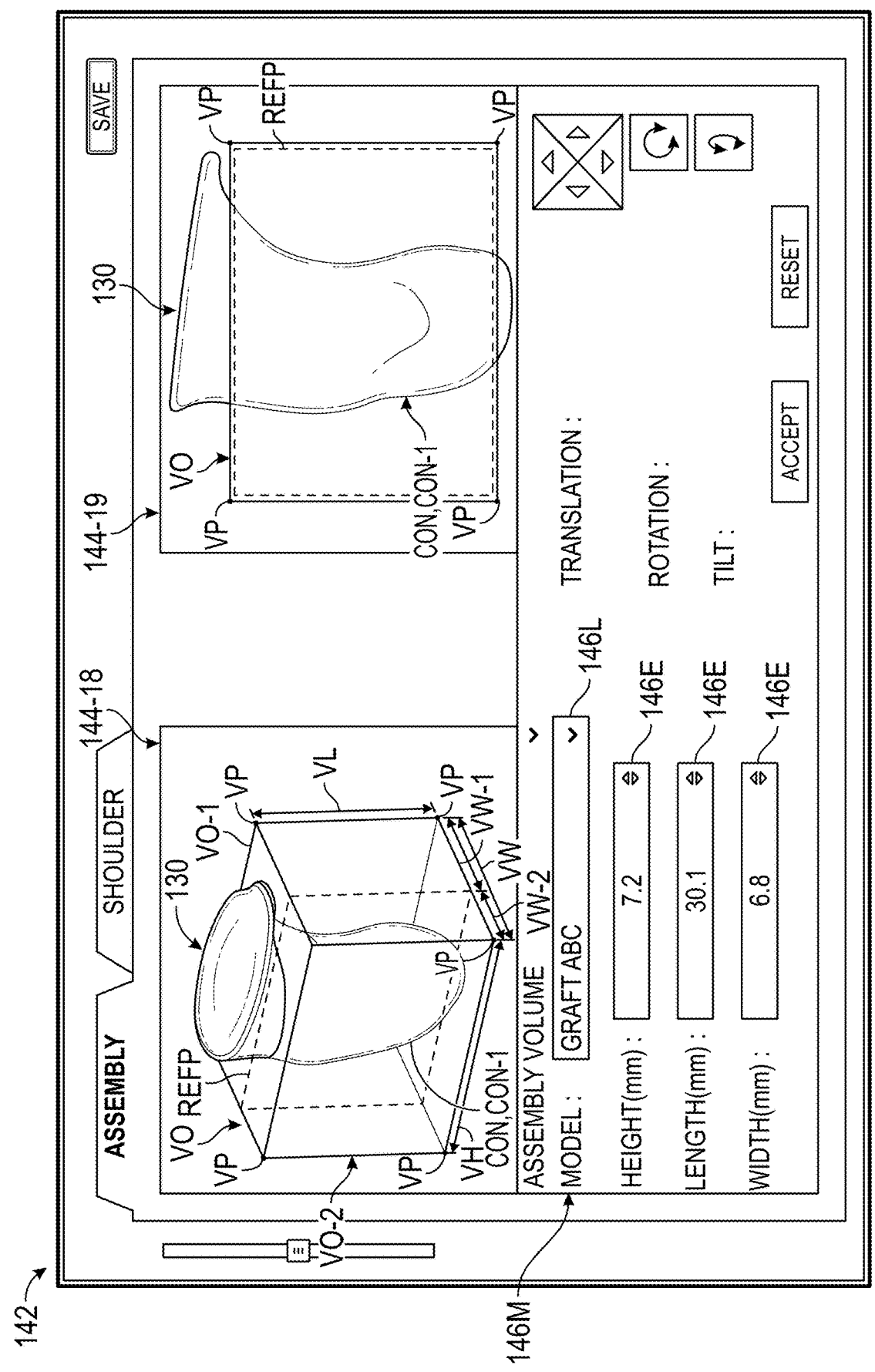
FIG. 13 illustrates a volume object relative to a graft model in the graphical user interface of FIG. 2.

Referring to FIG. 13, with continuing reference to FIG. 2, the system 120 may be configured to establish one or more dimensions or settings associated with instrumentation. The instrumentation may be utilized in harvesting a bone graft and/or placement of a bone graft in an orthopaedic procedure, including any of the procedures disclosed herein such as a Latarjet procedure. The spatial module 137 may be configured to generate one or more (e.g., guide) assembly models 141 associated with the dimensions or settings.

The comparison module 138 may be configured to generate one or more dimensions associated with each assembly model 141 based on one or more parameters associated with the determined bone loss area A2 and/or other aspects of the bone loss region BLR. The assembly model 141 may be dimensioned with respect to one or more patient-specific contours CON, which may be associated with a respective bone model 129, graft model 130 and/or surgical plan 131 for a patient.

The patient-specific contours CON may include a first patient-specific contour CON-1. The first contour CON-1 may be associated with a selected graft model 130 in an initial cut (e.g., harvested) state, as illustrated in FIG. 13.

The display windows 144 may include eighteen and nineteen display windows 144-18, 144-19. The display module 136 may be configured to display an isolated view of the selected graft model 130 in the display windows 144-18, 144-19. The spatial model 137 may be configured to cause the display module 136 to display a volume object VO about the graft model 130. The volume object VO may a cube or rectangle including a width (e.g., first) dimension VW, a length (e.g., second) dimension VL and a height (e.g., third) dimension VH. The dimensions VW, VL, VL may be established such that the volume object VO at least partially or completely encompasses a volume of the graft model 130. The comparison module 138 may be configured to generate the dimensions VW, VL, VL and associated parameters of the assembly model 141.

The volume object VO may be partitioned by one or more reference planes REFP into one or sub-volumes, which may include a first sub-volume VO-1 and a second sub-volume VO-2. The width dimension VW may include a first width dimension VW-1 and a second width dimensions VW-2 associated with the respective sub-volumes VO-1, VO-2. The user may interact with the user interface 142 to set a position and orientation of each plane REFP.

The first width (e.g., first dimension) VW-1 may be associated with the width WB of the bone loss area A2. The length (e.g., second dimension) VL may be associated with the length WL of the bone loss area A2. The length WL may be established by ends of the segment S1 (FIGS. 7A-7B). The height (e.g., third dimension) VH may be associated with the height HB of the boundary point BP relative to a (e.g., surface contact) point of the selected graft model 130 along the curvature of the articular surface 129AS, such as the glenoid face 129GF of the shoulder model 129S (FIG. 12).

The dimensions VW, VL, VH of the volume object VO, including the widths VW-1, VW-2, may be set based on one or more parameters associated with the bone loss region BLR, including a determined bone loss ratio A2:A1, a width WB and length LB of a bone loss area A2, and/or a height HB associated with the bone loss area A2 (see FIGS. 7A and 12). The length dimension VL may be greater than or equal to a determined length LB of the bone loss area A2. In implementations, the length dimension VL is about 25-30 mm. The width dimension VW may be greater than or equal to a determined width WB of the bone loss area A2. The height dimension VH may be greater than or equal to the height HB associated with the bone loss area A2. In implementations, the dimensions VW, VH are at least 1.2 times a diameter of the graft model 130. The dimension VL may be established such that a portion of the graft model 130 (e.g., 2-5 mm) extends outwardly of the volume object VO.

The user may interact with the menu 146M associated with the display windows 144-18, 144-19, directly with the display windows 144-18, 144-19 or another portion of the user interface 142 to set or adjust a size, position and orientation of volume object VO, including the dimensions VW, VL, VL and points VP establishing a boundary of the volume object VO.

Figure 14:
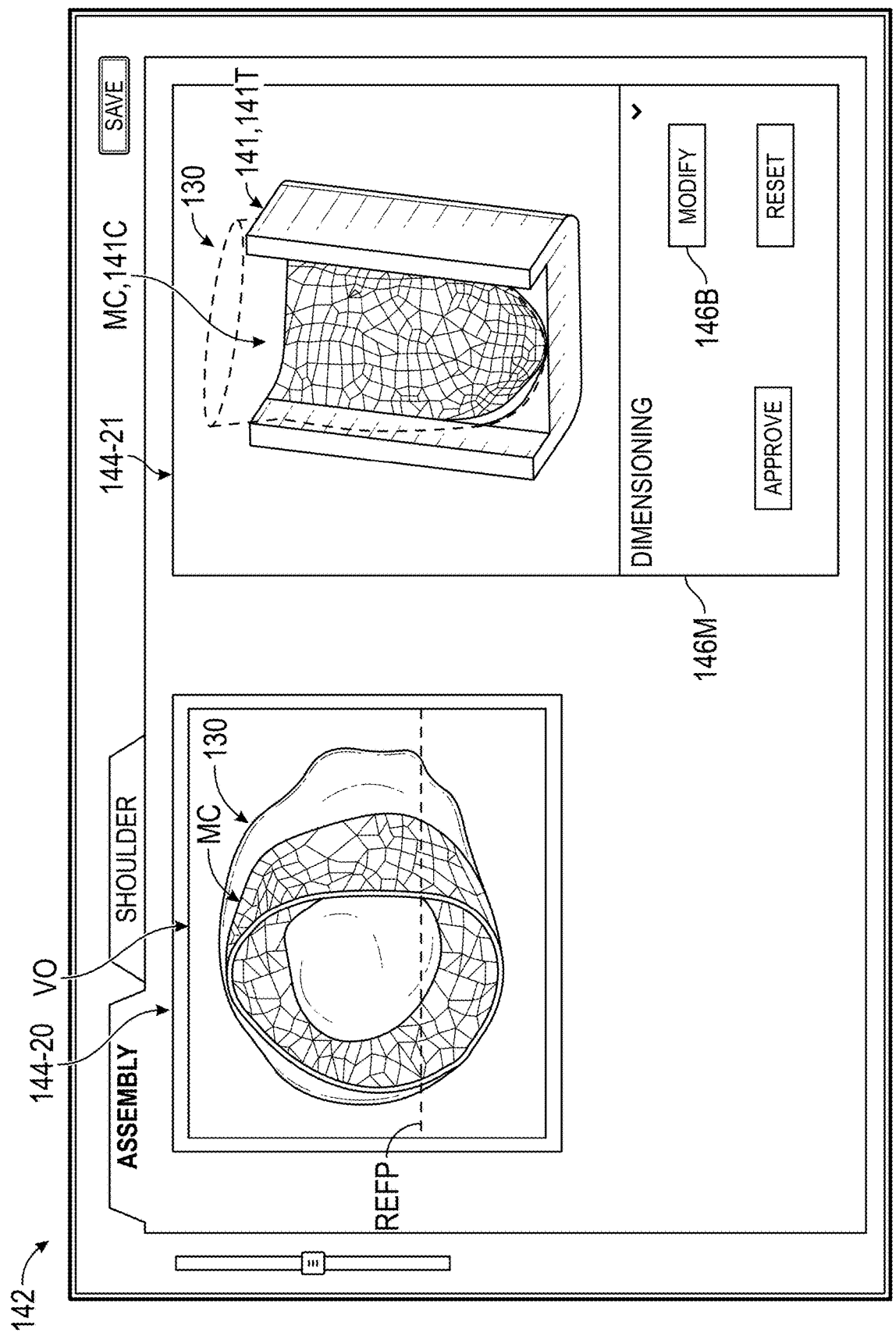
FIG. 14 illustrates an assembly model relative to the graft model of FIG. 13.

Referring to FIG. 14, with continuing reference to FIGS. 2 and 13, the display windows 144 may include display windows 144-20, 144-21. The spatial module 137 may be configured to generate a matched cavity MC within the volume object VO. The spatial module 137 may be configured to cause the display module 136 to display a profile of the matched cavity MC, in isolation and/or together with the volume object VO and/or graft model 130, in the display windows 144-20, 144-21. The matched cavity MC may have a contour that substantially corresponds to a profile of portions of the graph model 130 positioned within a volume of the volume object VO.

The spatial module 137 may be configured to generate geometry of the assembly model 141 based on the matched cavity MC and/or volume object VO. The assembly model 141 may include a template 141T having a cavity (e.g., recess) 141C dimensioned according to the matched cavity MC. The user may interact with the user interface 142 to modify aspects of the assembly model 141. In implementations, the user may interact with a button 146B to edit the generated template 141T in another portion of the planning environment 126, or in a separate CAD tool. The user may edit the template 141T to incorporate various features, including recesses, grooves, passages and openings, flanges, etc. The spatial module 137 may be configured to cause the data module 135 to store the template 141T, including revisions and other aspects of the generated assembly model 141, in the memory 134 and/or a record 139 in the database 128. Edits to the assembly model 141 may be saved to the memory 134 or to the database 128 as one or more records 139. Assembly models 141 having various geometries and dimensions may be generated based on the template 141T and matched cavity MC, which may provide the surgeon with additional flexibility in planning and implementing a surgical plan 131.

Figure 15:
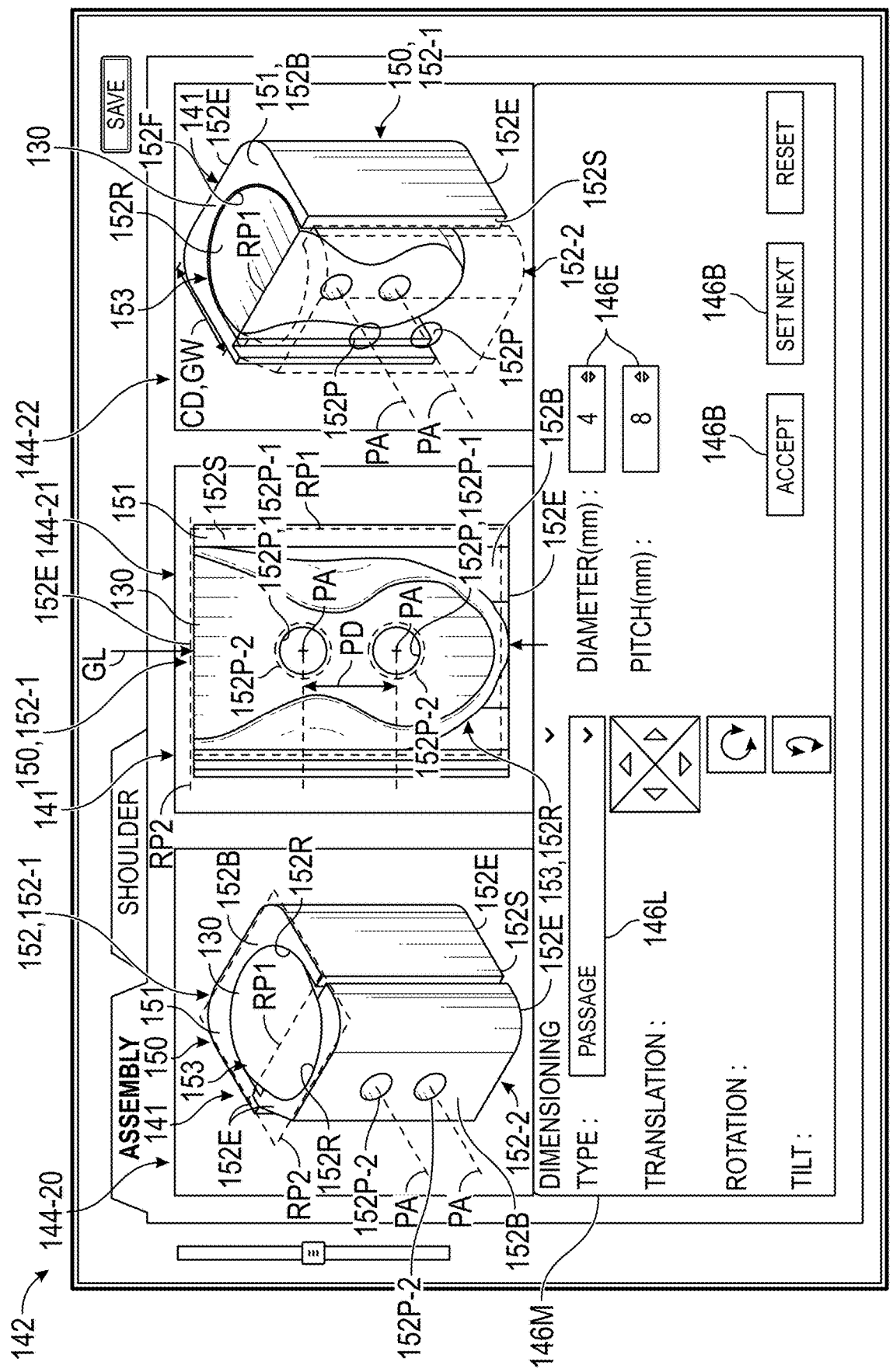
FIG. 15 illustrates aspects of the assembly model of FIG. 14 in the graphical user interface.

Referring to FIG. 15, with continuing reference to FIG. 13-14, the display windows 144 may include display windows 144-20 to 144-22. The display windows 144-20 to 144-22 may be configured to display a selected assembly model 141 in various orientations and/or positions. The assembly model 141 may be associated with a guide assembly (e.g., 249 of FIGS. 18-19). The guide assembly may be utilized for a surgical procedure, including any of the orthopaedic procedures disclosed herein.

The assembly model 141 and associated guide assembly may include a shell 150 having a shell body 151. The shell body 151 may include one or more shell portions 152, such as a first shell portion 152-1 and a second shell (e.g., outer clamping) portion 152-2. The shell portions 152-1, 152-2 may cooperate to establish and bound a cavity 153 in an assembled position. The cavity 153 may be dimensioned according to a contour of the matched cavity MC (FIG. 14). In implementations, the cavity 153 may be dimensioned according to a patient-specific contour of a bone associated with the selected graft model 130, which may substantially correspond to the contour of the matched cavity MC. In implementations, the cavity 153 may be dimensioned according to a contour of a resected portion of the coracoid process 129CP of the shoulder model 129S (e.g., FIGS. 8-9).

Each shell portion 152 may include a main body 152B dimensioned to extend between opposed end walls 152E. The main body 152B may include a (e.g., first) sidewall 152S dimensioned to extend between the end walls 152E. The sidewalls 152S of the shell portions 152-1, 152-2 may be dimensioned to abut or otherwise face each other in the assembled position. The sidewalls 152S of the shell portions 152-1, 152-2 may be dimensioned to abut each other to encircle the cavity 153 in the assembled position. In implementations, the first and second shell portions 152-1, 152-2 may be releasably secured to each other to establish a clamshell arrangement. Each of the shell portions 152-1, 152-2 may have a unitary construction. In implementations, the second shell portion 152-2 may be omitted.

Each shell portion 152 may include a recess 152R dimensioned to extend inwardly from the sidewall 152S of the main body 152B. The recesses 152R may cooperate to establish the cavity 153 in the assembled position. Surfaces of each recess 152R may be dimensioned according to a contour of the matched cavity MC. The recess 152R of the first shell portion 152-1 may be dimensioned to extend at least 120 degrees, or more narrowly less than or equal to 180 degrees, about a periphery of the coracoid process 129CP.

The shell 150 may be dimensioned to establish one or more resection (e.g., cutting) surfaces for resecting a portion of bone associated with the selected graft model 130. The resection surfaces may be established by one or more resection planes, such as first and second resection planes RP1, RP2 (shown in dashed lines). The sidewall 152S along the first shell portion 152-1 may dimensioned to establish the first resection plane RP1. One or more end walls 152E of the shell portions 152 may be dimensioned to establish the second resection plane RP2. In implementations, adjacent end walls 152E of the shell portions 152-1, 152-2 may establish the second resection plane RP2 in the assembled position. The shell 150 may be dimensioned such that the second resection plane RP2 is transverse to the first resection plane RP1. In implementations, the second resection plane RP2 is substantially perpendicular to the first reference plane RP1.

The first resection plane RP1 may be established with respect to the width WB of the bone loss area A2 (FIG. 7A). The first resection plane RP1 may be dimensioned to establish a first (e.g., cavity) depth CD (see window 144-22). The first depth CD may be established between a floor 152F of the recess 152R of the first shell portion 152-1 and a first resection surface established along the sidewall 152S. The first depth CD may be associated with a dimension of another bone than a bone associated with bone loss region BLR, or another portion of the same bone, such as a coracoid process of the shoulder. Resecting a portion of the graft associated with the selected graft model 130 along the first resection plane RP1 may establish a graft width GW, which may be substantially equal to the first depth CD.

The second resection plane RP2 may be established with respect to the length LB of the bone loss area A2 (FIG. 7A). The length VL of the assembly model 141 (FIG. 13) may be greater than or equal to the length LB of the bone loss area A2. Resecting a portion of the graft associated with the selected graft model 130 along the second resection plane RP2 may establish a graft length GL (see window 144-21). The length GL may be less than, substantially equal to, or greater than the length VL of the assembly model 141.

The shell portions 152 may include one or more passages 152P dimensioned to extend at least partially completely through a thickness of the main body 152B. Each passage 152P may be dimensioned to extend along a passage axis PA. The passages 152P and respective passage axes PA may be established at positions associated with the boundary point BP (FIG. 12) such that a graft associated with the selected graft model 130 is positioned along the selected bone model 129 at a predetermined height or offset from the articular surface of the bone. The first shell portion 152-1 may include first passage(s) 152P-1. The second shell portion 152-2 may include second passage(s) 152P-2. The passage axes PA of pairs of the passages 152P-1, 152P-2 may be substantially aligned in the assembled position such that a guide member (e.g., guide pin), drill bit, fastener and/or other device may be insertable through the passage 152P-2, across the cavity 153 and through the passage 152P-1 and then into a non-articular surface NAS of a bone associated with the selected bone model 129, such as an anterior surface of the glenoid 129G (see, e.g., FIG. 16). The passage axes PA of adjacent passages 152P may establish a pitch PD. The pitch PD may be between about 5-10 mm. The user may interact with the menu 146M, directly with the display windows 144-20 to 144-22, or another portion of the user interface 142 to set a position, orientation and/or dimension of each of the passages 152P, passage axes PA and pitch PD associated with the selected assembly model 141.

Figure 16:
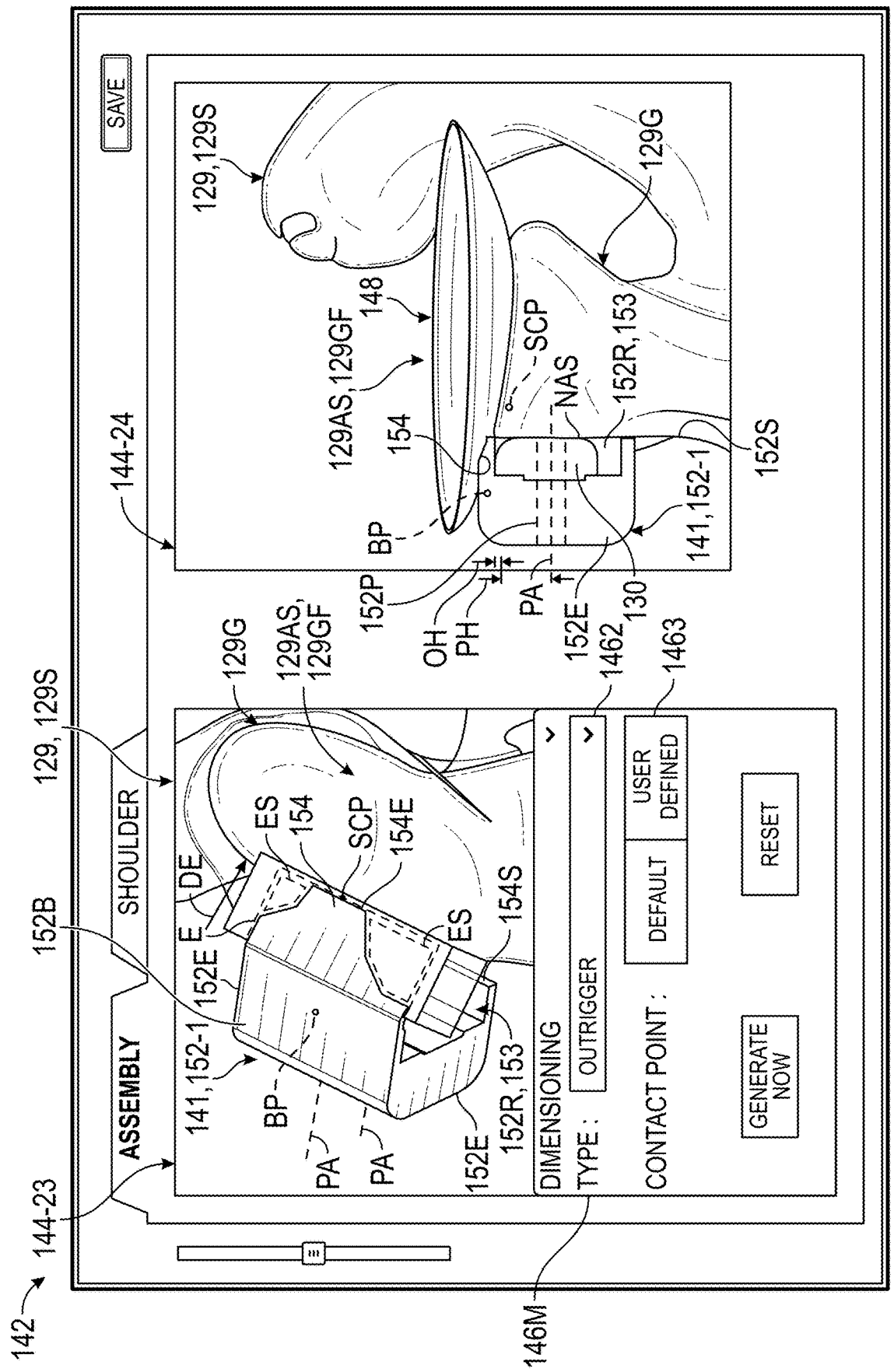
FIGS. 16-17 illustrate aspects of the assembly model of FIG. 14 situated relative to the bone model of FIG. 3 in the graphical user interface.

Referring to FIG. 16, with continuing reference to FIGS. 2 and 15, the selected assembly model 141 may include one or more features dimensioned to establish a position of the selected graft model 130 and associated guide assembly relative to an articular surface of a bone associated with the selected bone model 129, such as the glenoid face 129GF of the glenoid 129G or another articular surface 129AS. The display windows 144 may include display windows 144-23, 144-24. The display windows 144-23, 144-24 may be configured to display the selected assembly model 141 in various orientations and/or positions relative to the selected bone model 130.

The system 120 may be configured to establish one or more outriggers (e.g., flanges) 154 of the selected assembly model 141. The outrigger 154 may be dimensioned to extend outwardly from one of the shell portions 152, such as the first shell portion 152-1, to a free end 154E. The free end 154E may be dimensioned to contact the articular surface 129AS of the selected bone model 129 at a surface contact point SCP according to the one or more dimensions generated by the spatial module 137. The articular surface may be the glenoid face 129GF of the glenoid 129G. The surface contact point SCP may be a single point or may be a localized region along the articular surface 129AS.

The spatial module 137 may be configured to establish the outrigger 154 utilizing various techniques, such as an extrusion operation. The spatial module 137 may be configured to establish the outrigger 154 by extruding a portion E (shown in dashed lines) including an angled surface of a predefined thickness in a direction DE from the main body 152B of the shell portion 152 to the free end 154E at the surface contact point SCP. The free end 154E may have various geometries, such as a generally planar geometry or a contoured geometry dimensioned according to the patient-specific contour associated with the bone model 129 at the surface contact point SCP. In implementations, one or more sections ES (shown in dashed lines) of the extruded portion E may be removed to establish the outrigger 154. The surface contact point SCP may be established automatically by the spatial module 137 in response to the extrusion. The user may set or alter a position of the surface contact point SCP by interaction with the menu 146M, directly with the display windows 144-23, 144-24, or with another portion of the user interface 142.

The outrigger 154 may be established according to the height HB of the boundary point BP relative to the passage axes PA (FIG. 12) and/or a outrigger height (e.g., dimension) OH associated with the articular surface 129AS of the selected bone model 129. The spatial module 137 may be configured to generate the outrigger height OH based on one or more parameters associated with the bone loss region BLR, including a relative height or laterization established by a position of the selected graft model 130 relative to the selected bone model 129 at the bone loss region BLR. The outrigger height OH may be associated with a height of the boundary point BP of the hemispherical object 148 relative to the surface contact point SPC. The surface contact point SCP may be established along the curvature of the articular surface 129AS, such as the glenoid face 129GF of the shoulder model 129S. The spatial module 137 may be configured to cause the display module 136 to display the assembly model 141 including each outrigger 154 in isolation, in contact with the articular surface 129AS at the surface contact point SPC and/or in relation to the hemispherical object 148.

A position of the free end 154E of the outrigger 154 relative to the cavity 153 may be established with respect to the outrigger height OH and/or boundary point BP of the hemispherical object 148 such that an outermost position of the selected graft model 130 is substantially aligned with the boundary point BP, which may be lateral or outward of the surface contact point SCP and adjacent portions of the articular surface 129AS. In implementations, a position of the free end 154E of the outrigger 154 at the surface contact point SCP may be established with respect to a passage height PH. The passage height PH may correspond to a distance between the free end 154E of the outrigger 154 and one or more of the passage axes PA.

Figure 17:
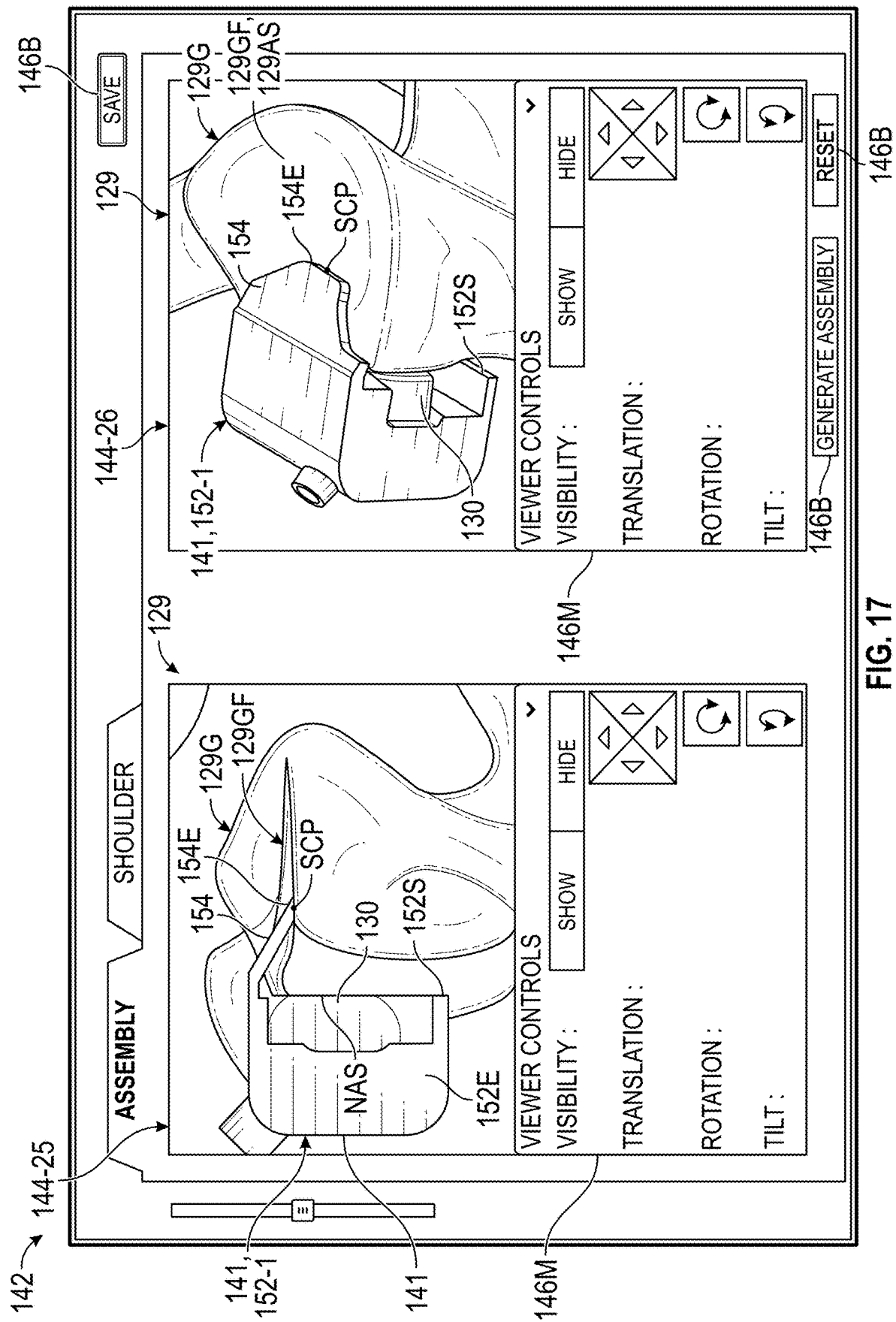

Referring to FIG. 17, with continuing reference to FIGS. 2 and 16, the display windows 144 may include display windows 144-25, 144-26. The display module 136 may be configured to display the resultant assembly model 141 including the outrigger 154 in various positions and/or orientations relative to the selected bone model 129 in the display windows 144-25, 144-26.

The user may interact with one or more buttons 146B or another portion of the user interface 142 to save the assembly model 141 to the memory 134 and/or database 128 and cause a physical guide assembly associated with the assembly model 141 to be generated. The generating may include causing the physical guide assembly to be fabricated according to dimensions and geometry specified in the assembly model 141. The physical guide assembly can include one or more patient-specific surfaces and other features associated with the respective surgical plan 131.

Figure 18:
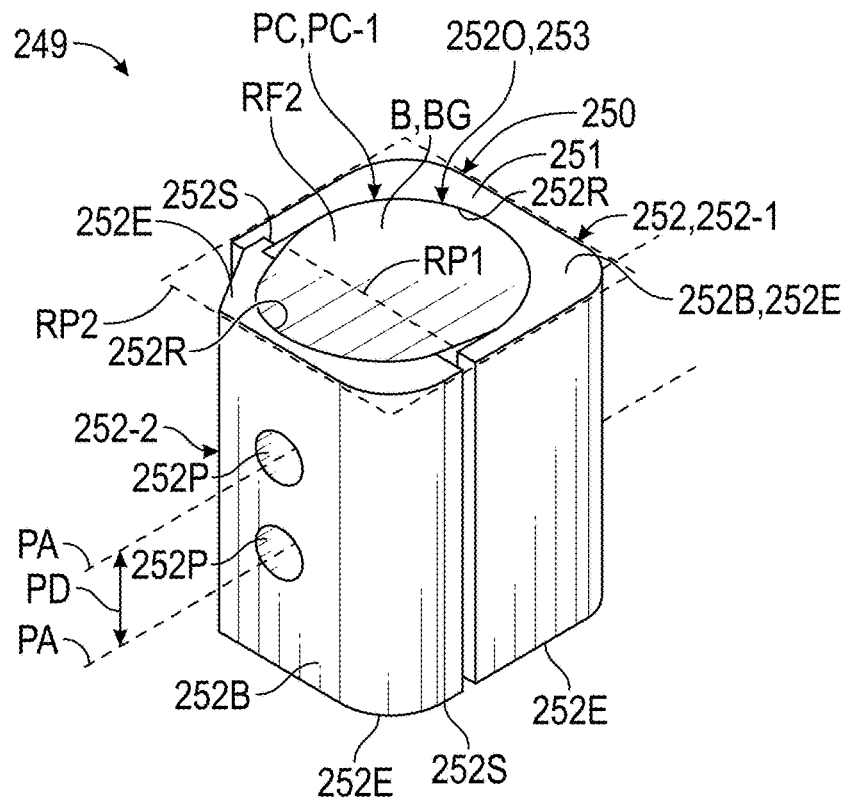
FIGS. 18-19 illustrate an exemplary assembly.
Figure 19:
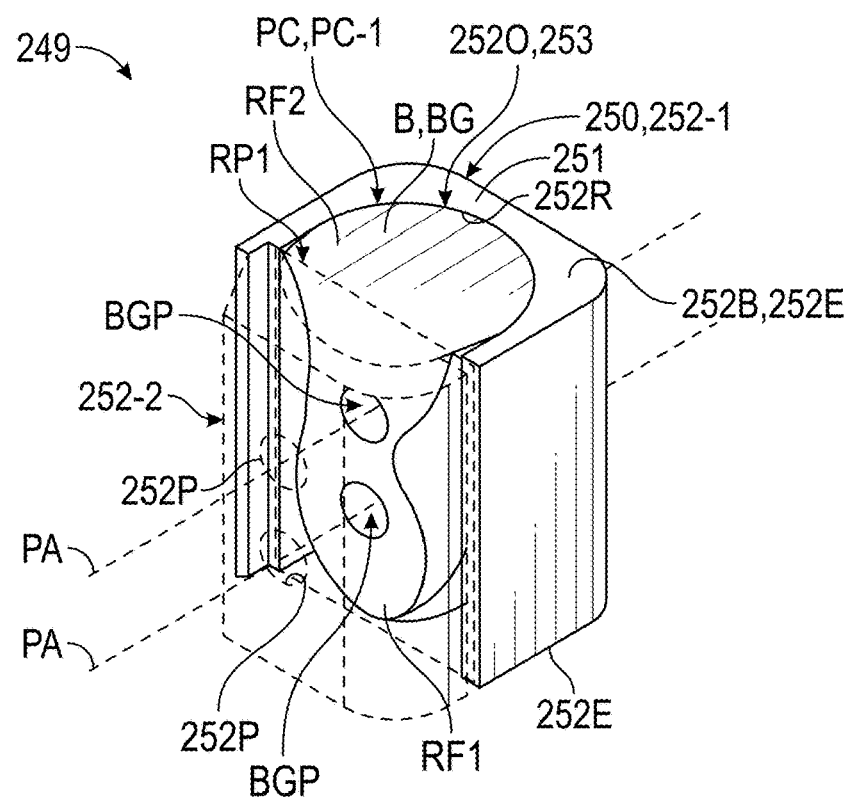

FIGS. 18-19 illustrate an exemplary guide assembly 249. The guide assembly 249 may be utilized to perform any of the surgical procedures disclosed herein, including orthopaedic procedures such as a Latarjet procedure. The assembly 249 may be designed, fabricated or otherwise formed utilizing any of the techniques disclosed herein, including the planning system 120. The assembly 249 may incorporate any of the features of the assembly model 141.

The assembly 249 may include a shell 250 including a shell body 251. The shell body 251 may be dimensioned according to one or more patient-specific contours PC, such as a first patient-specific contour PC-1 associated with a bone B. The shell 250 may include one or more shell portions 252. The shell portions 252 may include a first shell portion 252-1 and a second shell portion 252-2. The second shell portion 252-2 may be dimensioned to abut the first shell portion 252-1 in an assembled position. The first and second shell portions 252-1, 252-2 may be releasably secured to each other in the assembled position. Each of the first and second shell portions 252-1, 252-2 may include a shell (e.g., main) body 252B extending between opposed end walls 252E. A sidewall 252S of the shell body 252B may extend between the end walls 252E.

The shell 250 may include a cavity 253 dimensioned to capture and resect a portion of bone, such as a coracoid process of a patient. In implementations, a recess 252R may extend inwardly from the sidewall 252S of the shell portion 252. The recesses 252R of the first and second shell portions 252-1, 252-2 may cooperate to establish the cavity 253. The cavity 253 may be dimensioned according to the first patient-specific contour PC-1. The first patient-specific contour PC-1 may be associated with a surface contour of an outer periphery of the bone B. The bone B may associated with the selected graft model 130 (FIG. 13). The bone B may be a coracoid process of a patient. The shell portions 252-1, 252-2 may be dimensioned to capture the bone B associated with the first patient-specific contour PC-1 within the cavity 253. The shell 250 can be dimensioned to establish one or more openings 2500 along the respective end walls 252E. The openings 2500 may be dimensioned such that a portion of the bone B and/or other tissue (e.g., tendon) may protrude outwardly from the cavity 253. The openings 2500 may reduce a likelihood of impingement of any distal tendinous attachment.

The shell 252 may be dimensioned to establish one or more resection (e.g., cutting) surfaces for resecting a portion of the bone B. The resection surfaces may be established according to any of the techniques disclosed herein, such as by one or more resection planes, including first and second resection planes RP1, RP2 (shown in dashed lines). The sidewall 252S along the first shell portion 252-1 may dimensioned to establish the first resection plane RP1. One or more end walls 252E of the shell portions 252 may be dimensioned to establish the second resection plane RP2. In implementations, adjacent end walls 252E of the shell portions 252-1, 252-2 may cooperate to establish the second resection plane RP2 in the assembled position. The shell 250 may be dimensioned such that the second resection plane RP2 is transverse to the first resection plane RP2. In implementations, the second resection plane RP2 is substantially perpendicular to the first reference plane RP1.

The bone B may be resected along the second reference plane RP2 to establish a bone graft BG. The resection along the second reference plane RP2 may establish a second resection face (e.g., surface) RF2 of the bone graft BG (see also FIGS. 27-29). The bone graft BG may be resected along the first reference plane RP1 to establish a first resection face (e.g., surface) RF1 of the bone graft BG1 (see also FIGS. 27-30).

The shell portions 252 may include one or more passages 252P dimensioned to extend at least partially or completely through a thickness of the main body 252B. The passages 252P may be dimensioned to at least partially receive a guide member (e.g., guide pin), drill bit, fastener and/or other device, which may be utilized to form one or more passages BGP through the bone graft BG (FIG. 19). Each passage 252P may be dimensioned to extend along a passage axis PA. The passage axes PA of adjacent passages 252P may establish a pitch PD. The passages 252P and passage axes PA may be dimensioned utilizing any of the techniques disclosed herein.

Figure 20:
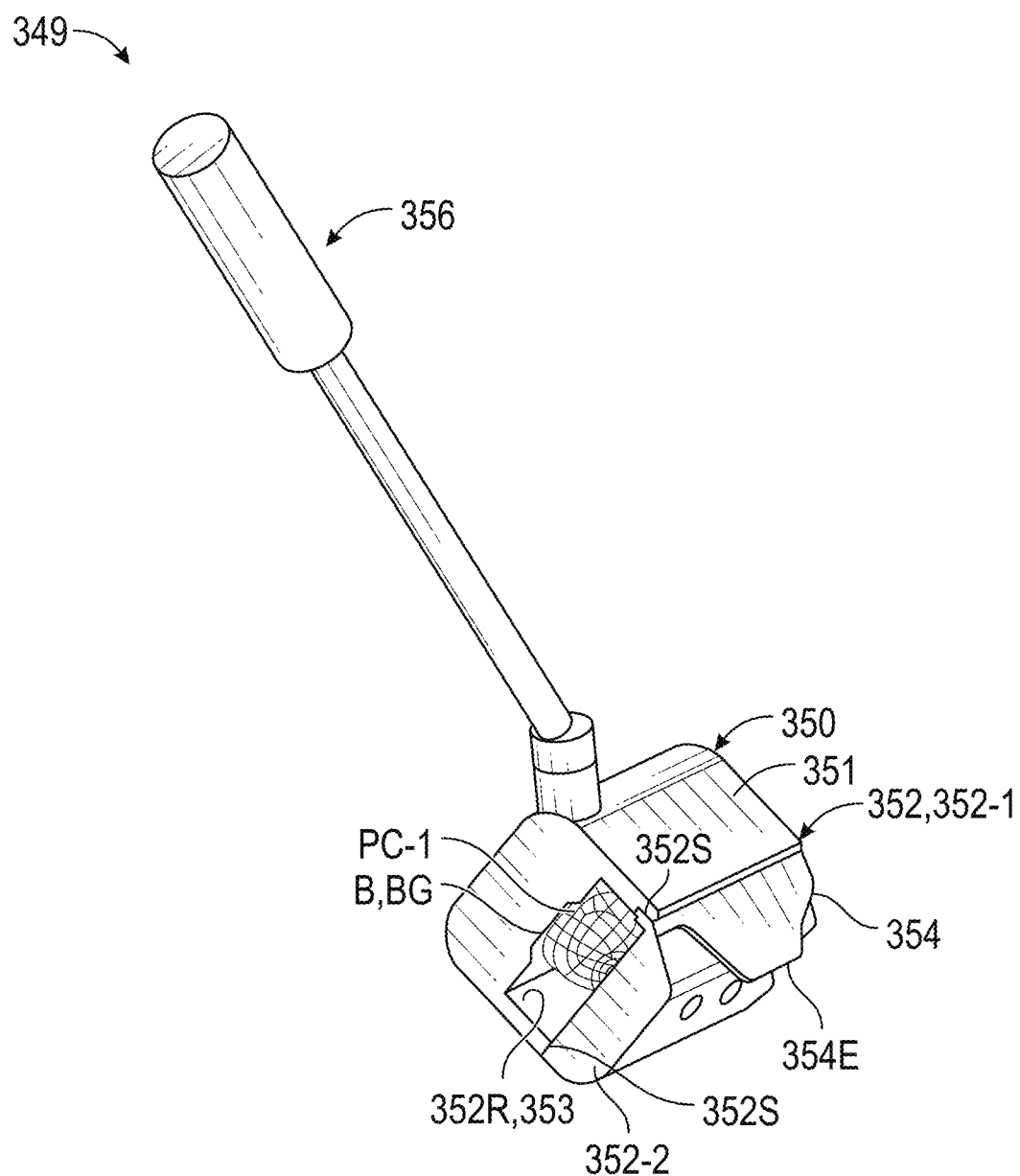
FIGS. 20-30 illustrate another exemplary assembly, with FIGS. 20 and 27-30 relative to a bone graft.

FIG. 20 illustrates an exemplary guide assembly 349. The guide assembly 349 may be utilized to perform any of the surgical procedures disclosed herein. The assembly 349 may be designed, fabricated or otherwise formed utilizing any of the techniques disclosed herein, including the planning system 120. The assembly 349 may incorporate any of the features of the assembly model 141 and guide assembly 249. FIGS. 21-28 illustrate aspects of the assembly 249.

Referring to FIG. 20, the assembly 349 may include a shell 350. The shell 350 may include one or more shell portions 352. The shell portions 352 may include a first shell portion 352-1 and a second shell portion 352-2. The shell portions 352-1, 352-2 may be dimensioned to abut each other in an assembled position. The shell portions 352-1, 352-2 may be releasable secured to each other. In implementations, the second shell portion 352-2 may be omitted from the shell 350.

The assembly 349 may include a handle 356 configured for manipulation by the surgeon or assistant to situate the shell 350 in a desired position and/or orientation. The handle 356 may extend outwardly from a shell body 351 of the shell 350. The handle 356 may extend outwardly from the first shell portion 352-1.

The shell 250 may include a cavity 253 dimensioned to capture and resect a portion of bone B, such as a coracoid process of a patient. Each shell portion 352-1, 352-2 may include a recess 352R. The recesses 352R of the shell portions 352-1, 352-2 may cooperate to establish the cavity 353.

Figure 21:
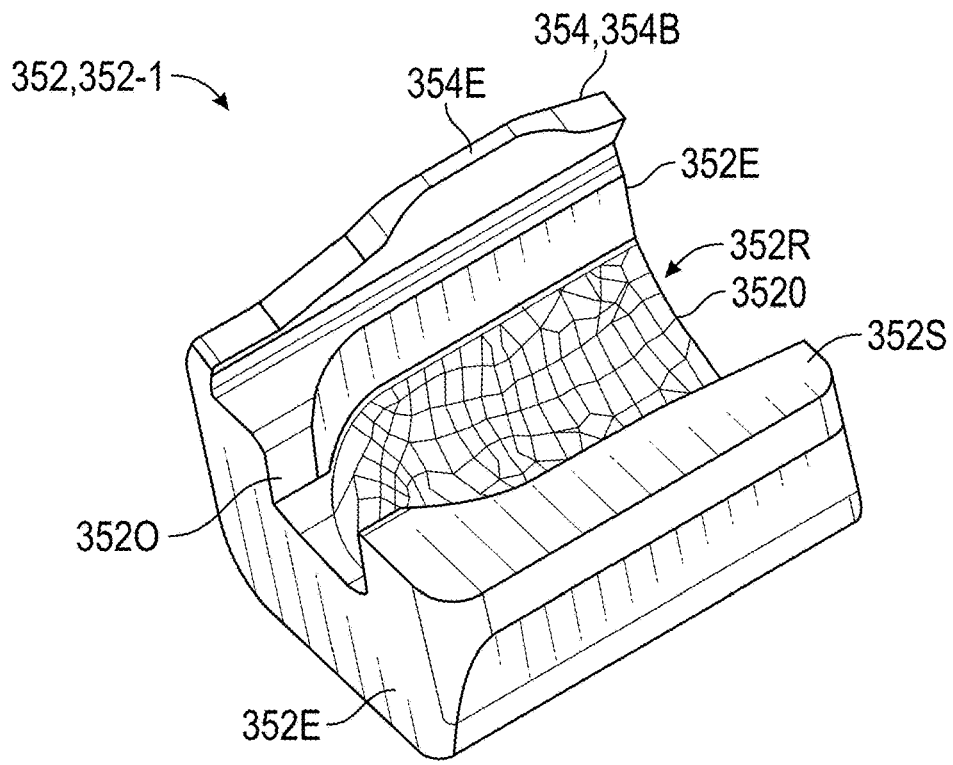
Figure 22:
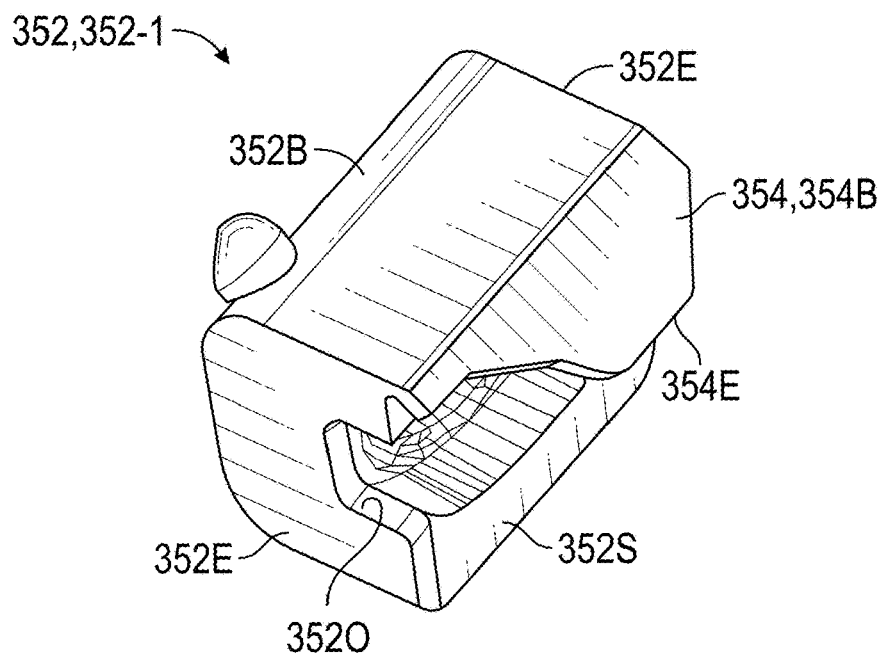
Figure 23:
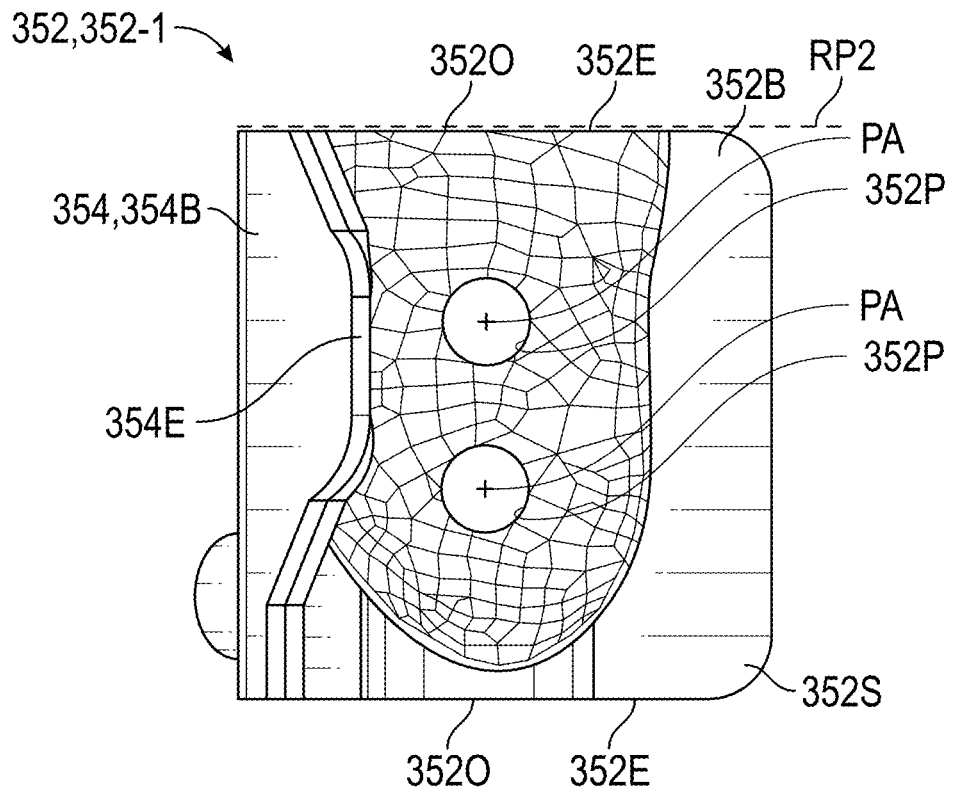
Figure 24:
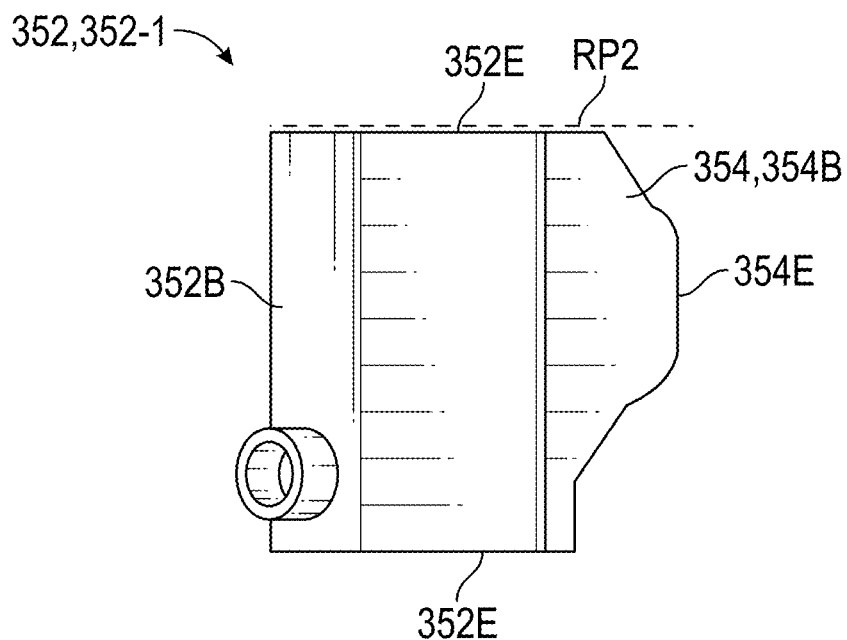

Referring to FIGS. 21-23, with continuing reference to FIG. 20, the recess 352R may extend inwardly from a sidewall (e.g., first resection surface) 352S of the shell portion 352. Surfaces of the cavity 353 and associated recess(es) 352R may be dimensioned according to a first patient-specific contour PC-1 (see, e.g., FIGS. 9, 20 and 27-30). The first patient-specific contour PC-1 may be associated with a surface contour of an outer periphery of the bone B, such as a coracoid process of a patient. The bone B may be associated with the selected graft model 130 (see, e.g., FIG. 13). The shell portions 352-1, 352-2 may be dimensioned to capture the bone B associated with the first patient-specific contour PC-1 within the cavity 353.

Figure 25:
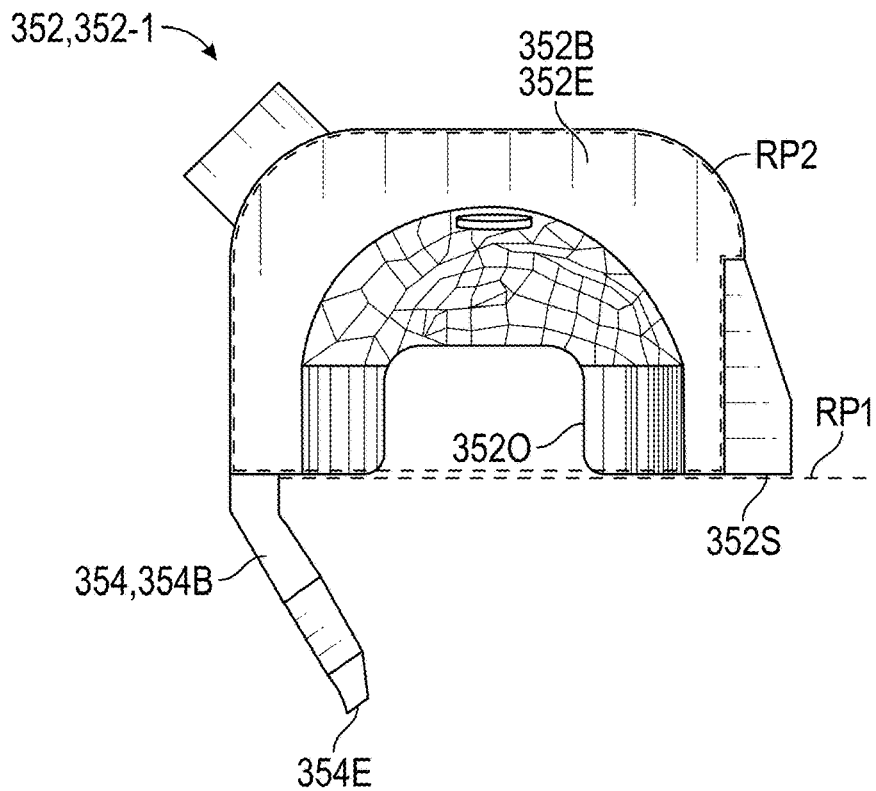
Figure 28:
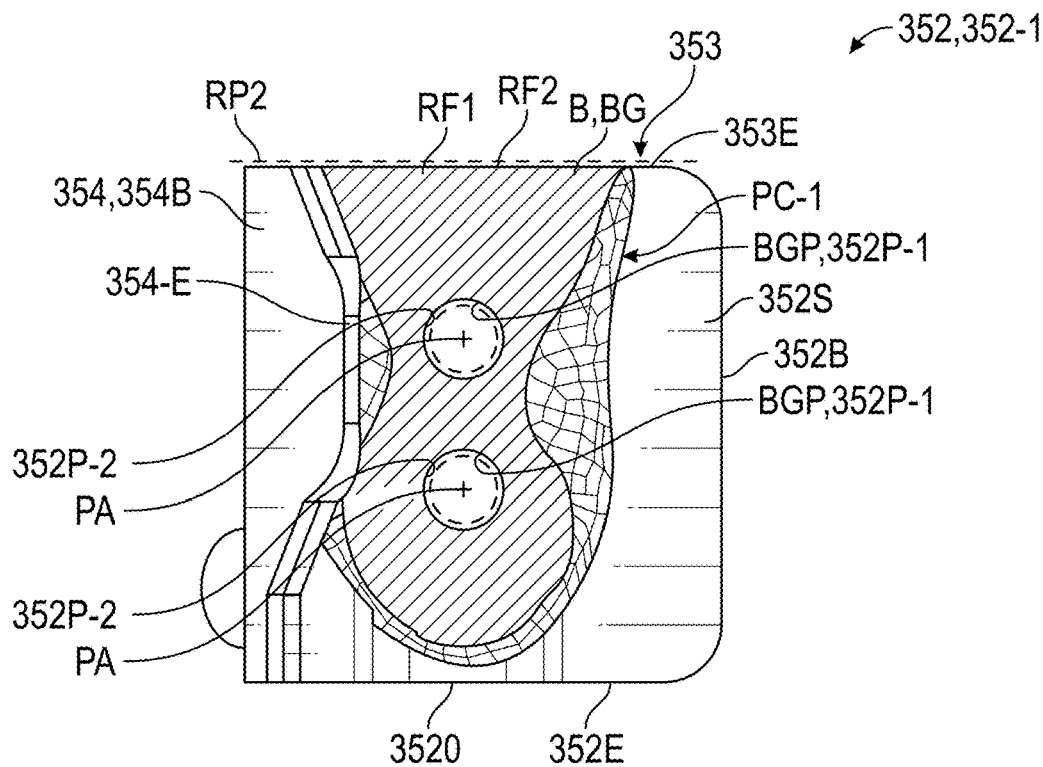
Figure 29:
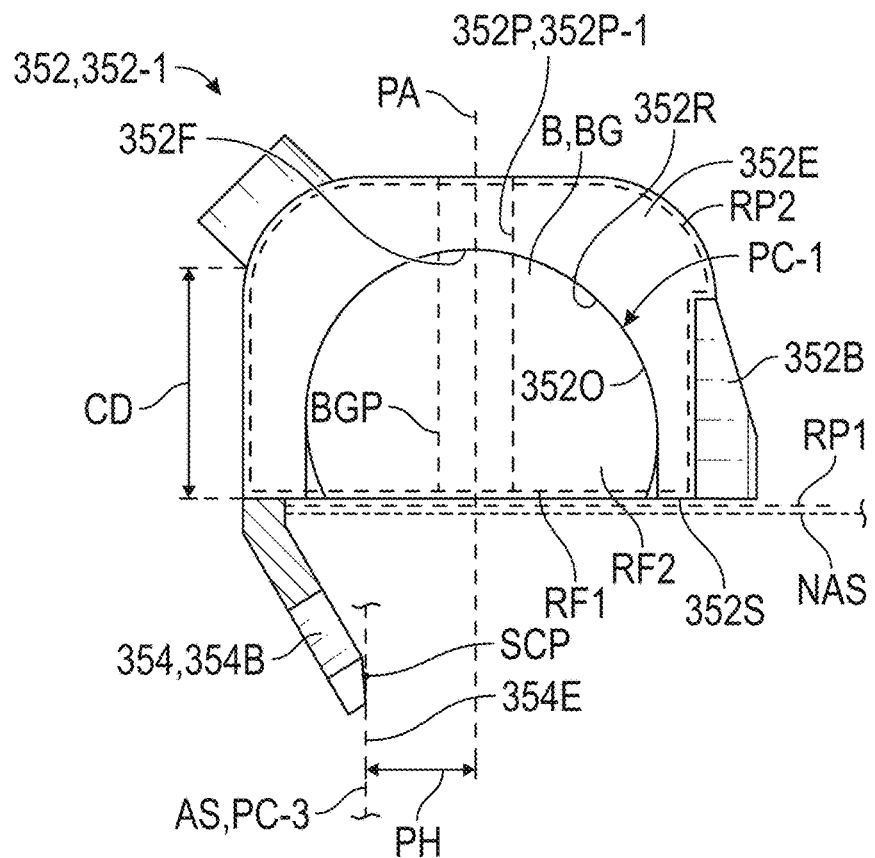
Figure 30:
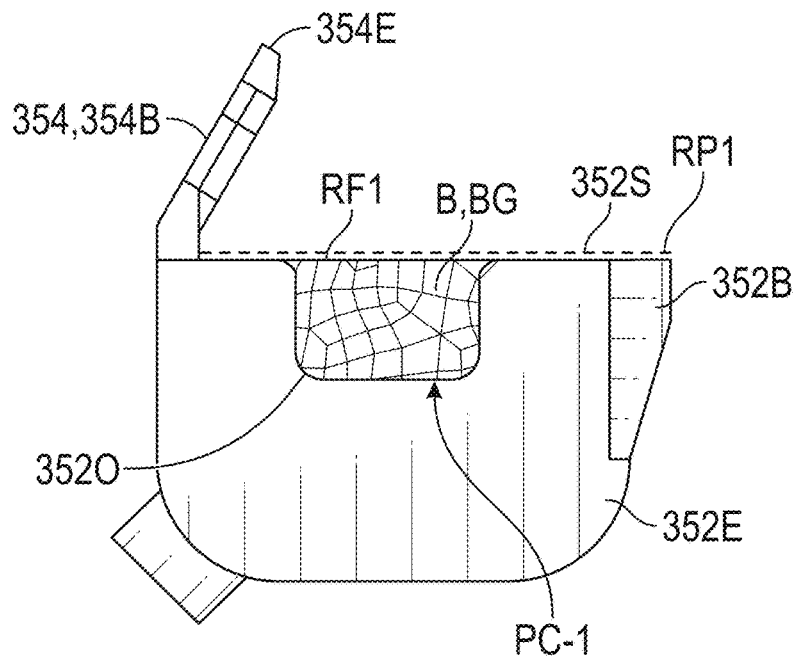

The sidewall 352S of the first shell portion 352-1 may establish a first resection plane RP1 (e.g., FIGS. 25 and 29-30). One or more end walls (e.g., second resection surfaces) 352E of the shell portions 352 may establish a second resection plane RP2 (e.g., FIGS. 23-26 and 28-29). Adjacent end wall(s) 352E of the shell portions 352-1, 352-2 may cooperate to establish the second resection plane RP2 in the assembled position. The second resection plane RP2 may be associated with a second patient-specific contour PC-2 (e.g., FIGS. 7B and 10). The first and second patient-specific contours may be associated with the same bone and/or patient, such as a shoulder of the patient. The first patient-specific contour PC-1 may be associated with a coracoid process of the patient. The second patient-specific contour PC-2 may be associated with another bone, or another portion of the same bone associated with the bone graft BG. The second patient-specific contour PC-2 may be associated with a dimension of a bone loss region, such as an anterior surface of a glenoid (e.g., FIG. 7B).

The first resection plane RP1 may be dimensioned to establish a first (e.g., cavity) depth CD (FIG. 29). The first depth CD may be established between a floor 352F of the recess 352R and a first resection surface established along the sidewall 352S of the first shell portion 352-1. The first depth CD may be associated with a dimension of another bone than a bone associated with bone loss region BLR, or another portion of the same bone, such as a coracoid process of the shoulder.

Referring to FIGS. 21-25, with continuing reference to FIG. 20, the assembly 349 may include at least one outrigger (e.g., flange) 354. The outrigger 354 may be dimensioned according to any of the techniques disclosed herein. The outrigger 354 may include a main body 354B dimensioned to extend outwardly from one of the shell portions 352, such as the first shell portion 352-1, to a free end 354E. The outrigger 354 may extend transversely from the first shell portion 352-1 such that the second shell portion 352-2 may be positioned between the sidewall 352S of the first shell portion 352-1 and the free end 354E of the outrigger 354 in the assembled position, as illustrated in FIG. 20.

Referring to FIG. 29, with continuing reference to FIGS. 20-25, the free end 354E of the outrigger 354 may be dimensioned to contact an articular surface AS of a bone at a surface contact point SCP. The articular surface AS may be established by another bone, or another portion of the same bone associated with the bone graft BG. The articular surface AS may be an articular surface of a bone associated with a selected bone model 129 (e.g., FIG. 17), such as a glenoid face of a glenoid. A (e.g., third) patient-specific contour PC-3 may be associated with the articular surface AS. The outrigger 354 may be dimensioned according to the patient-specific contour PC-3. The outrigger 354 may be dimensioned according to any of the techniques disclosed herein. The third patient-specific contour PC-3 associated with the articular surface AS of a glenoid.

In implementations, a position of the free end 354E of the outrigger 354 at the surface contact point SCP may be established with respect to a passage height PH. The passage height PH may correspond to a distance between the free end 354E of the outrigger 354 and one or more passage axes PA of the passages 352P (see also FIGS. 26 and 28). The passage height PH may be dimensioned utilizing any of the techniques disclosed herein. The sidewall 352S of the first shell portion 352-1 may be dimensioned to abut a non-articular surface NAS of the bone, such as an anterior surface of a glenoid, in response to contact between the free end 354E of the outrigger 354 and the articular surface AS.

Figure 26:
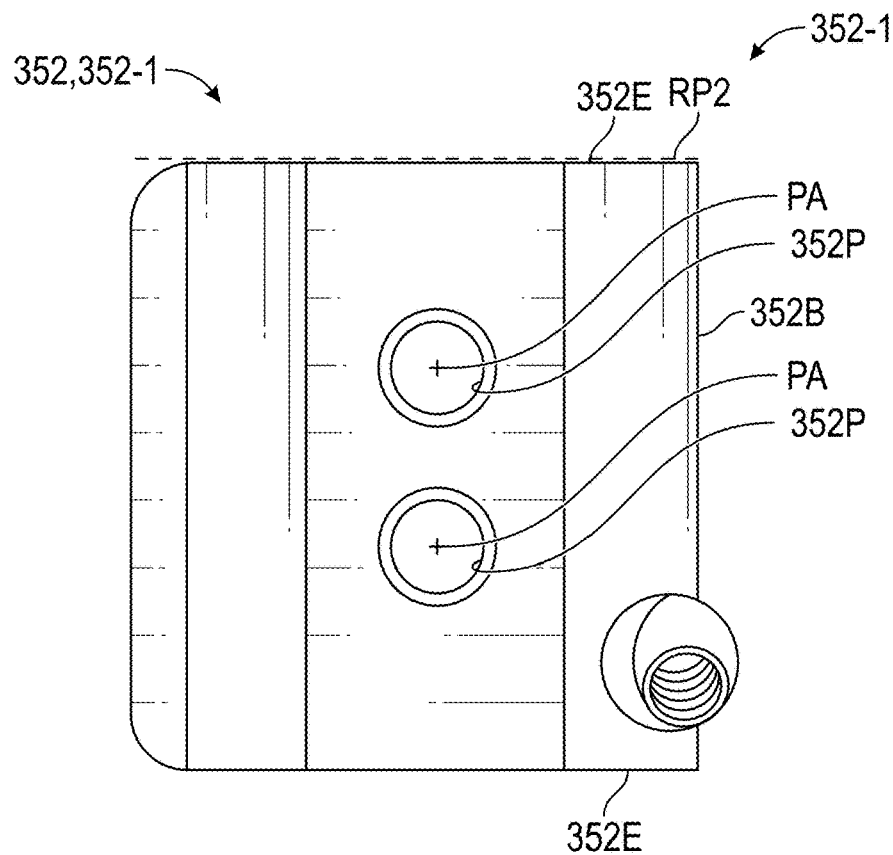
Figure 27:
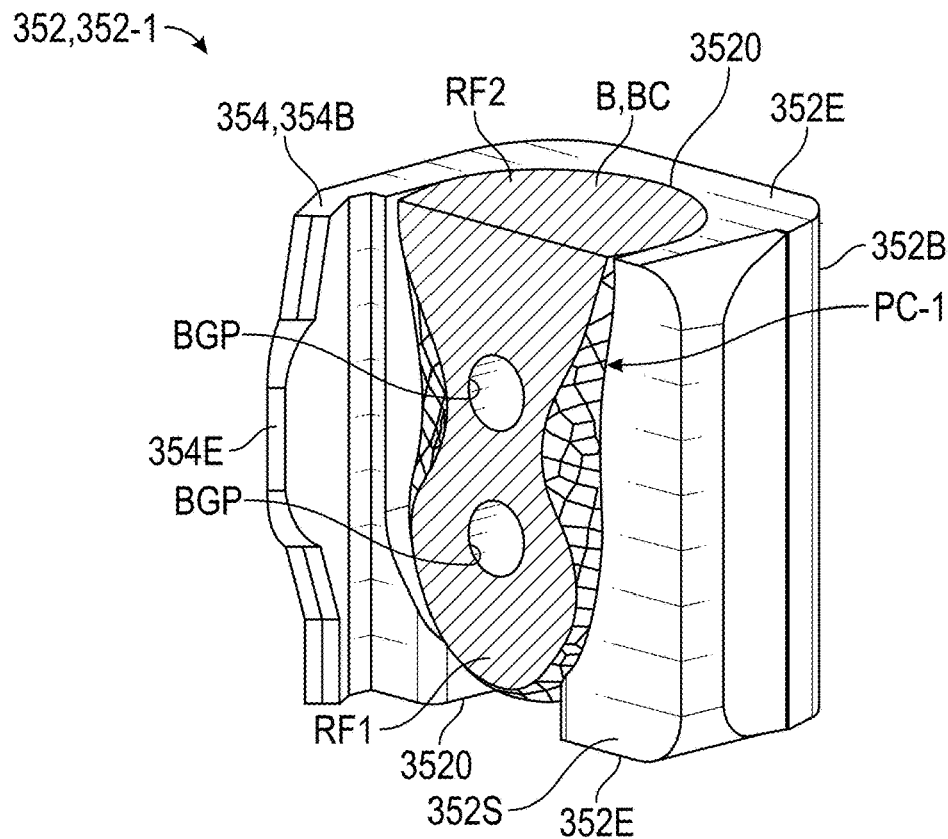

Referring to FIGS. 28-29, with continuing reference to FIGS. 20 and 26-27, the shell portions 352 may include one or more passages 352P. The passages 352P may be utilized to form passages BGP in the bone graft BG. The first shell portion 352-1 may include first passage(s) 352P-1. The second shell portion 352-2 may include second passage(s) 352P-2 (shown in dashed lines in FIG. 28). The passage axes PA of the first and second passages 352P-1, 352P-2 may be substantially aligned in the assembled position such that a guide member (e.g., guide pin), drill bit, fastener and/or other device may be insertable through the passages 352P-1, 352P-2, across the cavity 353, and into the non-articular surface NAS of the bone (FIG. 29).

Figure 31:
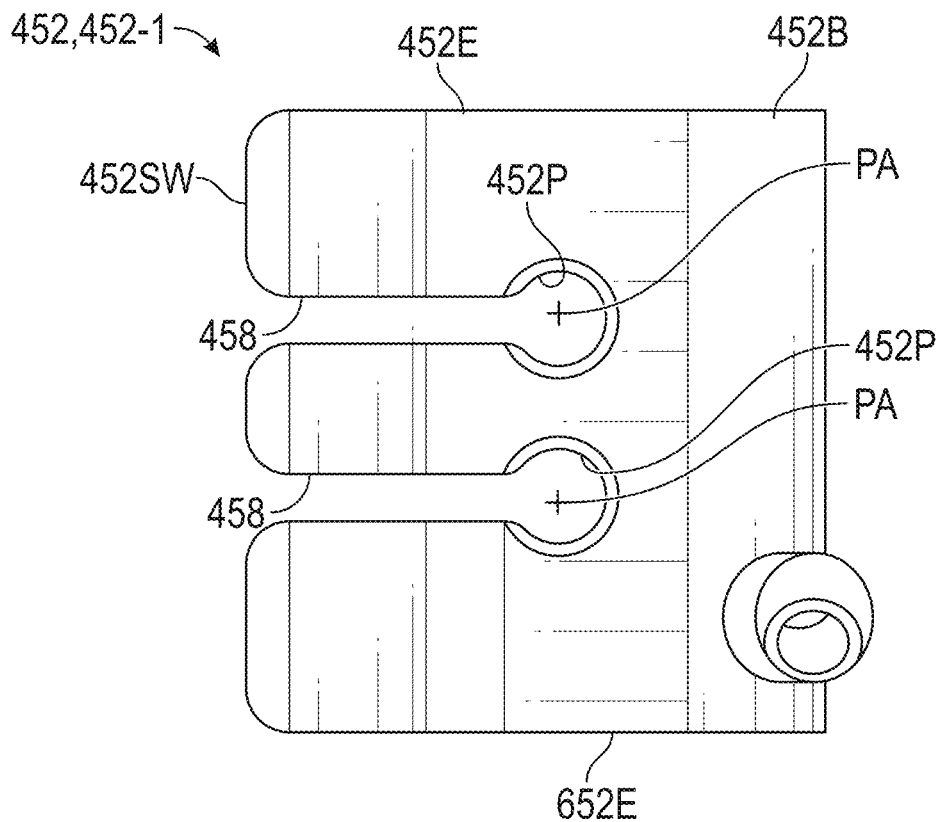
FIGS. 31-36 illustrate features of exemplary shell portions of an assembly.
Figure 32:
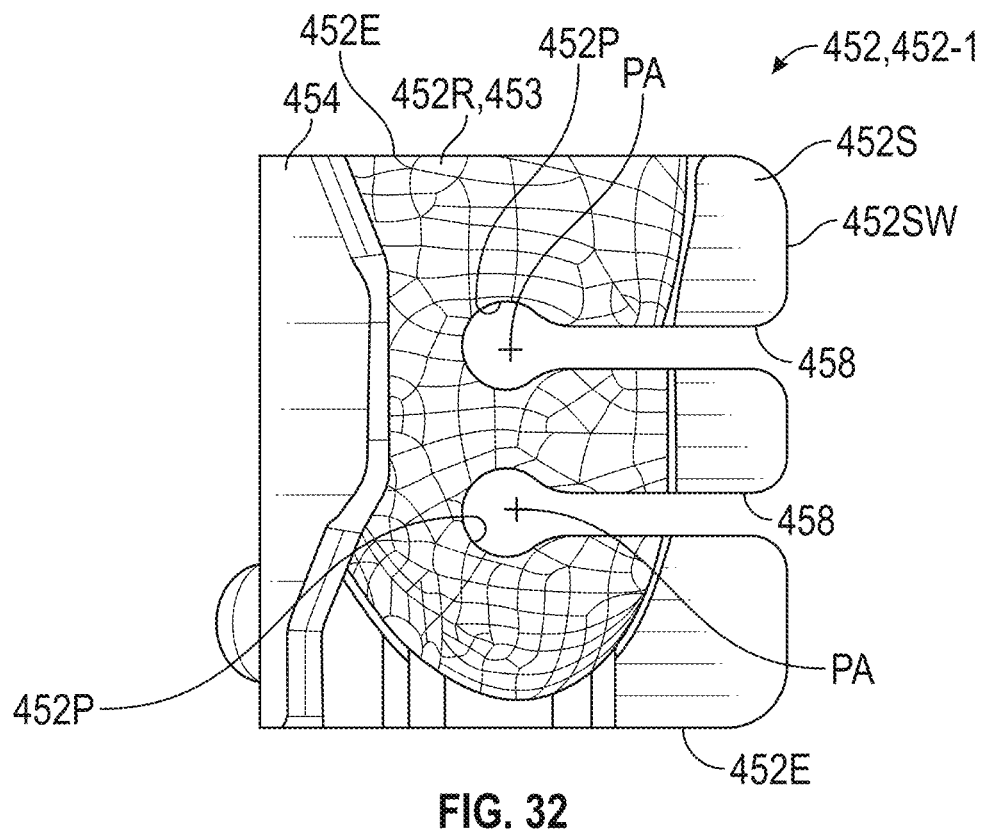

FIGS. 31-32 illustrate another exemplary shell portion 452. The shell portion 452 may be a first shell portion 452-1. A shell (e.g., main) body 452B of the shell portion 452 may include one or more passages 452P. The passages 452P may extend from a recess 452R established by the shell body 452B (FIG. 32).

The shell body 452B may include one or more slots 458. Each slot 458 may extend from a respective one of the passages 452P to a sidewall 452SW of the shell body 452B. The slots 458 may be dimensioned to at least partially receive one or more surgical objects, such as suture and other tissue securing members, for passing the surgical objects to and/or from the passages 452P.

Figure 33:
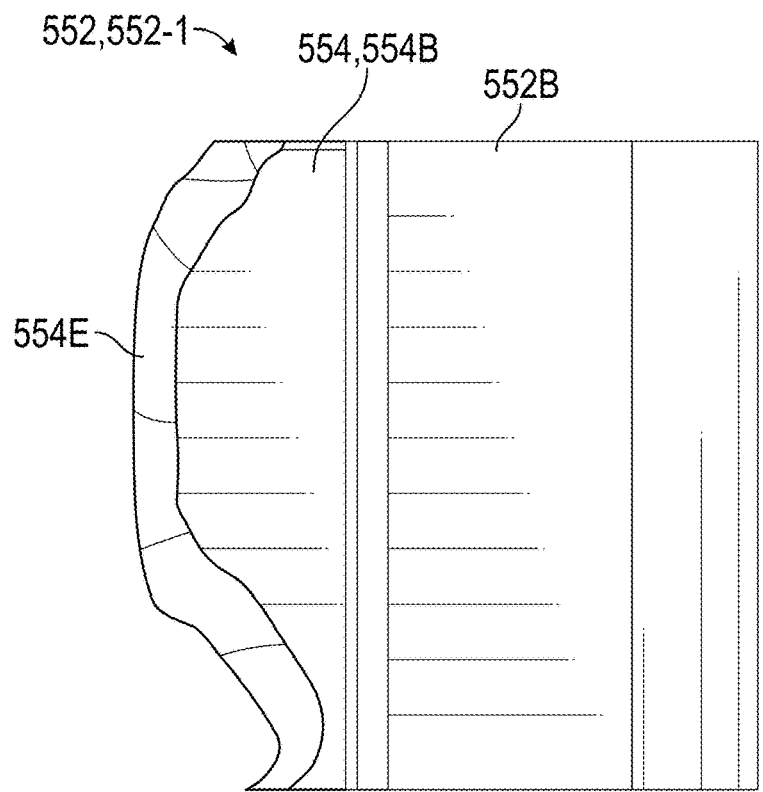
Figure 34:
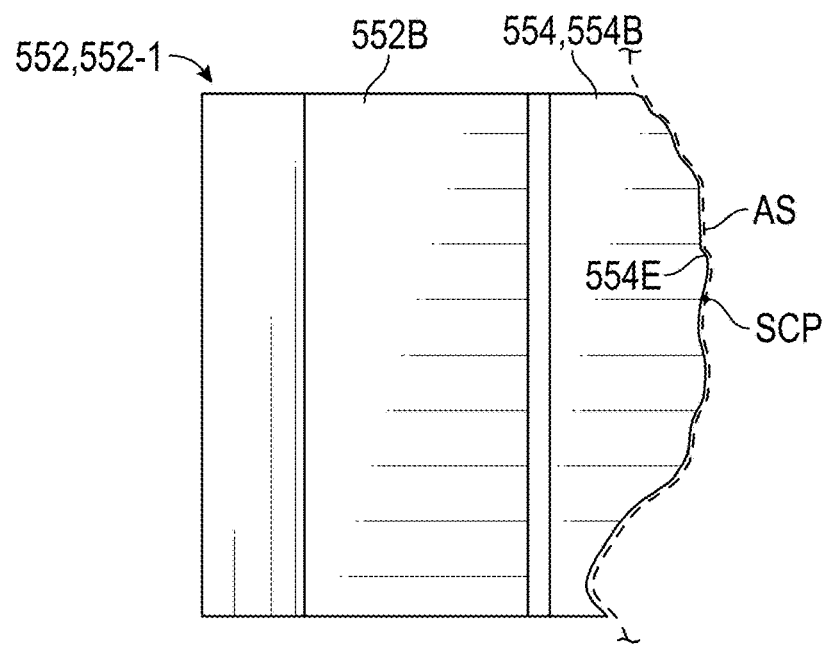

FIGS. 33-34 illustrate another exemplary shell portion 552. The shell portion 552 may be a first shell portion 552-1. An outrigger (e.g., flange) 554 may extend outwardly from a shell (e.g., main) body 552B to a free end 554E. A surface profile of the free end 554E may be dimensioned according to a patient-specific contour associated with an articular surface AS at a surface contact point SCP. The articular surface AS may be a glenoid face of a glenoid.

Figure 35:
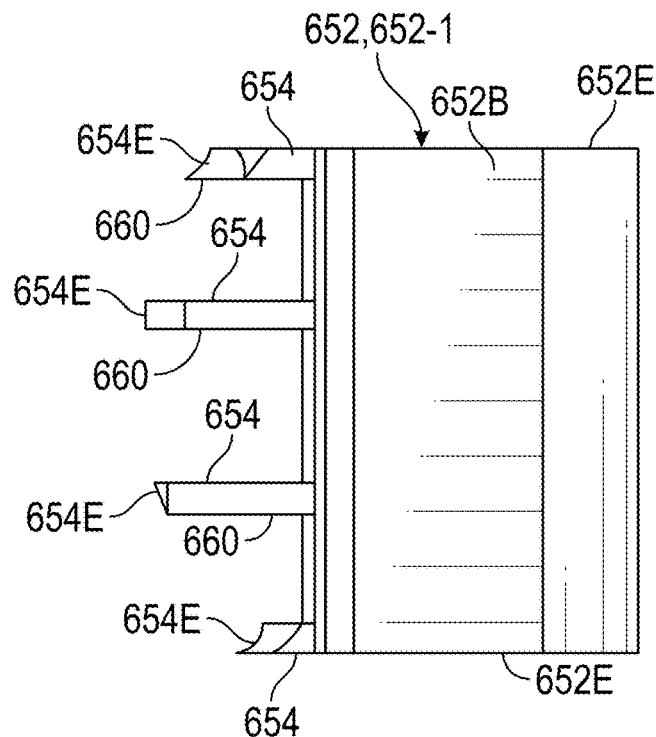
Figure 36:
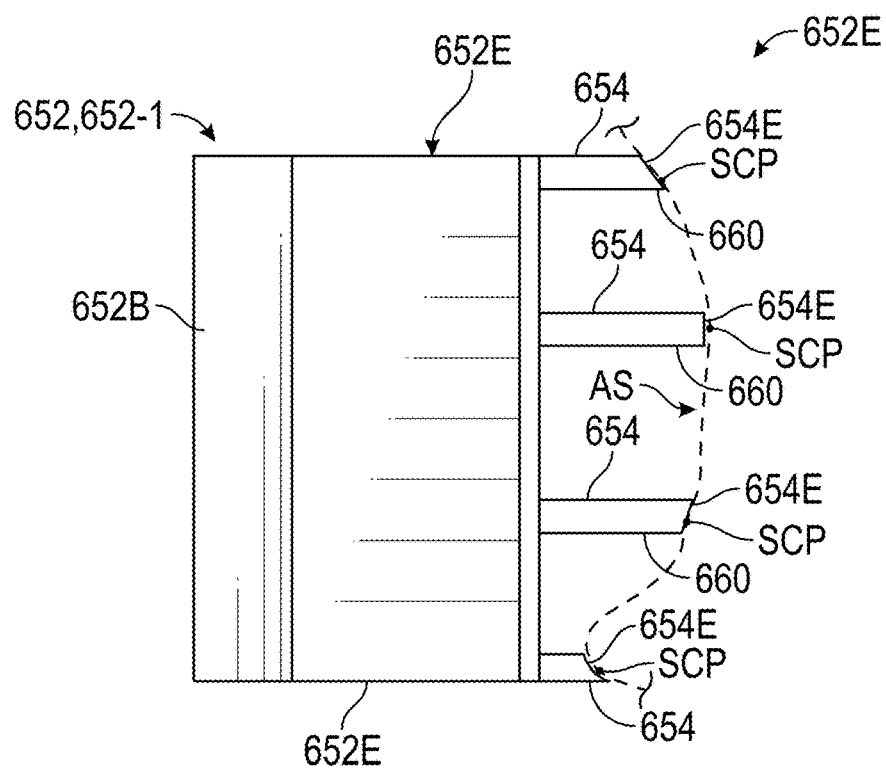

FIGS. 35-36 illustrate another exemplary shell portion 652. The shell portion 652 may be a first shell portion 652-1. The shell portion 652 may include two or more outriggers (e.g., flanges) 654. Each outrigger 654 may extend outwardly from a shell (e.g., main) body 652B to a free end 654E. Adjacent outriggers 654 may establish respective slots 660. Each slot 660 may extend outwardly from the shell body 652B. The free ends 654E may be dimensioned to contact an articular surface AS at respective (e.g., individual) surface contact points SCP. A surface profile of each free end 654E may be dimensioned according to a patient-specific contour associated with the articular surface AS at the respective surface contact point SCP. The articular surface AS may be a glenoid face of a glenoid.

Figure 37:
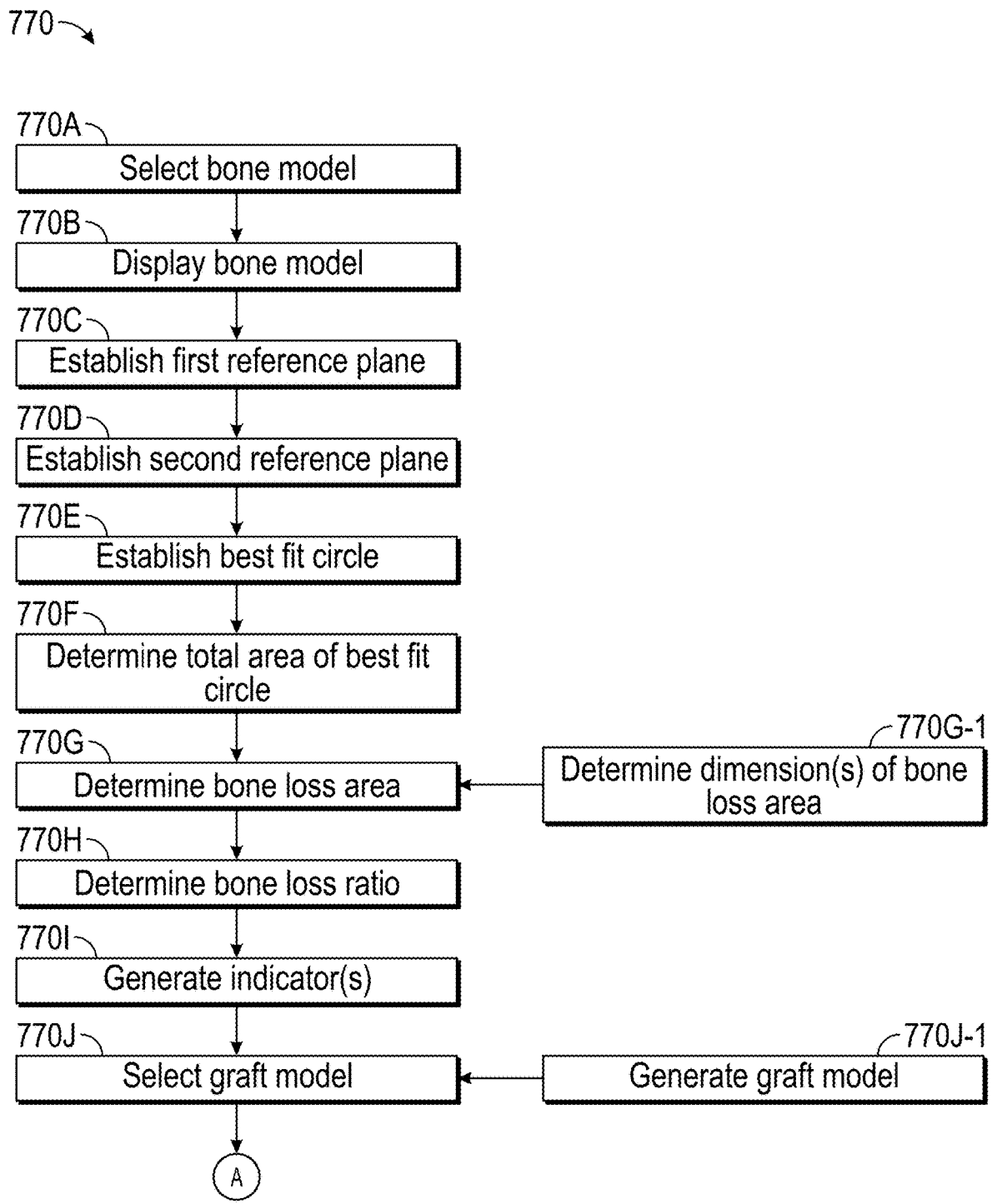
FIG. 37 illustrates an exemplary method of planning and executing an orthopaedic procedure.
Figure 37:
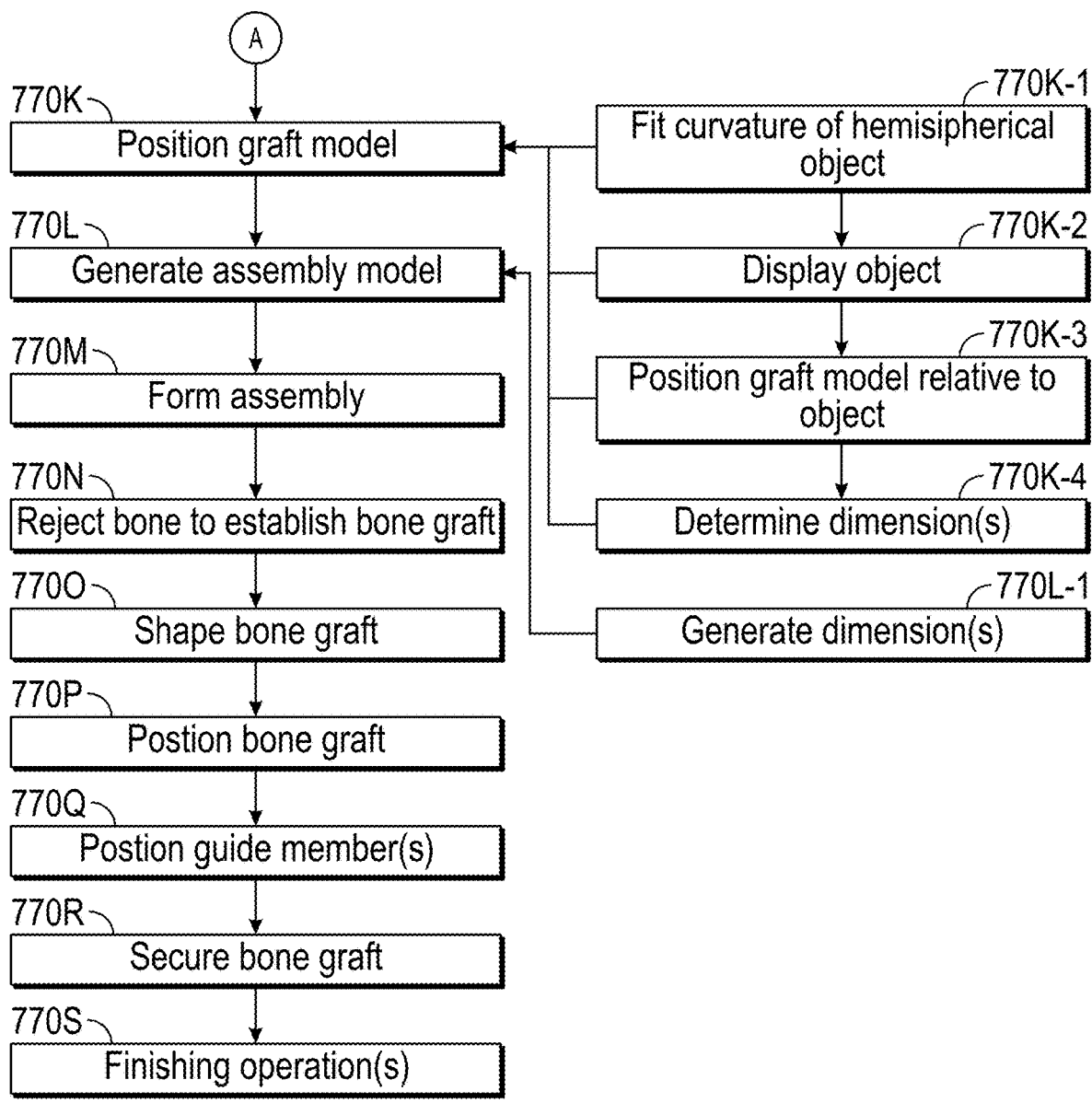

FIG. 37 illustrates an exemplary method of planning and performing an orthopaedic procedure in a flowchart 770. The method 770 may be utilized to pre-operatively plan and perform an arthroplasty for restoring functionality to shoulders, ankles, knees, hips and other joints having bone loss or erosion along articular surfaces of the joint. The method 770 may be utilized with any of the instrumentation and assembly models disclosed herein, including the guide assemblies 249, 349, shells 150, 250, 350, 450, 550, 650, and/or assembly models 141. The method 770 may be utilized to determine or estimate an amount of bone loss along a surface of bone, and may be utilized to dimension one or more assemblies and other instruments based on the determined amount of bone loss. The method 770 may be utilized to generate one or more dimensions associated with instruments for performing an orthopaedic procedure according to an associated surgical plan for a patient. The dimensions may be utilized to fabricate or otherwise form an instrument, which may have one or more patient-specific surfaces and/or other dimensions associated with the surgical plan for a patient. Fewer or additional steps than are recited below could be performed within the scope of this disclosure, and the recited order of steps is not intended to limit this disclosure. Reference is made to the system 120 and user interface 142 for illustrative purposes.

Referring to FIG. 3, with continuing reference to FIG. 37, at least one bone model 129 may be selected at step 770A. The bone model 129 may be selected in response to user interaction with the graphical user interface 142. The bone model 129 may be a shoulder model 129S associated with a shoulder of a patient. At step 770B, the selected bone model 129 may be displayed in the graphical user interface 142 of the planning environment 126.

Referring to FIGS. 3-4, with continuing reference to FIG. 37, a first (e.g., vertical) reference plane REF1 may be established at step 770C. The first plane REF1 may extend through a first position P1 along a trigonum spinae 129TS, a second position P2 along the articular surface 129AS, and a third position P3 along an inferior angle 129IA of a shoulder model 129S in the planning environment 126. The shoulder model 129S may be associated with a shoulder of a patient.

At step 770D, a second (e.g., superior-inferior) plane REF2 may be established. The second plane REF2 may extend through the positions P1, P2 of the trigonum spinae 129TS and articular surface 129AS and a fourth position P4. The second plane REF2 may be oriented at a first angle α relative to the first plane REF1 such that the second plane REF2 extends along a surface of a superior angle 129SA of the selected shoulder model 129S at the second position P4.

The selected bone model 129 may be displayed in the user interface 142 such that each of the first and second planes REF1, REF2 intersects two respective points along a perimeter of an articular surface 129AS of the bone model 129, such as a perimeter of the glenoid face 129GF. Displaying the bone model 129 at step 770B may include displaying a transparency of the bone model 129 in the graphical user interface 142. The transparency may include the glenoid face 129GF overlaying the trigonum spinae 129TS and/or the glenoid face 129GF overlaying a portion of the superior angle 129SA of the shoulder model 129S, as illustrated in FIGS. 4-5.

Referring to FIG. 6, with continuing reference to FIG. 37, at step 770E a best fit circle BFC may be established along the articular surface 129AS, such as the glenoid face 129GF of the shoulder model 129S. A center BCP of the best fit circle BFC may be established along the second plane REF2.

Referring to FIGS. 7A-7B, with continuing reference to FIG. 37, at step 770F a total area A1 established by the best fit circle BFC may be determined. The total area A1 may include at least a portion of the articular surface 129AS, including the glenoid face 129GF.

At step 770G, a bone loss area A2 associated with a bone loss region BLR may be determined. The bone loss area A2 may be established between a perimeter of the best fit circle BFC and a segment S1 associated with the articular surface 129AS. The segment S1 may be an anterior segment associated with a perimeter of the glenoid face 129GF.

At step 770G-1, one or more dimensions associated with the bone loss area A2 of the bone loss region BLR may be determined. Step 770G-1 may include determining a width WB and/or length LB of the bone loss area A2 (FIG. 7A). The length LB of the bone loss area A2 may be established between ends of a segment S1, which may be an anterior segment of the articular surface 129AS.

At step 770H, a bone loss ratio A2:A1 may be determined. The bone loss ratio A2:A1 may be defined as the bone loss area A2 divided by the total area A1. Various techniques may be utilized to determine the first and second planes REF1, REF2, best fit circle BFC, areas A1, A2 and/or other aspects associated with the bone loss region BLR, including any of the techniques disclosed herein.

At step 770I, one or more indicators PI may be generated. The indicators PI may be associated with the bone loss ratio A2:A1. The indicators PI may be generated based on any of the predetermined criteria disclosed herein, including one or more predefined thresholds. The indicators PI may include value indicators PV associated with values of the determined areas A1, A2 and/or bone loss ratio A2:A1. The value indicators PV may be incorporated into one or more graphics 146G.

Referring to FIGS. 8-9, with continuing reference to FIG. 37, at least one bone graft model 130 may be selected at step 770J. At step 770J-1, the graft model 130 may be generated or established. The graft model 130 may be associated with a portion of a bone represented by the selected bone model 129, or may be another bone including another bone of the patient. The graft model 130 may be associated with a coracoid process 129CP of the shoulder model 129S. The graft model 130 may be dimensioned according to any of the techniques disclosed herein.

Referring to FIGS. 10-11, with continuing reference to FIG. 37, at step 770K the graft model 130 may be positioned relative to the selected bone model 129. The graft model 130 may be positioned in abutment with a non-articular surface NAS of the bone model 129. A bone portion associated with the graft model 130 may be utilized to reestablish a portion of the articular surface associated with the articular surface 129AS that may have been eroded or degraded at the bone loss region BLR.

Various techniques may be utilized to position the graft model 130. At step 770K-1, a curvature of a guidance (e.g., positioning) object such as hemispherical object 148 may be fit relative to a curvature of the articular surface 129AS. The articular surface 129AS may be the glenoid face 129GF of the shoulder model 129S. At step 770K-2, the hemispherical object 148 may be displayed relative to the articular surface 129AS of the bone model 129, which may occur prior to, during and/or subsequent to fitting the hemispherical object 148 at step 770K-1.

At step 770K-3, the graft model 130 may be positioned in a first volume V1 associated with the bone loss area A2 at the bone loss region BLR. The graft model 130 may be moved in directions D1, D2 and/or D3 to position the graft model 130 relative to the bone model 129. Step 770K-3 may occur such that a boundary of the graft model 130 may be substantially aligned with the curvature of the hemispherical object 148 at a boundary point BP, as illustrated in FIG. 11.

Referring to FIG. 12, with continuing reference to FIG. 37, step 770K-3 may include setting a position and orientation of one or more fastener axes FA. Each fastener axis FA may be associated with a selected fastener model 147.

At step 770K-4, one or more dimensions may be determined based on the positioning of the graft model 130 relative to the articular surface 129AS and/or hemispherical object 148 at step 770K-3. Step 770K-4 may include determining a height HB associated with the bone loss area A2. The height HB may be a distance between the boundary point BP and the fastener axis FA.

Step 770K-4 may include determining an outrigger height (e.g., distance) OH between the boundary point BP and a point along the articular surface 129AS, such as a surface contact point SCP (see FIG. 16). The distance may be established such that the bone graft 130 is situated lateral or otherwise outward of the point SCP along the articular surface 129AS. The outrigger height OH may be established such that the graft model 130 is substantially flush with a contour of the articular surface 129AS.

Referring to FIGS. 13-17, with continuing reference to FIG. 37, at step 770L a (e.g., guide) assembly model 141 may be generated. Features of the assembly model 141 are illustrated in FIGS. 14-17. Step 770L may occur in the planning environment 126. At step 770L-1, one or more dimensions associated with the assembly model 141 may be generated based on aspects of the bone loss region BLR including the bone loss area A2 (FIGS. 7A-7B). The assembly model 141 may be dimensioned according to one or more patient-specific contours associated with the selected bone model 129 and/or selected graft model 130. The assembly model 141 may be dimensioned utilizing any of the techniques disclosed herein.

At step 770M, a physical (e.g., guide) assembly may be fabricated or otherwise formed according to the assembly model 141. The assembly can include any of the assemblies and components disclosed herein, including assemblies 249, 349, 749 and shells 150, 250, 350, 450, 550, 650, 750.

Figure 38:
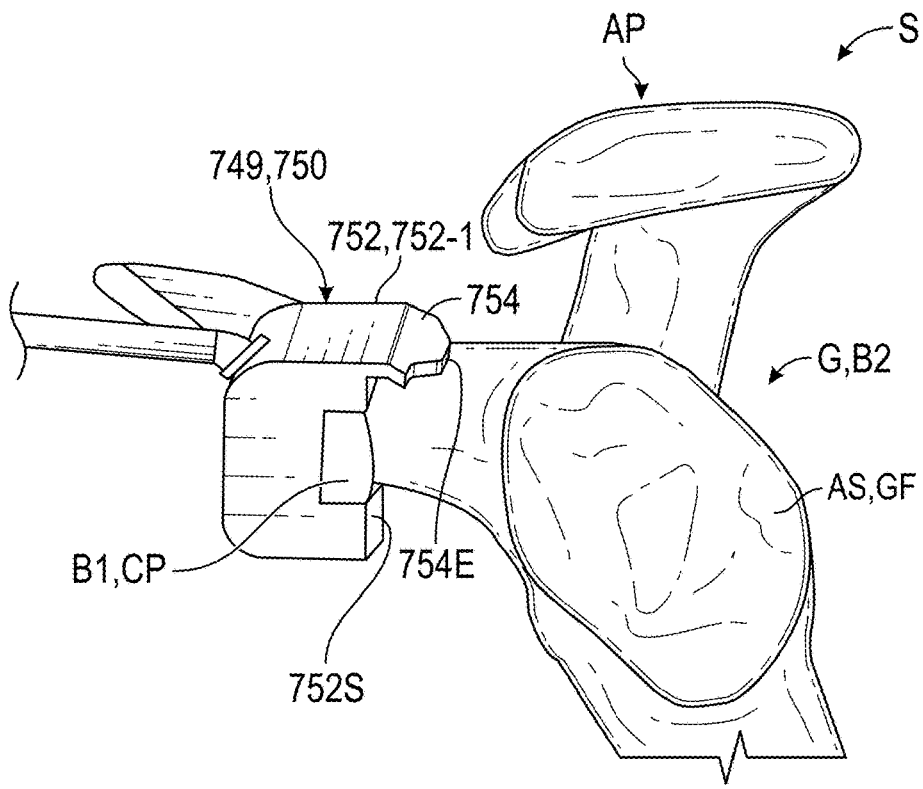
FIGS. 38-39 illustrate an assembly capturing a coracoid process.
Figure 39:
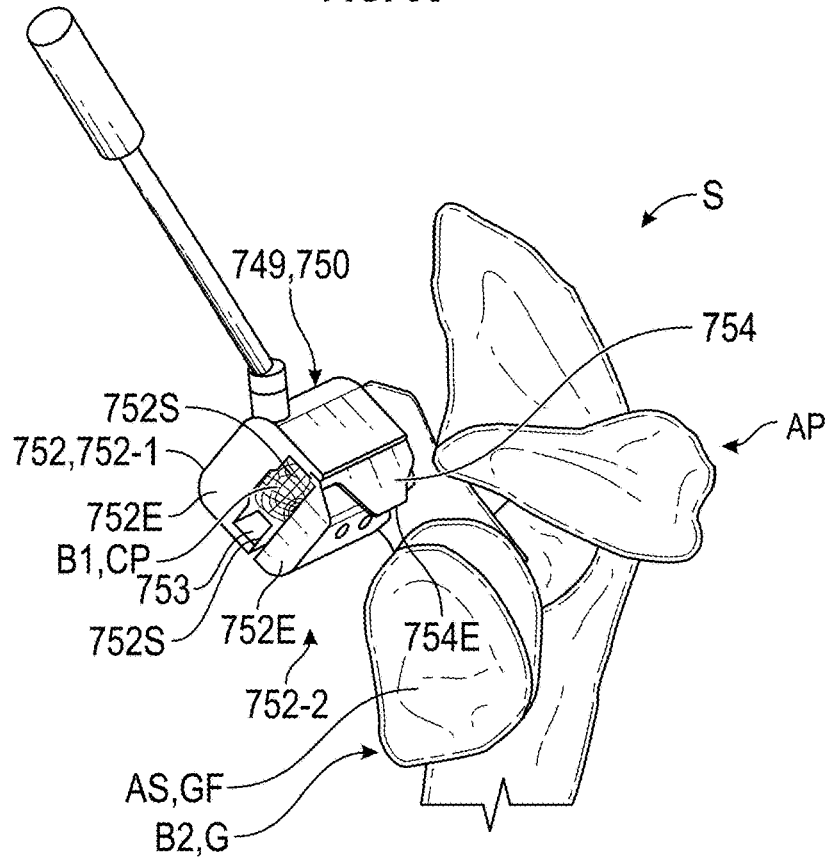

Referring to FIG. 38, with continuing reference to FIG. 37, step 770M may include fabricating or otherwise forming the assembly 749. The assembly 749 may include a shell 750 having a first shell portion 752-1 and a second shell portion 752-2 that cooperate to establish a cavity 753 in an assembled position (FIG. 39). The shell portions 752-1, 752-2 may be dimensioned to capture a portion of a bone B1 in the cavity 753 in the assembled position. The captured bone B1 may be the coracoid process CP of a shoulder S. The shoulder S may include an acromion process AP and a glenoid G including an articular surface AS established by a glenoid face GF. The cavity 753 may be dimensioned according to any of the techniques disclosed herein. In implementations, the cavity 753 may be dimensioned according to a first patient-specific contour associated with the coracoid process CP. In implementations, the second shell portion 752-2 may be omitted from the shell 750, and the first shell portion 752-1 may establish the cavity 753. Omitting the second shell portion 752-2 may reduce a complexity of the shell 750 and a complexity of the method 770. Utilizing the second shell portion 752-2 in combination with the first shell portion 752-1 may more securely capture the bone B1, may provide a relatively larger resection surface (see, e.g., second resection plane RP2 of FIG. 18), and may be utilized to more precisely establish passages BPG in the bone graft BG (see, e.g., FIG. 19).

Forming the assembly 749 at step 770M may include forming an outrigger 754. The outrigger 754 may extend outwardly from the first shell portion 752-1 to a free end 754E. The free end 754E may be dimensioned to contact the articular surface AS, such as the glenoid face GF (see, e.g., FIGS. 42-43).

Figure 40:
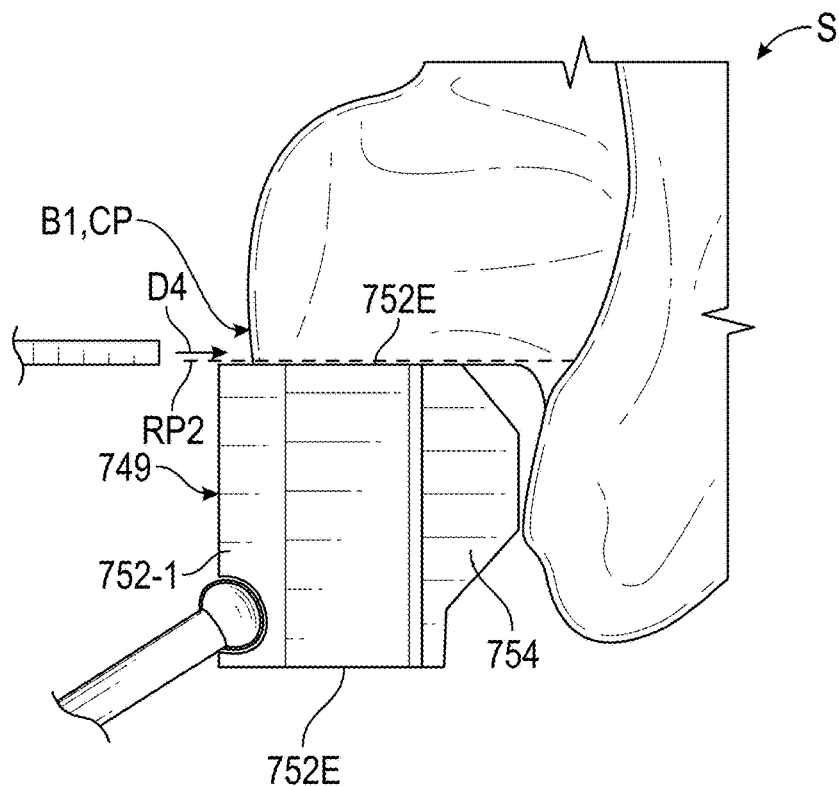
FIG. 40 illustrates performing an osteotomy of the coracoid process of FIGS. 38-39.
Figure 41:
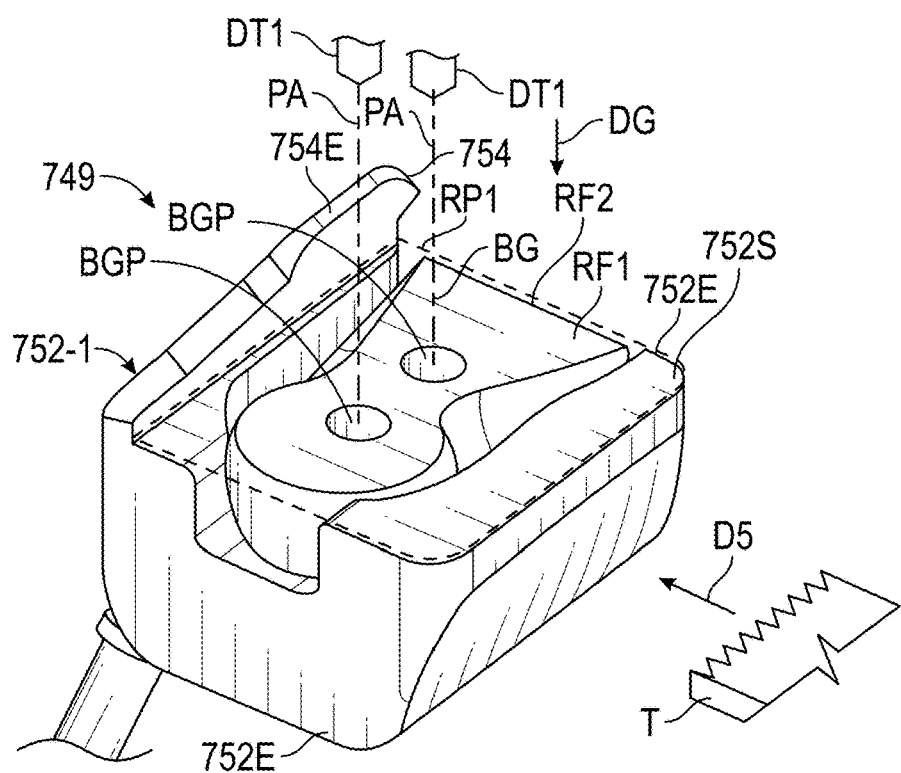
FIG. 41 illustrates shaping a bone graft formed from the coracoid process of FIG. 40.

Referring to FIG. 40, with continuing reference to FIGS. 37-39, at step 770N the portion of bone B1 may be resected to establish a bone graft BG (FIG. 41). One or more end walls 752E of the shell portions 752 may be dimensioned to establish a (e.g., second) resection surface. In implementations, adjacent end walls 752E of the shell portions 752-1, 752-2 may be dimensioned to establish the resection surface in the assembled position. The resection surface established by the end wall(s) 752E may be dimensioned with respect to the determined length LB of the bone loss area A2 (see FIG. 7A). The length LB of the bone loss area A2 may be established between ends of a segment S1, such as an anterior segment associated with the glenoid face GF (see FIGS. 7A and 48).

Step 770N may include moving the first and second shell portions 752-1, 752-2 together to capture a portion of the coracoid process CP in the cavity 753 (FIG. 39). The patient-specific surfaces of the cavity 753 may facilitate positioning and orienting the shell 750 relative to the coracoid process CP, which may improve precision of the resection.

Step 770N may include moving tooling T in a direction D4 and resecting the captured portion of bone B1 along a second resection plane RP2 established by the end wall(s) 752E. Step 770N may include removing a portion of the coracoid process CP to establish the bone graft BG in response to resecting the coracoid process CP along the second resection surface established by the end wall(s) 752E of the shell portions 752. Resecting the captured portion of bone B1 may establish a second resection face RF2 of the bone graft BF (FIG. 41).

Referring to FIG. 41, with continuing reference to FIG. 37, the bone graft GP may be shaped or dimensioned at step 770O. A sidewall 752S along the first shell portion 752-1 may establish a (e.g., first) resection surface. The first resection surface may be dimensioned with respect to the width of a second patient-specific contour. In implementations, the resection surface of the sidewall 752S may be dimensioned with respect to the determined width WB of the bone loss area A2 (FIG. 7A). The second patient-specific contour may be established by a bone loss area A2 bounded by a segment S1 associated with the articular surface AS (FIGS. 7A-7B). The segment S1 may be an anterior segment associated with a glenoid face GF of the patient (see, e.g., FIGS. 7A-7B and 48).

Step 770O may include removing a portion of the bone graft BG to establish a first resection face RF1 in response to resecting the bone graft BG along the first resection surface established by a sidewall 752S. Step 770O may include moving tooling T in a direction D5 and resecting or otherwise removing a portion of the bone graft BG along a first resection plane RP1 established by the sidewall 752S. Resecting the bone graft BG along the first resection plane RP1 may establish the first resection face RF1.

Step 770O may include forming one or more passages BGP through the bone graft BG. The passages BGP may be formed utilizing any of the techniques used herein, including moving tooling DT1 such as a drill bit in a direction D6 along the passage axis PA of a respective passage 752P of the shell portion 752 (see, e.g., FIG. 43).

Figure 42:
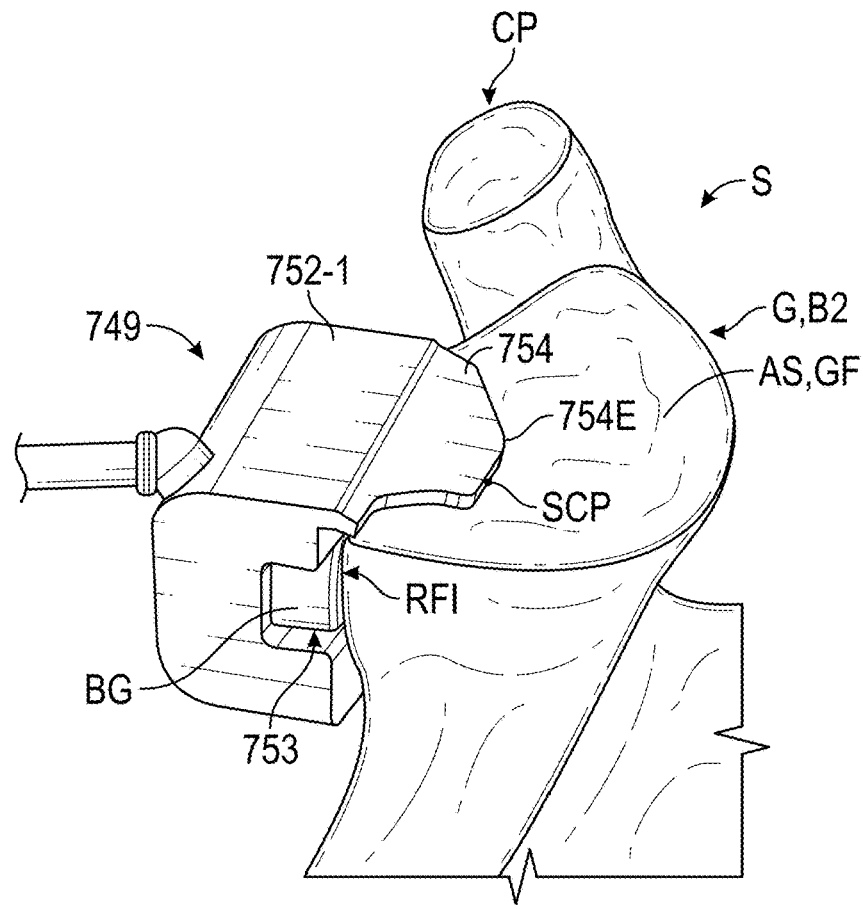
FIGS. 42-45 illustrate positioning the bone graft of FIG. 41 relative to a glenoid.
Figure 43:
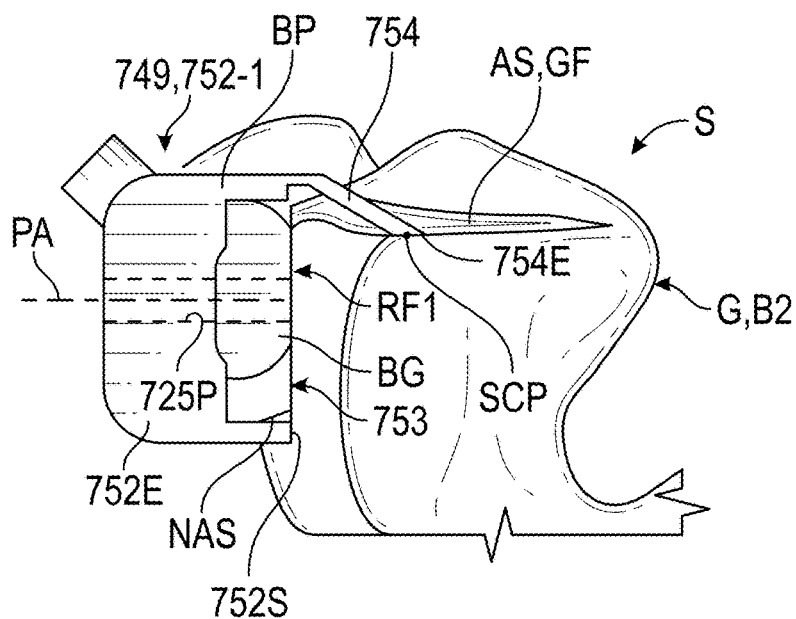
Figure 44:
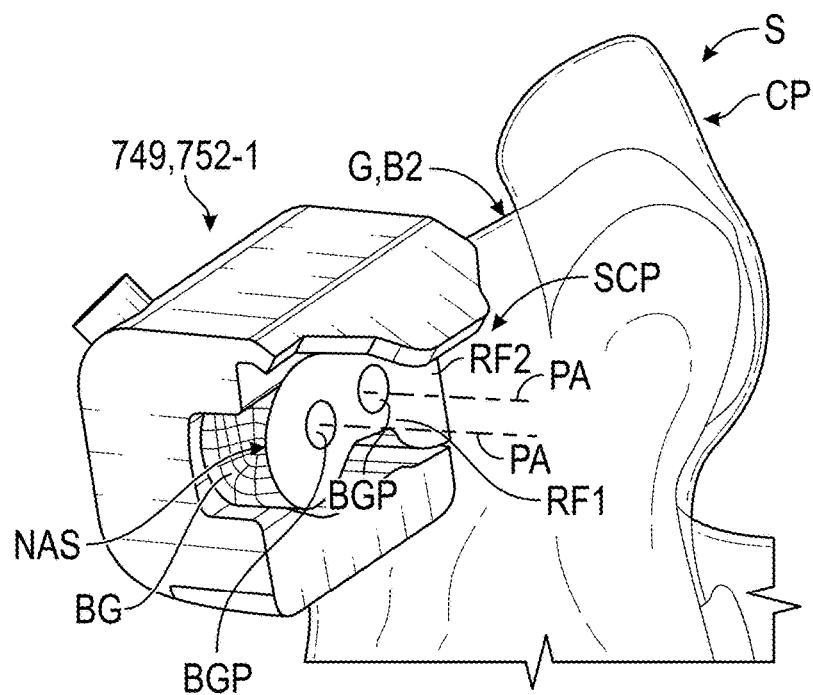

Referring to FIGS. 42-44, with continuing reference to FIG. 37, at step 770P the bone graft BG may be positioned in abutment with another portion of bone B2. The portion of bone B2 may be the glenoid G of the resected shoulder S. The second shell portion 752-2 may be removed from the first shell portion 752-1 prior to step 770P.

Step 770P may include positioning the free end 754E of the outrigger 754 of the first shell portion 752-1 into abutment or contact with the articular surface AS at a surface contact point SCP. Positioning the outrigger 754 may cause the first shell portion 752-1 to seat against the bone B2 at the predetermined position and orientation and may limit rotation and other movement, which may improve positioning of the bone graft BG. The outrigger 754 may be dimensioned according to any of the techniques disclosed herein. Step 770P may occur such that the sidewall 752S of the first shell portion 752-1 and/or the first resection face RF1 of the bone graft BG contact or otherwise oppose a non-articular surface NAS of the portion of bone B2, such as an anterior surface of the glenoid G.

Step 770P may include positioning the free end 754E of the outrigger 754 in abutment with the articular surface AS such as the glenoid face GF such that the resection face RF1 of the bone graft BG abuts a non-articular surface NAS of the portion of bone B2 (FIG. 43), such as an anterior surface of the glenoid G, at a predetermined height relative to the articular surface AS. Positioning the free end 754E of the outrigger 754 may occur such that the first resection surface RP1 of the bone graft BG abuts the anterior surface of the glenoid G.

Figure 45:
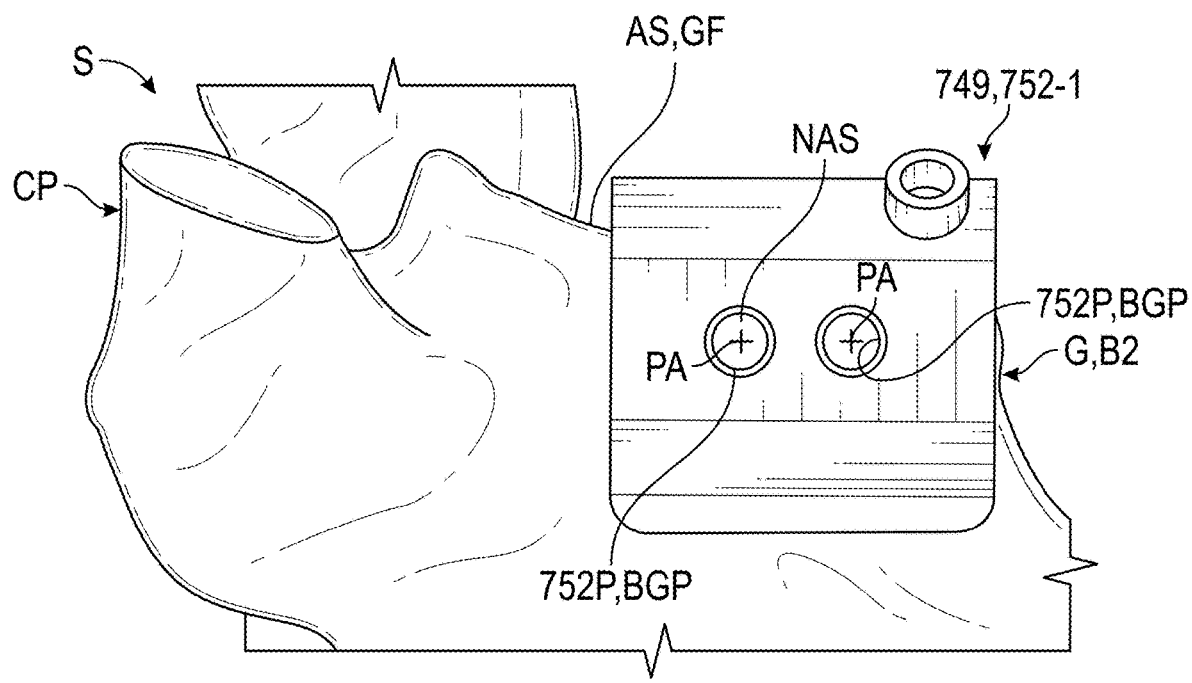

Step 770P may include positioning the first resection surface established by the sidewall 752S of the first shell portion 752-1 in opposition with an anterior surface of the glenoid G such that the resection surface RF1 of the bone graft BG abuts the anterior surface of the glenoid G at the predetermined height. The predetermined height may be established according to any of the techniques disclosed herein, such as with respect to the surface contact point SCP, the boundary point BP (see, e.g., FIGS. 16 and 43) and/or passage axis PA (FIGS. 42-44). Step 770P may occur such that a projection of each passage axis PA may intersect the non-articular surface NAS of the portion of bone B2, as illustrated in FIG. 45.

Figure 46:
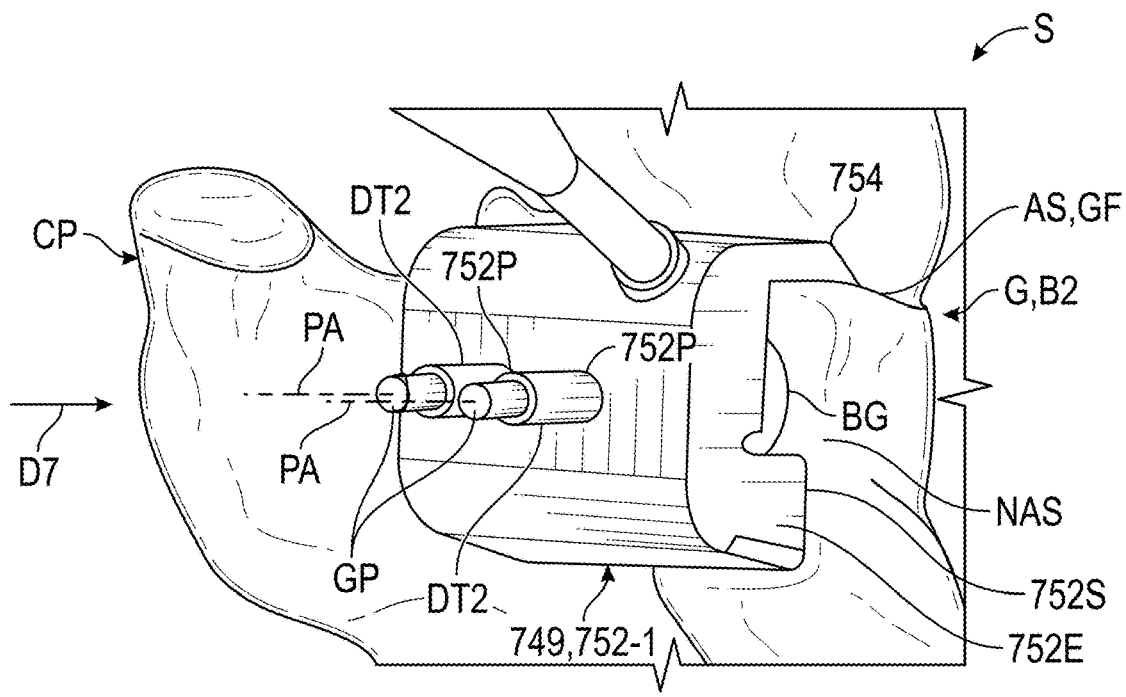
FIGS. 46-47 illustrate positioning guide members in the glenoid with the assembly of FIGS. 42-45.
Figure 47:
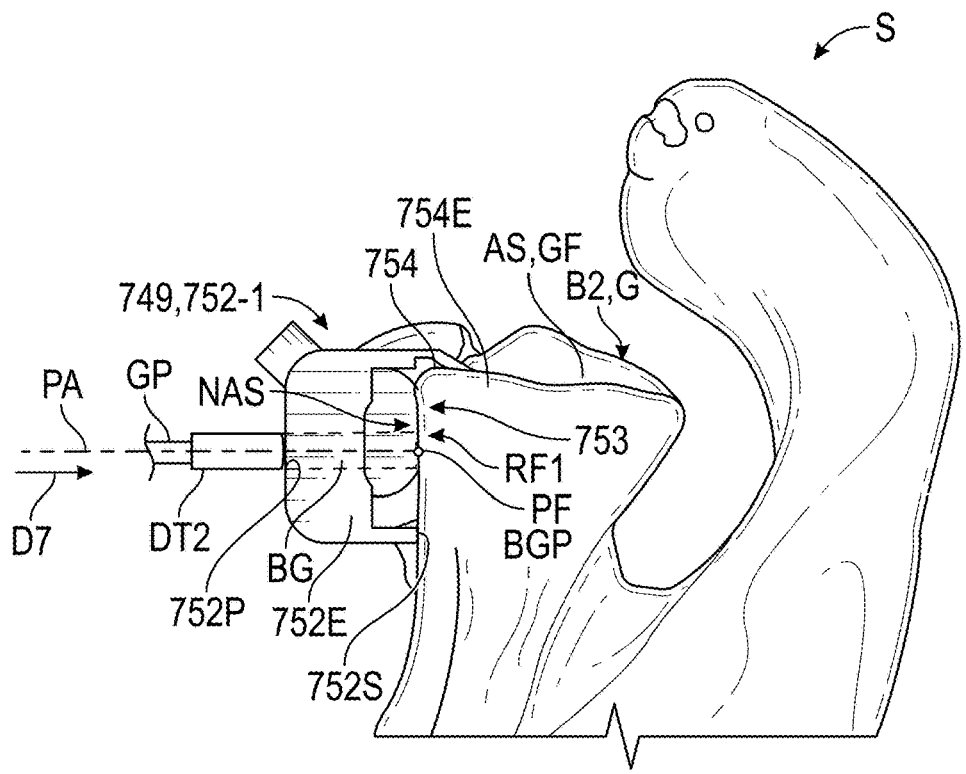

Referring to FIGS. 46-47, with continuing reference to FIG. 37, once the surgeon approves placement of the bone graft BG, one or more guide members such as guide pins GP may be positioned at step 770Q. Step 770Q may include positioning tooling DT2 such as a cannulated driver in the passages 752P of the first shell portion 752-1, through the bone graft passage BGP (shown in dashed lines in FIG. 47), and into the bone B2 to establish one or more pilot holes. The pilot holes may extend through a cortex of the glenoid G. The passages BGP in the bone graft BG may be formed prior to, during or subsequent to positioning the bone graft BG relative to the portion of bone B2.

Step 770Q may include moving each guide pin GP in a direction D7 through the passage 752P in the first shell portion 752-1, through the bone graft passage BGP of the bone graft GP captured in the cavity 753, and then into the non-articular surface NAS of the portion of bone B2 at an insertion point PF (see FIG. 47), such as a point along the anterior surface of the glenoid G. A position of the insertion point PF may be determined utilizing any of the techniques disclosed herein and may be associated with the predetermined height of the bone graft BG. Positioning the free end 754E of the outrigger 754 may occur such that a portion of the bone graft BG is lateral or otherwise outward of the articular surface AS during the step of moving the guide pin GP into the non-articular surface NAS of the portion of bone B2.

Figure 48:
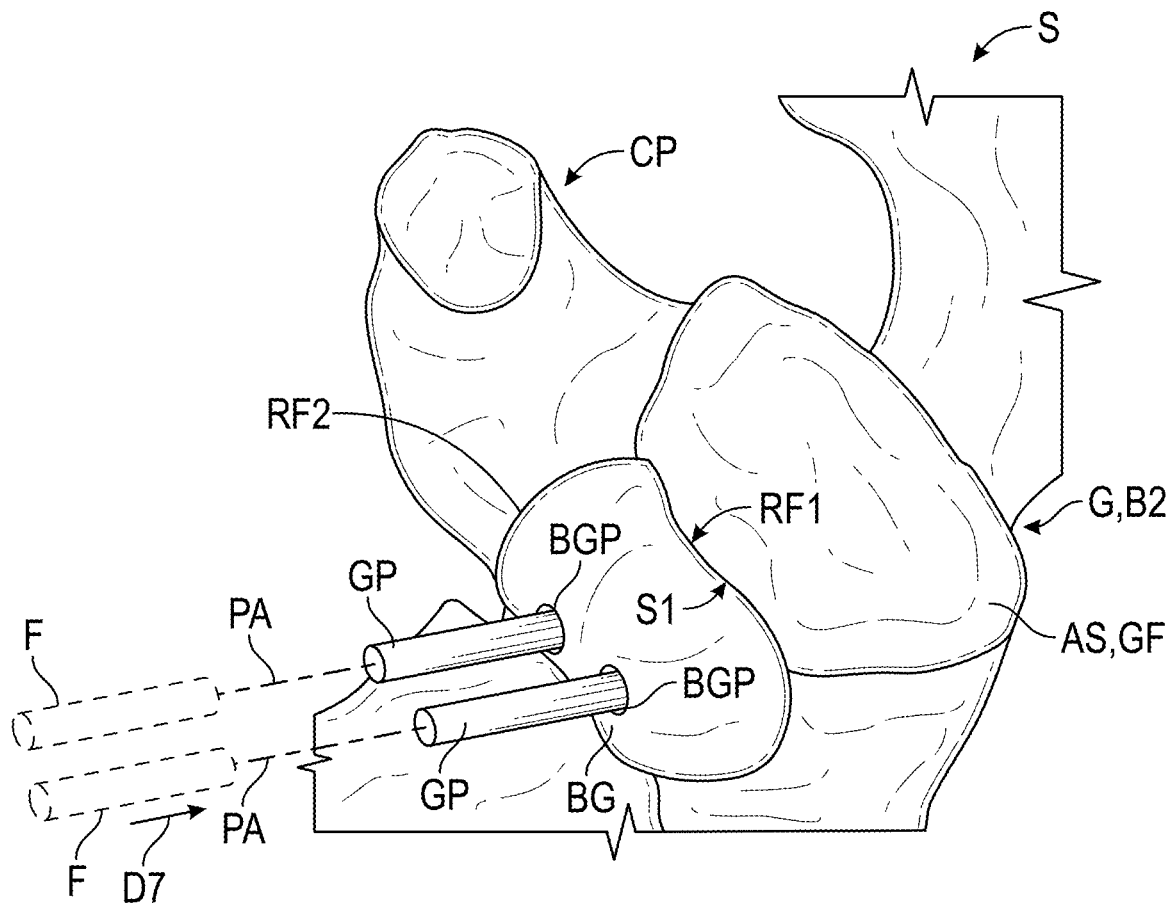
FIGS. 48-49 illustrate securing the bone graft of FIGS. 46-47.
Figure 49:
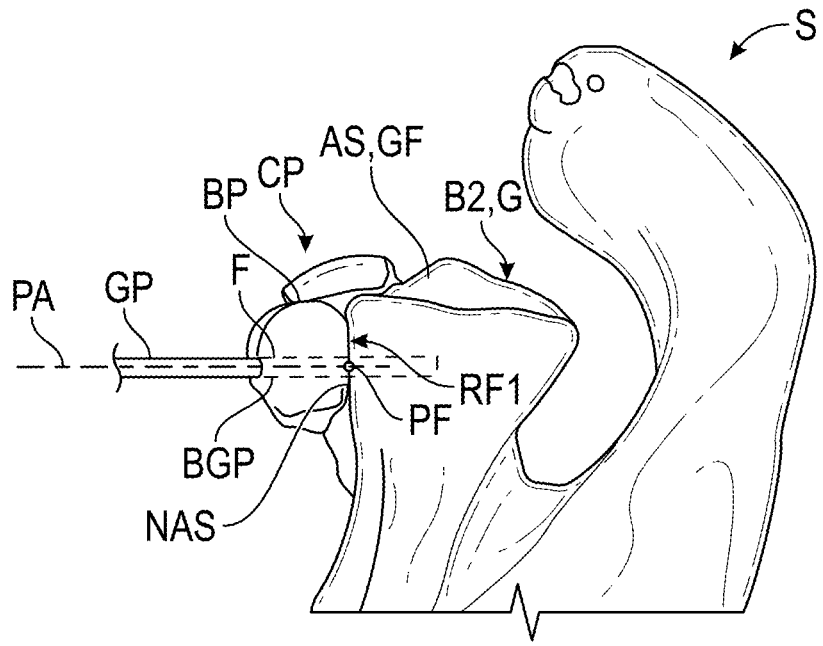

Referring to FIGS. 48-49, with continuing reference to FIGS. 37 and 46-47, the tooling DT2 may be removed from the first shell portion 752-1 and bone graft BG. At step 770R, the bone graft BG may be secured to the portion of bone B2. Various techniques may be utilized to secure the bone graft BG, including one or more fasteners F (shown in dashed lines). Exemplary fasteners can include any of the fasteners disclosed herein. Step 770R may include moving fastener(s)

F in the direction D7 along a respective passage axis PA. Step 770R may include securing the bone graft BG with one at least one fastener F at the insertion point PF, as illustrated in FIG. 49.

One or more finishing operations may be performed at step 770S. Exemplary finishing operations may include closing an incision at the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A guide assembly for an orthopaedic procedure comprising:
    a shell including a first shell portion and a second shell portion dimensioned to abut the first shell portion in an assembled position;
    wherein each of the first and second shell portions includes a shell body extending between opposed end walls, a sidewall of the shell body extends between the end walls, and a recess extends inwardly from the sidewall;
    wherein the recesses of the first and second shell portions cooperate to establish a cavity dimensioned according to a first patient-specific contour, and the first and second shells are dimensioned to capture a first portion of bone associated with the first patient-specific contour within the cavity;
    wherein the sidewall of the first shell portion establishes a first resection plane, one of the end walls of the first shell portion and one of the end walls of the second shell portion cooperate to establish a second resection plane in the assembled position, and the second resection plane is transverse to the first resection plane; and
    an outrigger including a main body extending outwardly from the first shell portion to a free end, wherein the free end is dimensioned to contact an articular surface associated with the second portion of bone.

2. The guide assembly as recited in claim 1, wherein the sidewall of the first shell portion and the sidewall of the second shell portion are dimensioned to abut each other to encircle the cavity in the assembled position.

3. The guide assembly as recited in claim 1, wherein a first depth is established between a floor of the recess and the sidewall of the first shell portion, and the first depth is associated with a dimension of a second portion of bone.

4. The guide assembly as recited in claim 1, wherein the outrigger extends transversely from the first shell portion such that the second shell portion is positioned between the sidewall of the first shell portion and the free end of the outrigger in the assembled position.

5. The guide assembly as recited in claim 1, wherein the outrigger is dimensioned according to a second patient-specific contour associated with the articular surface.

6. The guide assembly as recited in claim 5, wherein the first patient-specific contour is associated with a coracoid process, and the second patient-specific contour associated with the articular surface of a glenoid.

7. The guide assembly as recited in claim 6, wherein the sidewall of the first shell portion is dimensioned to abut an anterior surface of a glenoid in response to contact between the free end of the outrigger and the articular surface.

8. The guide assembly as recited in claim 5, wherein the free end of the outrigger has a surface profile including a plurality of undulations dimensioned to follow the second patient-specific contour.

9. The guide assembly as recited in claim 8, wherein:
    the outrigger is a plurality of outriggers distributed along the sidewall of the first shell portion, and the outriggers are interspersed with a plurality of slots; and
    the free ends of the outriggers are dimensioned according to respective portions of the second patient-specific contour.

10. The guide assembly as recited in claim 1, wherein the first shell portion includes a first passage, the second shell portion includes a second passage, and the first and second passages are substantially aligned in the assembled position such that a drill bit is insertable through the first and second passages and across the cavity.

11. The guide assembly as recited in claim 10, wherein:
    the outrigger extends towards the second shell portion in the assembled position; and
    the outrigger is spaced apart from the first passage of the first shell portion.

12. The guide assembly as recited in claim 1, wherein the first patient-specific contour is associated with a coracoid process.

13. The guide assembly as recited in claim 1, wherein the first shell portion and the second shell portion are releasably securable to each other to establish a clamshell arrangement in the assembled position.

14. The guide assembly as recited in claim 1, wherein surfaces of the recess of the first shell portion face towards the first resection plane.

15. The guide assembly as recited in claim 1, wherein the sidewall of the first shell portion and the sidewall of the second shell portion are dimensioned to abut each other along the first resection plane.

16. A guide assembly for an orthopaedic procedure comprising:
    a shell including a shell body and an outrigger extending outwardly from the shell body to a free end;
    wherein the shell body extends between opposed end walls, a sidewall of the shell body extends between the end walls, a recess extends inwardly from the sidewall to establish a cavity dimensioned according to a first patient-specific contour, and the shell body is dimensioned to capture a first portion of bone associated with the first patient-specific contour within the cavity;
    wherein the sidewall of the shell body establishes a first resection plane, one of the end walls of the shell body establishes a second resection plane, and the second resection plane is transverse to the first resection plane; and
    wherein the free end of the outrigger is dimensioned to contact an articular surface associated with a second portion of bone.

17. The guide assembly as recited in claim 16, wherein a first depth is established between a floor of the recess and the sidewall of the shell body, and the first depth is associated with a dimension of a second portion of bone.

18. The guide assembly as recited in claim 16, wherein the free end of the outrigger is dimensioned according to a second patient-specific contour associated with the articular surface.

19. The guide assembly as recited in claim 18, wherein the first patient-specific contour is associated with a coracoid process, and the second patient-specific contour associated with the articular surface of a glenoid.

20. The guide assembly as recited in claim 16, wherein the outrigger extends transversely from the shell body such that a side of the outrigger faces towards the recess.

21. The guide assembly as recited in claim 16, wherein:
the shell body includes a passage extending along a passage axis from the cavity, and the passage is dimensioned to receive a drill bit; and
the shell body includes a slot that extends radially from the passage relative to the passage axis to segment the sidewall, and the slot is dimensioned to establish a pathway between the passage and an exterior of the shell body.

22. A method of performing an orthopaedic procedure comprising:
fabricating a guide assembly, wherein the guide assembly includes a shell having a first shell portion and a second shell portion that cooperate to establish a cavity, the cavity is dimensioned according to a first patient-specific contour associated with a coracoid process of a patient, a first sidewall of the first shell portion establishes a first resection surface, adjacent end walls of the first and second shell portions establish a second resection surface in an assembled position, an outrigger extends outwardly from the first shell portion to a free end, and the free end is dimensioned to contact a glenoid face of a glenoid;
moving the first and second shell portions together to capture a portion of the coracoid process in the cavity;
removing the portion of the coracoid process to establish a bone graft in response to resecting the coracoid process along the second resection surface;
removing a portion of the bone graft to establish a resection face in response to resecting the bone graft along the first resection surface; and
positioning the free end of the outrigger in abutment with the glenoid face such that the resection face of the bone graft abuts an anterior surface of the glenoid at a predetermined height relative to the glenoid face.

23. The method as recited in claim 22, further comprising:
removing the second shell portion from the first shell portion; and
positioning the first resection surface of the first shell portion in opposition with the anterior surface of the glenoid such that the resection surface of the bone graft abuts the anterior surface of the glenoid at the predetermined height.

24. The method as recited in claim 23, further comprising:
moving a guide pin through a first passage in the first shell portion, then through the bone graft in the cavity, and then into the anterior surface of the glenoid at an insertion point; and
securing the bone graft with one at least one fastener at the insertion point.

25. The method as recited in claim 22, wherein the step of positioning the free end of the outrigger occurs such that the first resection surface abuts the anterior surface of the glenoid, and further comprising:
moving a guide pin through a first passage in the first shell portion, then through the bone graft in the cavity, and then into the anterior surface of the glenoid at an insertion point associated with the predetermined height.

26. The method as recited in claim 25, wherein the step of positioning the free end of the outrigger occurs such that a portion of the bone graft is lateral of the glenoid face during the step of moving the guide pin into the anterior surface of the glenoid.

27. The method as recited in claim 22, wherein the first resection surface is dimensioned with respect to a width of a second patient-specific contour, and the second patient-specific contour is established by a bone loss area bounded by an anterior segment associated with the glenoid face of the patient.

28. The method as recited in claim 27, wherein the second resection surface is dimensioned with respect to a length of the bone loss area between ends of the anterior segment.

* * * * *